(12) United States Patent
Roberts et al.

(10) Patent No.: US 11,345,736 B2
(45) Date of Patent: *May 31, 2022

(54) MULTI-SPECIFIC MOLECULES

(71) Applicant: IMUNEXUS THERAPEUTICS LIMITED, Bundoora (AU)

(72) Inventors: Anthony Simon Roberts, Brunswick (AU); George Kopsidas, Parkville (AU); Michael Ross Luke, Parkville (AU); Phil Anthony Jennings, Parkville (AU)

(73) Assignee: IMUNEXUS THERAPEUTICS LIMITED, Bundoora (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/223,935

(22) Filed: Apr. 6, 2021

(65) Prior Publication Data

US 2021/0230249 A1 Jul. 29, 2021

Related U.S. Application Data

(63) Continuation of application No. 16/946,451, filed on Jun. 22, 2020, which is a continuation of application No. 16/079,949, filed as application No. PCT/AU2017/050168 on Feb. 27, 2017, now abandoned.

(30) Foreign Application Priority Data

Feb. 26, 2016 (AU) ................................. 2016900708
Feb. 26, 2016 (AU) ................................. 2016900709

(51) Int. Cl.
| | | |
|---|---|---|
| C07K 14/705 | (2006.01) | |
| C07K 16/28 | (2006.01) | |
| C07K 16/40 | (2006.01) | |
| C07K 16/46 | (2006.01) | |

(52) U.S. Cl.
CPC .... *C07K 14/70521* (2013.01); *C07K 16/2809* (2013.01); *C07K 16/2827* (2013.01); *C07K 16/40* (2013.01); *C07K 16/468* (2013.01); *C07K 2317/31* (2013.01); *C07K 2317/522* (2013.01); *C07K 2317/524* (2013.01); *C07K 2317/526* (2013.01); *C07K 2317/55* (2013.01); *C07K 2317/92* (2013.01); *C07K 2319/30* (2013.01)

(58) Field of Classification Search
CPC ............ C07K 14/70521; C07K 16/468; C07K 2317/31

See application file for complete search history.

(56) References Cited

U.S. PATENT DOCUMENTS

| | | |
|---|---|---|
| 7,166,697 B1 | 1/2007 | Galanis et al. |
| 2009/0259026 A1 | 10/2009 | Tomlinson et al. |
| 2010/0081792 A1 | 4/2010 | Grant et al. |
| 2012/0064064 A1 | 3/2012 | Batuwangala et al. |
| 2017/0145080 A1 | 5/2017 | Tomlinson et al. |
| 2021/0040177 A1* | 2/2021 | Roberts .............. C07K 16/2827 |

FOREIGN PATENT DOCUMENTS

| | | |
|---|---|---|
| CN | 101932608 A | 12/2010 |
| CN | 102227447 A | 10/2011 |
| JP | 2002505103 A | 2/2002 |
| JP | 2010518062 A | 5/2010 |
| JP | 2011504742 A | 2/2011 |
| JP | 2012528112 A | 11/2012 |
| WO | 9945110 A1 | 9/1999 |
| WO | 2000060070 A1 | 10/2000 |
| WO | 2008096158 A3 | 12/2008 |
| WO | 2009068649 A2 | 6/2009 |
| WO | 2010136492 A2 | 12/2010 |

OTHER PUBLICATIONS

Australian Patent Office, Examination Report No. 1; Application Serial No. AU2017222700; dated Mar. 16, 2018; 5 pages.
Australian Patent Office, Examination Report No. 2; Application Serial No. AU2017222700; dated Jun. 29, 2018; 3 pages.
Australian Patent Office, International Search Report & Written Opinion PCT/AU2017/050168; dated Mar. 15, 2018; 21 pages.
Australian Patent Office, Notice of Acceptance of Patent Application; Application Serial No. AU2017222700; dated Sep. 13, 2018; 3 pages.
Chinnasamy, et al., A Mechanistic study of immune system activation by fusion of antigens with the ligand-binding domain of CTLA4, 313 Apr. 2006, Cancer Immunol Immunother 55:1504-1514.
European Patent Office, "Extended European Search Report" for EP Application No. 17755659.4dated Sep. 19, 2019, 7 pages.
Response to AU Examination Report No. 1 of AU Patent Application 2017222700; dated May 25, 2018; 19 pages.
Response to AU Examination Report No. 2 of AU Patent Application 2017222700; dated Aug. 3, 2018; 3 pages.
Vazquez-Lombardi, et al, Challenges and opportunities for non-antibody scaffold drugs, Oct. 10, 2015, Drug Discovery Today—vol. 20, No. 10, 1271-1283.

(Continued)

*Primary Examiner* — Jessica H Roark
(74) *Attorney, Agent, or Firm* — Storella & Witt, LLP

(57) ABSTRACT

The present disclosure relates to multi-specific molecules which are capable of simultaneously binding at least two different target antigens or epitopes. The molecules comprise at least one binding domain molecule (BDM) which hinds to a first target antigen or epitope, the BDM being modified for selective binding to a heterologous target, coupled to a pharmacologically active protein or peptide which is an antibody or antigen-binding fragment thereof or a non-antibody protein or peptide which binds to a second target antigen or epitope, the BDMs being coupled to a C-terminus of a polypeptide present within the pharmacologically active protein or peptide.

21 Claims, 29 Drawing Sheets

Specification includes a Sequence Listing.

(56) References Cited

OTHER PUBLICATIONS

Weidle, et al, The Emerging Role of New Protein Scaffold-based Agents for Treatment of Cancer, Cancer Genomics & Proteomics 10, 2013, 155-168.

Kitamura, Japanese Patent Office "Notice of Reasons for Rejection" for JP Application No. 2018-0563747, dated Apr. 5, 2021, 11 pages.

Hufton, Simon E., et al., "Development and application of cytotoxic T lymphocyte-associated antigen 4 as a protein scaffold for the generation of novel binding ligands", FEBS Letters 475 (2000) 225-231.

Nuttall, Stewart D., et al., "Design and Expression of Soluble CTLA-4 Variable Domain as a Scaffold for the Display of Functional Polypeptides", PROTEINS: Structure, Function, and Genetics 36:217-227 (1999).

\* cited by examiner

A. Native human CTLA4 VLD scaffold

1 25 34 54 60
KAMHVAQPAVVLASSRGIASFVCEYASPGKATEVRVTVLRQADSQVTEVCAATYMMGNELTFLDDSICTGTSSGNQVNLTIQGLRAMDTG
*framework* *BL1* *framework* *BL2* *framework*

96 106 126
LYICKVELMYPPPYYLGIGNGTQIYVIDPEPSPDSN
*BL3* *framework*

(SEQ ID NO:1)

B. CTLA4 VLD binding loop replacements

KAMHVAQPAVVLASSRGIASFVCEY $Xn_1$ VRVTVLRQADSQVTEVCAATY $Xn_2$ LTFLDDSICTGTSSGNQVNLTIQGLRAMDTGLYICKV $Xn_3$ LGIGNGTQIYVIDPEPSPDSN (SEQ ID NO:5)

C. Sclerostin human VLD scaffold

KAMHVAQPAVVLASSRGIASFVCEYTVSWVDMEVRVTVLRQADSQVTEVCAATYWNGRWLTFLDDSICTGTSSGNQVNLTIQGLRAMDT

GLYICKVQLDPSWGYYWQGYEGIGNGTQIYVIDPEPSPDSN

SEQUENCE LISTING

<160> NUMBER OF SEQ ID NOS: 44

<210> SEQ ID NO 1
<211> LENGTH: 126
<212> TYPE: PRT
<213> ORGANISM: Homo sapiens

<400> SEQUENCE: 1

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp

```
                50                  55                  60
Asp Ser Ile Cys Thr Gly Thr Ser Ser Gly Asn Gln Val Asn Leu Thr
 65                  70                  75                  80

Ile Gln Gly Leu Arg Ala Met Asp Thr Gly Leu Tyr Ile Cys Lys Val
                 85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Ser Pro Asp Ser Asn
            115                 120                 125
```

<210> SEQ ID NO 2
<211> LENGTH: 8
<212> TYPE: PRT
<213> ORGANISM: Homo sapiens

<400> SEQUENCE: 2

```
Ala Ser Pro Gly Lys Ala Thr Glu
 1               5
```

<210> SEQ ID NO 3
<211> LENGTH: 5
<212> TYPE: PRT
<213> ORGANISM: Homo sapiens

<400> SEQUENCE: 3

```
Met Met Gly Asn Glu
 1               5
```

<210> SEQ ID NO 4
<211> LENGTH: 9
<212> TYPE: PRT
<213> ORGANISM: Homo sapiens

<400> SEQUENCE: 4

```
Glu Leu Met Tyr Pro Pro Pro Tyr Tyr
 1               5
```

<210> SEQ ID NO 5
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BDM scaffold sequence
<220> FEATURE:
<221> NAME/KEY: MOD_RES
<222> LOCATION: (26)..(40)
<223> OTHER INFORMATION: Any amino acid
<220> FEATURE:
<221> NAME/KEY: SITE
<222> LOCATION: (26)..(40)
<223> OTHER INFORMATION: This region may encompass 5-15 residues
<220> FEATURE:
<221> NAME/KEY: MOD_RES
<222> LOCATION: (62)..(76)
<223> OTHER INFORMATION: Any amino acid
<220> FEATURE:
<221> NAME/KEY: SITE
<222> LOCATION: (62)..(76)
<223> OTHER INFORMATION: This region may encompass 5-15 residues
<220> FEATURE:
<221> NAME/KEY: MOD_RES
<222> LOCATION: (114)..(128)
<223> OTHER INFORMATION: Any amino acid
<220> FEATURE:
<221> NAME/KEY: SITE

```
<222> LOCATION: (114)..(128)
<223> OTHER INFORMATION: This region may encompass 5-15 residues

<400> SEQUENCE: 5

Lys Ala Met His Val Ala Gln Pro Ala Val Val Leu Ala Ser Ser Arg
1               5                   10                  15

Gly Ile Ala Ser Phe Val Cys Glu Tyr Xaa Xaa Xaa Xaa Xaa Xaa
            20                  25                  30

Xaa Xaa Xaa Xaa Xaa Xaa Xaa Xaa Val Arg Val Thr Val Leu Arg Gln
        35                  40                  45

Ala Asp Ser Gln Val Thr Glu Val Cys Ala Ala Thr Tyr Xaa Xaa Xaa
    50                  55                  60

Xaa Xaa Xaa Xaa Xaa Xaa Xaa Xaa Xaa Xaa Xaa Leu Thr Phe Leu
65                  70                  75                  80

Asp Asp Ser Ile Cys Thr Gly Thr Ser Ser Gly Asn Gln Val Asn Leu
                85                  90                  95

Thr Ile Gln Gly Leu Arg Ala Met Asp Thr Gly Leu Tyr Ile Cys Lys
                100                 105                 110

Val Xaa Xaa Xaa Xaa Xaa Xaa Xaa Xaa Xaa Xaa Xaa Xaa Xaa Xaa
        115                 120                 125

Leu Gly Ile Gly Asn Gly Thr Gln Ile Tyr Val Ile Asp Pro Glu Pro
    130                 135                 140

Ser Pro Asp Ser Asn
145

<210> SEQ ID NO 6
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: BDM scaffold sequence
<220> FEATURE:
<221> NAME/KEY: MOD_RES
<222> LOCATION: (26)..(40)
<223> OTHER INFORMATION: Any amino acid
<220> FEATURE:
<221> NAME/KEY: SITE
<222> LOCATION: (26)..(40)
<223> OTHER INFORMATION: This region may encompass 5-15 residues
<220> FEATURE:
<221> NAME/KEY: MOD_RES
<222> LOCATION: (63)..(77)
<223> OTHER INFORMATION: Any amino acid
<220> FEATURE:
<221> NAME/KEY: SITE
<222> LOCATION: (63)..(77)
<223> OTHER INFORMATION: This region may encompass 5-15 residues
<220> FEATURE:
<221> NAME/KEY: MOD_RES
<222> LOCATION: (115)..(129)
<223> OTHER INFORMATION: Any amino acid
<220> FEATURE:
<221> NAME/KEY: SITE
<222> LOCATION: (115)..(129)
<223> OTHER INFORMATION: This region may encompass 5-15 residues

<400> SEQUENCE: 6

Lys Ala Met His Val Ala Gln Pro Ala Val Val Leu Ala Ser Ser Arg
1               5                   10                  15

Gly Ile Ala Ser Phe Val Cys Glu Tyr Xaa Xaa Xaa Xaa Xaa Xaa
            20                  25                  30

Xaa Xaa Xaa Xaa Xaa Xaa Xaa Xaa Glu Val Arg Val Thr Val Leu Arg
```

```
                35                  40                  45
Gln Ala Asp Ser Gln Val Thr Glu Val Cys Ala Ala Thr Tyr Xaa Xaa
            50                  55                  60
Xaa Xaa Xaa Xaa Xaa Xaa Xaa Xaa Xaa Xaa Xaa Xaa Leu Thr Phe
 65                  70                  75                  80
Leu Asp Asp Ser Ile Cys Thr Gly Thr Ser Gly Asn Gln Val Asn
                85                  90                  95
Leu Thr Ile Gln Gly Leu Arg Ala Met Asp Thr Gly Leu Tyr Ile Cys
            100                 105                 110
Lys Val Xaa Xaa Xaa Xaa Xaa Xaa Xaa Xaa Xaa Xaa Xaa Xaa
        115                 120                 125
Xaa Gly Ile Gly Asn Gly Thr Gln Ile Tyr Val Ile Asp Pro Glu Pro
    130                 135                 140
Ser Pro Asp Ser Asn
145
```

<210> SEQ ID NO 7
<211> LENGTH: 8
<212> TYPE: PRT
<213> ORGANISM: Homo sapiens

<400> SEQUENCE: 7

```
Ala Ser Pro Gly Lys Tyr Thr Glu
1               5
```

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: signal peptide

<400> SEQUENCE: 8

```
Met Ala Trp Met Met Leu Leu Gly Leu Leu Ala Tyr Gly Ser Gly
1               5                   10                  15
```

<210> SEQ ID NO 9
<211> LENGTH: 10
<212> TYPE: PRT
<213> ORGANISM: Homo sapiens

<400> SEQUENCE: 9

```
Glu Leu Met Tyr Pro Pro Tyr Tyr Leu
1               5                   10
```

<210> SEQ ID NO 10
<211> LENGTH: 8
<212> TYPE: PRT
<213> ORGANISM: Homo sapiens

<400> SEQUENCE: 10

```
Thr Val Ser Trp Val Asp Met Glu
1               5
```

<210> SEQ ID NO 11
<211> LENGTH: 5
<212> TYPE: PRT
<213> ORGANISM: Homo sapiens

<400> SEQUENCE: 11

-continued

```
Trp Asn Gly Arg Trp
1               5

<210> SEQ ID NO 12
<211> LENGTH: 14
<212> TYPE: PRT
<213> ORGANISM: Homo sapiens

<400> SEQUENCE: 12

Gln Leu Asp Pro Ser Trp Gly Tyr Tyr Trp Gln Gly Tyr Glu
1               5                   10

<210> SEQ ID NO 13
<211> LENGTH: 126
<212> TYPE: PRT
<213> ORGANISM: Homo sapiens

<400> SEQUENCE: 13

Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Tyr Thr
                20                  25                  30

Glu Val Arg Val Thr Val Leu Arg Gln Ala Asp Ser Gln Val Thr Glu
            35                  40                  45

Val Cys Ala Ala Thr Tyr Met Thr Gly Asn Glu Leu Thr Phe Leu Asp
        50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Leu Gly Ile Gly Asn Gly Thr
                100                 105                 110

Gln Ile Tyr Val Ile Asp Pro Glu Pro Ser Pro Asp Ser Asn
            115                 120                 125

<210> SEQ ID NO 14
<211> LENGTH: 130
<212> TYPE: PRT
<213> ORGANISM: Homo sapiens

<400> SEQUENCE: 14

Lys Ala Met His Val Ala Gln Pro Ala Val Val Leu Ala Ser Ser Arg
1               5                   10                  15

Gly Ile Ala Ser Phe Val Cys Glu Tyr Thr Val Ser Trp Val Asp Met
                20                  25                  30

Glu Val Arg Val Thr Val Leu Arg Gln Ala Asp Ser Gln Val Thr Glu
            35                  40                  45

Val Cys Ala Ala Thr Tyr Trp Asn Gly Arg Trp Leu Thr Phe Leu Asp
        50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Gln Leu Asp Pro Ser Trp Gly Tyr Tyr Trp Gln Gly Tyr Glu Gly Ile
                100                 105                 110

Gly Asn Gly Thr Gln Ile Tyr Val Ile Asp Pro Glu Pro Ser Pro Asp
            115                 120                 125
```

Ser Asn
    130

<210> SEQ ID NO 15
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: linker sequence
<220> FEATURE:
<221> NAME/KEY: SITE
<222> LOCATION: (1)..(40)
<223> OTHER INFORMATION: This sequence may encompass 2-8 "Ser Gly Gly
      Gly Gly" repeating units
<220> FEATURE:
<223> OTHER INFORMATION: See specification as filed for detailed
      description of substitutions and preferred embodiments

<400> SEQUENCE: 15

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser
        35                  40

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence

<400> SEQUENCE: 16

Ser Gly Gly Gly Gly Ser Gly Gly Gly Gly Ser Gly Gly Gly Gly Ser
1               5                   10                  15

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence

<400> SEQUENCE: 17

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 18
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

-continued

```
Glu Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Ala Leu Lys
50                  55                  60

Ser Arg Leu Ser Ile Ser Lys Asp Asn Ser Lys Ser Gln Val Phe Leu
65                  70                  75                  80

Lys Met Asn Ser Leu His Thr Asp Asp Thr Ala Arg Tyr Tyr Cys Ala
                85                  90                  95

Arg Glu Arg Asp Tyr Arg Leu Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

His Asn His Tyr Thr Gln Lys Ser Leu Ser Leu Ser Pro Gly Lys
435                 440                 445

<210> SEQ ID NO 19
<211> LENGTH: 589
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu His Thr Asp Asp Thr Ala Arg Tyr Tyr Cys Ala
                85                  90                  95

Arg Glu Arg Asp Tyr Arg Leu Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Gly Gly Gly Ser Gly Gly Gly Ser Gly Gly Gly Gly Ser Lys
    450                 455                 460

Ala Met His Val Ala Gln Pro Ala Val Val Leu Ala Ser Ser Arg Gly
465                 470                 475                 480

Ile Ala Ser Phe Val Cys Glu Tyr Ala Ser Pro Gly Lys Tyr Thr Glu
                485                 490                 495

Val Arg Val Thr Val Leu Arg Gln Ala Asp Ser Gln Val Thr Glu Val
            500                 505                 510

Cys Ala Ala Thr Tyr Met Thr Gly Asn Glu Leu Thr Phe Leu Asp Asp
        515                 520                 525

Ser Ile Cys Thr Gly Thr Ser Ser Gly Asn Gln Val Asn Leu Thr Ile
    530                 535                 540

Gln Gly Leu Arg Ala Met Asp Thr Gly Leu Tyr Ile Cys Lys Val Glu
545                 550                 555                 560

Leu Met Tyr Pro Pro Pro Tyr Tyr Leu Gly Ile Gly Asn Gly Thr Gln
                565                 570                 575

Ile Tyr Val Ile Asp Pro Glu Pro Ser Pro Asp Ser Asn
            580                 585

<210> SEQ ID NO 20
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Glu Leu Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Tyr Thr Thr Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Leu Lys Arg Thr Val Ala Ala
            100                 105                 110

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Asp Ile Glu Leu Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Tyr Thr Thr Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Ser Gly Gly Gly
    210                 215                 220

Ser Gly Gly Gly Gly Ser Gly Gly Gly Ser Lys Ala Met His Val
225                 230                 235                 240

Ala Gln Pro Ala Val Val Leu Ala Ser Ser Arg Gly Ile Ala Ser Phe
```

```
                245                 250                 255
Val Cys Glu Tyr Ala Ser Pro Gly Lys Tyr Thr Glu Val Arg Val Thr
            260                 265                 270

Val Leu Arg Gln Ala Asp Ser Gln Val Thr Glu Val Cys Ala Ala Thr
            275                 280                 285

Tyr Met Thr Gly Asn Glu Leu Thr Phe Leu Asp Asp Ser Ile Cys Thr
            290                 295                 300

Gly Thr Ser Ser Gly Asn Gln Val Asn Leu Thr Ile Gln Gly Leu Arg
305                 310                 315                 320

Ala Met Asp Thr Gly Leu Tyr Ile Cys Lys Val Glu Leu Met Tyr Pro
                325                 330                 335

Pro Pro Tyr Tyr Leu Gly Ile Gly Asn Gly Thr Gln Ile Tyr Val Ile
                340                 345                 350

Asp Pro Glu Pro Ser Pro Asp Ser Asn
                355                 360

<210> SEQ ID NO 22
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Glu Leu Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ala Trp Tyr Gln Gln Lys Gln Gly Lys Ser Pro Gln Leu Leu Val
            35                  40                  45

Tyr Tyr Thr Thr Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Ser Gly Gly Gly Ser Gly Gly Gly Gly
        210                 215                 220

Ser Gly Gly Gly Gly Ser Gly Gly Gly Ser Lys Ala Met His Val
225                 230                 235                 240
```

```
Ala Gln Pro Ala Val Val Leu Ala Ser Ser Arg Gly Ile Ala Ser Phe
            245                 250                 255

Val Cys Glu Tyr Ala Ser Pro Gly Lys Tyr Thr Glu Val Arg Val Thr
            260                 265                 270

Val Leu Arg Gln Ala Asp Ser Gln Val Thr Glu Val Cys Ala Ala Thr
            275                 280                 285

Tyr Met Thr Gly Asn Glu Leu Thr Phe Leu Asp Asp Ser Ile Cys Thr
            290                 295                 300

Gly Thr Ser Ser Gly Asn Gln Val Asn Leu Thr Ile Gln Gly Leu Arg
305                 310                 315                 320

Ala Met Asp Thr Gly Leu Tyr Ile Cys Lys Val Glu Leu Met Tyr Pro
                325                 330                 335

Pro Pro Tyr Tyr Leu Gly Ile Gly Asn Gly Thr Gln Ile Tyr Val Ile
            340                 345                 350

Asp Pro Glu Pro Ser Pro Asp Ser Asn
            355                 360
```

<210> SEQ ID NO 23
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Glu Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
            35                  40                  45

Gly Met Ile Trp Gly Asp Gly Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu His Thr Asp Thr Ala Arg Tyr Tyr Cys Ala
                85                  90                  95

Arg Glu Arg Asp Tyr Arg Leu Asp Tyr Trp Gly Gln Gly Thr Thr Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Ser Gly Gly Gly Gly
        210                 215                 220

Ser Gly Gly Gly Gly Ser Gly Gly Gly Gly Ser Gly Gly Gly Gly Ser
225                 230                 235                 240
```

```
Lys Ala Met His Val Ala Gln Pro Ala Val Leu Ala Ser Ser Arg
                245                 250                 255

Gly Ile Ala Ser Phe Val Cys Glu Tyr Ala Ser Pro Gly Lys Tyr Thr
            260                 265                 270

Glu Val Arg Val Thr Val Leu Arg Gln Ala Asp Ser Gln Val Thr Glu
        275                 280                 285

Val Cys Ala Ala Thr Tyr Met Thr Gly Asn Glu Leu Thr Phe Leu Asp
290                 295                 300

Asp Ser Ile Cys Thr Gly Thr Ser Ser Gly Asn Gln Val Asn Leu Thr
305                 310                 315                 320

Ile Gln Gly Leu Arg Ala Met Asp Thr Gly Leu Tyr Ile Cys Lys Val
                325                 330                 335

Glu Leu Met Tyr Pro Pro Pro Tyr Tyr Leu Gly Ile Gly Asn Gly Thr
            340                 345                 350

Gln Ile Tyr Val Ile Asp Pro Glu Pro Ser Pro Asp Ser Asn
        355                 360                 365

<210> SEQ ID NO 24
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu His Thr Asp Asp Thr Ala Arg Tyr Tyr Cys Ala
                85                  90                  95

Arg Glu Arg Asp Tyr Arg Leu Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Ala Ala Ala Gly Leu
    210                 215                 220

Gly Gly His His His His His His Gly Ala Ala Glu Gln Lys Leu Ile
```

Ser Glu Glu Asp Leu
            245

<210> SEQ ID NO 25
<211> LENGTH: 593
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Lys Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Asn Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu His Thr Asp Asp Thr Ala Arg Tyr Tyr Cys Ala
                85                  90                  95

Arg Glu Arg Asp Tyr Arg Leu Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
             340                 345                 350

Pro Ser Arg Asp Glu Leu Thr Lys Asn Gln Val Ser Leu Thr Cys Leu
         355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys Ser
        435                 440                 445

Gly Gly Gly Gly Ser Gly Gly Gly Ser Gly Gly Gly Gly Ser Lys
    450                 455                 460

Ala Met His Val Ala Gln Pro Ala Val Val Leu Ala Ser Ser Arg Gly
465                 470                 475                 480

Ile Ala Ser Phe Val Cys Glu Tyr Thr Val Ser Trp Val Asp Met Glu
                485                 490                 495

Val Arg Val Thr Val Leu Arg Gln Ala Asp Ser Gln Val Thr Glu Val
            500                 505                 510

Cys Ala Ala Thr Tyr Trp Asn Gly Arg Trp Leu Thr Phe Leu Asp Asp
        515                 520                 525

Ser Ile Cys Thr Gly Thr Ser Ser Gly Asn Gln Val Asn Leu Thr Ile
    530                 535                 540

Gln Gly Leu Arg Ala Met Asp Thr Gly Leu Tyr Ile Cys Lys Val Gln
545                 550                 555                 560

Leu Asp Pro Ser Trp Gly Tyr Tyr Trp Gln Gly Tyr Glu Gly Ile Gly
                565                 570                 575

Asn Gly Thr Gln Ile Tyr Val Ile Asp Pro Glu Pro Ser Pro Asp Ser
            580                 585                 590

Asn

<210> SEQ ID NO 26
<211> LENGTH: 735
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

```
Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
        260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
```

-continued

```
                515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Ser Gly Gly Gly Ser Gly
                580                 585                 590
Gly Gly Gly Ser Gly Gly Gly Ser Lys Ala Met His Val Ala Gln
                595                 600                 605
Pro Ala Val Leu Ala Ser Ser Arg Gly Ile Ala Ser Phe Val Cys
610                 615                 620
Glu Tyr Ala Ser Pro Gly Lys Ala Thr Glu Val Arg Val Thr Val Leu
625                 630                 635                 640
Arg Gln Ala Asp Ser Gln Val Thr Glu Val Cys Ala Ala Thr Tyr Met
                645                 650                 655
Met Gly Asn Glu Leu Thr Phe Leu Asp Asp Ser Ile Cys Thr Gly Thr
                660                 665                 670
Ser Ser Gly Asn Gln Val Asn Leu Thr Ile Gln Gly Leu Arg Ala Met
                675                 680                 685
Asp Thr Gly Leu Tyr Ile Cys Lys Val Glu Leu Met Tyr Pro Pro Pro
690                 695                 700
Tyr Tyr Leu Gly Ile Gly Asn Gly Thr Gln Ile Tyr Val Ile Asp Pro
705                 710                 715                 720
Glu Pro Ser Pro Asp Ser Ala Ala Ala His His His His His His
                725                 730                 735

<210> SEQ ID NO 27
<211> LENGTH: 734
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Lys Ala Met His Val Ala Gln Pro Ala Val Leu Ala Ser Ser Arg
1               5                   10                  15

Gly Ile Ala Ser Phe Val Cys Glu Tyr Ala Ser Pro Gly Lys Ala Thr
                20                  25                  30

Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Leu Asp
        50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Ser Pro Asp Ser Gly Gly Gly
        115                 120                 125

Gly Ser Gly Gly Gly Gly Ser Gly Gly Gly Gly Ser Asp Ala His Lys
    130                 135                 140
```

-continued

```
Ser Glu Val Ala His Arg Phe Lys Asp Leu Gly Glu Glu Asn Phe Lys
145                 150                 155                 160

Ala Leu Val Leu Ile Ala Phe Ala Gln Tyr Leu Gln Gln Cys Pro Phe
                165                 170                 175

Glu Asp His Val Lys Leu Val Asn Glu Val Thr Glu Phe Ala Lys Thr
            180                 185                 190

Cys Val Ala Asp Glu Ser Ala Glu Asn Cys Asp Lys Ser Leu His Thr
        195                 200                 205

Leu Phe Gly Asp Lys Leu Cys Thr Val Ala Thr Leu Arg Glu Thr Tyr
    210                 215                 220

Gly Glu Met Ala Asp Cys Cys Ala Lys Gln Glu Pro Glu Arg Asn Glu
225                 230                 235                 240

Cys Phe Leu Gln His Lys Asp Asp Asn Pro Asn Leu Pro Arg Leu Val
                245                 250                 255

Arg Pro Glu Val Asp Val Met Cys Thr Ala Phe His Asp Asn Glu Glu
            260                 265                 270

Thr Phe Leu Lys Lys Tyr Leu Tyr Glu Ile Ala Arg Arg His Pro Tyr
        275                 280                 285

Phe Tyr Ala Pro Glu Leu Leu Phe Phe Ala Lys Arg Tyr Lys Ala Ala
    290                 295                 300

Phe Thr Glu Cys Cys Gln Ala Ala Asp Lys Ala Ala Cys Leu Leu Pro
305                 310                 315                 320

Lys Leu Asp Glu Leu Arg Asp Glu Gly Lys Ala Ser Ser Ala Lys Gln
                325                 330                 335

Arg Leu Lys Cys Ala Ser Leu Gln Lys Phe Gly Glu Arg Ala Phe Lys
            340                 345                 350

Ala Trp Ala Val Ala Arg Leu Ser Gln Arg Phe Pro Lys Ala Glu Phe
        355                 360                 365

Ala Glu Val Ser Lys Leu Val Thr Asp Leu Thr Lys Val His Thr Glu
    370                 375                 380

Cys Cys His Gly Asp Leu Leu Glu Cys Ala Asp Asp Arg Ala Asp Leu
385                 390                 395                 400

Ala Lys Tyr Ile Cys Glu Asn Gln Asp Ser Ile Ser Ser Lys Leu Lys
                405                 410                 415

Glu Cys Cys Glu Lys Pro Leu Leu Glu Lys Ser His Cys Ile Ala Glu
            420                 425                 430

Val Glu Asn Asp Glu Met Pro Ala Asp Leu Pro Ser Leu Ala Ala Asp
        435                 440                 445

Phe Val Glu Ser Lys Asp Val Cys Lys Asn Tyr Ala Glu Ala Lys Asp
    450                 455                 460

Val Phe Leu Gly Met Phe Leu Tyr Glu Tyr Ala Arg Arg His Pro Asp
465                 470                 475                 480

Tyr Ser Val Val Leu Leu Leu Arg Leu Ala Lys Thr Tyr Glu Thr Thr
                485                 490                 495

Leu Glu Lys Cys Cys Ala Ala Ala Asp Pro His Glu Cys Tyr Ala Lys
            500                 505                 510

Val Phe Asp Glu Phe Lys Pro Leu Val Glu Glu Pro Gln Asn Leu Ile
        515                 520                 525

Lys Gln Asn Cys Glu Leu Phe Glu Gln Leu Gly Glu Tyr Lys Phe Gln
    530                 535                 540

Asn Ala Leu Leu Val Arg Tyr Thr Lys Lys Val Pro Gln Val Ser Thr
545                 550                 555                 560

Pro Thr Leu Val Glu Val Ser Arg Asn Leu Gly Lys Val Gly Ser Lys
```

-continued

```
                565                 570                 575
Cys Cys Lys His Pro Glu Ala Lys Arg Met Pro Cys Ala Glu Asp Tyr
            580                 585                 590

Leu Ser Val Val Leu Asn Gln Leu Cys Val Leu His Glu Lys Thr Pro
            595                 600                 605

Val Ser Asp Arg Val Thr Lys Cys Cys Thr Glu Ser Leu Val Asn Arg
610                 615                 620

Arg Pro Cys Phe Ser Ala Leu Glu Val Asp Glu Thr Tyr Val Pro Lys
625                 630                 635                 640

Glu Phe Asn Ala Glu Thr Phe Thr Phe His Ala Asp Ile Cys Thr Leu
            645                 650                 655

Ser Glu Lys Glu Arg Gln Ile Lys Lys Gln Thr Ala Leu Val Glu Leu
            660                 665                 670

Val Lys His Lys Pro Lys Ala Thr Lys Glu Gln Leu Lys Ala Val Met
            675                 680                 685

Asp Asp Phe Ala Ala Phe Val Glu Lys Cys Cys Lys Ala Asp Asp Lys
690                 695                 700

Glu Thr Cys Phe Ala Glu Glu Gly Lys Lys Leu Val Ala Ala Ser Gln
705                 710                 715                 720

Ala Ala Leu Gly Leu Ala Ala His His His His His His
            725                 730
```

<210> SEQ ID NO 28
<211> LENGTH: 875
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
            20                  25                  30

Glu Val Arg Val Thr Val Leu Arg Gln Ala Asp Ser Gln Val Thr Glu
        35                  40                  45

Val Cys Ala Ala Thr Tyr Met Met Gly Asn Glu Leu Thr Phe Leu Asp
    50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
            100                 105                 110

Gln Ile Tyr Val Ile Asp Pro Glu Pro Ser Pro Asp Ser Gly Gly Gly
        115                 120                 125

Gly Ser Gly Gly Gly Gly Ser Gly Gly Gly Gly Ser Asp Ala His Lys
    130                 135                 140

Ser Glu Val Ala His Arg Phe Lys Asp Leu Gly Glu Glu Asn Phe Lys
145                 150                 155                 160

Ala Leu Val Leu Ile Ala Phe Ala Gln Tyr Leu Gln Gln Cys Pro Phe
                165                 170                 175

Glu Asp His Val Lys Leu Val Asn Glu Val Thr Glu Phe Ala Lys Thr
            180                 185                 190
```

```
Cys Val Ala Asp Glu Ser Ala Glu Asn Cys Asp Lys Ser Leu His Thr
            195                 200                 205

Leu Phe Gly Asp Lys Leu Cys Thr Val Ala Thr Leu Arg Glu Thr Tyr
    210                 215                 220

Gly Glu Met Ala Asp Cys Cys Ala Lys Gln Glu Pro Glu Arg Asn Glu
225                 230                 235                 240

Cys Phe Leu Gln His Lys Asp Asp Asn Pro Asn Leu Pro Arg Leu Val
                245                 250                 255

Arg Pro Glu Val Asp Val Met Cys Thr Ala Phe His Asp Asn Glu Glu
            260                 265                 270

Thr Phe Leu Lys Lys Tyr Leu Tyr Glu Ile Ala Arg Arg His Pro Tyr
        275                 280                 285

Phe Tyr Ala Pro Glu Leu Leu Phe Phe Ala Lys Arg Tyr Lys Ala Ala
    290                 295                 300

Phe Thr Glu Cys Cys Gln Ala Ala Asp Lys Ala Ala Cys Leu Leu Pro
305                 310                 315                 320

Lys Leu Asp Glu Leu Arg Asp Glu Gly Lys Ala Ser Ser Ala Lys Gln
                325                 330                 335

Arg Leu Lys Cys Ala Ser Leu Gln Lys Phe Gly Glu Arg Ala Phe Lys
            340                 345                 350

Ala Trp Ala Val Ala Arg Leu Ser Gln Arg Phe Pro Lys Ala Glu Phe
        355                 360                 365

Ala Glu Val Ser Lys Leu Val Thr Asp Leu Thr Lys Val His Thr Glu
    370                 375                 380

Cys Cys His Gly Asp Leu Leu Glu Cys Ala Asp Asp Arg Ala Asp Leu
385                 390                 395                 400

Ala Lys Tyr Ile Cys Glu Asn Gln Asp Ser Ile Ser Ser Lys Leu Lys
                405                 410                 415

Glu Cys Cys Glu Lys Pro Leu Leu Glu Lys Ser His Cys Ile Ala Glu
            420                 425                 430

Val Glu Asn Asp Glu Met Pro Ala Asp Leu Pro Ser Leu Ala Ala Asp
        435                 440                 445

Phe Val Glu Ser Lys Asp Val Cys Lys Asn Tyr Ala Glu Ala Lys Asp
    450                 455                 460

Val Phe Leu Gly Met Phe Leu Tyr Glu Tyr Ala Arg Arg His Pro Asp
465                 470                 475                 480

Tyr Ser Val Val Leu Leu Leu Arg Leu Ala Lys Thr Tyr Glu Thr Thr
                485                 490                 495

Leu Glu Lys Cys Cys Ala Ala Ala Asp Pro His Glu Cys Tyr Ala Lys
            500                 505                 510

Val Phe Asp Glu Phe Lys Pro Leu Val Glu Glu Pro Gln Asn Leu Ile
        515                 520                 525

Lys Gln Asn Cys Glu Leu Phe Glu Gln Leu Gly Glu Tyr Lys Phe Gln
    530                 535                 540

Asn Ala Leu Leu Val Arg Tyr Thr Lys Lys Val Pro Gln Val Ser Thr
545                 550                 555                 560

Pro Thr Leu Val Glu Val Ser Arg Asn Leu Gly Lys Val Gly Ser Lys
                565                 570                 575

Cys Cys Lys His Pro Glu Ala Lys Arg Met Pro Cys Ala Glu Asp Tyr
            580                 585                 590

Leu Ser Val Val Leu Asn Gln Leu Cys Val Leu His Glu Lys Thr Pro
        595                 600                 605

Val Ser Asp Arg Val Thr Lys Cys Cys Thr Glu Ser Leu Val Asn Arg
```

```
                    610                 615                 620
Arg Pro Cys Phe Ser Ala Leu Glu Val Asp Glu Thr Tyr Val Pro Lys
625                 630                 635                 640

Glu Phe Asn Ala Glu Thr Phe Thr Phe His Ala Asp Ile Cys Thr Leu
                    645                 650                 655

Ser Glu Lys Glu Arg Gln Ile Lys Lys Gln Thr Ala Leu Val Glu Leu
                    660                 665                 670

Val Lys His Lys Pro Lys Ala Thr Lys Glu Gln Leu Lys Ala Val Met
                    675                 680                 685

Asp Asp Phe Ala Ala Phe Val Glu Lys Cys Cys Lys Ala Asp Asp Lys
690                 695                 700

Glu Thr Cys Phe Ala Glu Glu Gly Lys Lys Leu Val Ala Ala Ser Gln
705                 710                 715                 720

Ala Ala Leu Gly Leu Ser Gly Gly Gly Ser Gly Gly Gly Gly Ser
                    725                 730                 735

Gly Gly Gly Gly Ser Lys Ala Met His Val Ala Gln Pro Ala Val Val
                740                 745                 750

Leu Ala Ser Ser Arg Gly Ile Ala Ser Phe Val Cys Glu Tyr Ala Ser
                755                 760                 765

Pro Gly Lys Ala Thr Glu Val Arg Val Thr Val Leu Arg Gln Ala Asp
                770                 775                 780

Ser Gln Val Thr Glu Val Cys Ala Ala Thr Tyr Met Met Gly Asn Glu
785                 790                 795                 800

Leu Thr Phe Leu Asp Asp Ser Ile Cys Thr Gly Thr Ser Ser Gly Asn
                    805                 810                 815

Gln Val Asn Leu Thr Ile Gln Gly Leu Arg Ala Met Asp Thr Gly Leu
                    820                 825                 830

Tyr Ile Cys Lys Val Glu Leu Met Tyr Pro Pro Pro Tyr Tyr Leu Gly
                    835                 840                 845

Ile Gly Asn Gly Thr Gln Ile Tyr Val Ile Asp Pro Glu Pro Ser Pro
                    850                 855                 860

Asp Ser Ala Ala Ala His His His His His
865                 870                 875

<210> SEQ ID NO 29
<211> LENGTH: 736
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

-continued

```
Glu Arg Asn Glu Cys Phe Leu Gln His Lys Asp Asp Asn Pro Asn Leu
             100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
```

-continued

|  |  | 515 |  |  |  | 520 |  |  |  | 525 |  |
| --- | --- | --- | --- | --- | --- | --- | --- | --- | --- | --- | --- |

Leu Val Glu Leu Val Lys His Lys Pro Lys Ala Thr Lys Glu Gln Leu
530 535 540

Lys Ala Val Met Asp Asp Phe Ala Ala Phe Val Glu Lys Cys Cys Lys
545 550 555 560

Ala Asp Asp Lys Glu Thr Cys Phe Ala Glu Glu Gly Lys Lys Leu Val
565 570 575

Ala Ala Ser Gln Ala Ala Leu Gly Leu Ser Gly Gly Gly Ser Gly
580 585 590

Gly Gly Gly Ser Gly Gly Gly Ser Lys Ala Met His Val Ala Gln
595 600 605

Pro Ala Val Val Leu Ala Ser Ser Arg Gly Ile Ala Ser Phe Val Cys
610 615 620

Glu Tyr Leu Leu Asp Ile Glu Pro Glu Phe Val Arg Val Thr Val Leu
625 630 635 640

Arg Gln Ala Asp Ser Gln Val Thr Glu Val Cys Ala Ala Thr Tyr Gln
645 650 655

Leu Gln Trp Met Leu Thr Phe Leu Asp Asp Ser Ile Cys Thr Gly Thr
660 665 670

Ser Ser Gly Asn Gln Val Asn Leu Thr Ile Gln Gly Leu Arg Ala Met
675 680 685

Asp Thr Gly Leu Tyr Ile Cys Lys Val Glu Trp Ser Arg Glu Trp Gly
690 695 700

Arg Gln Gly Leu Gly Ile Gly Asn Gly Thr Gln Ile Tyr Val Ile Asp
705 710 715 720

Pro Glu Pro Ser Pro Asp Ser Ala Ala Ala His His His His His His
725 730 735

```
<210> SEQ ID NO 30
<211> LENGTH: 464
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: BDM scaffold sequence
<220> FEATURE:
<221> NAME/KEY: modified_base
<222> LOCATION: (85)..(129)
<223> OTHER INFORMATION: a, c, t or g
<220> FEATURE:
<221> NAME/KEY: misc_feature
<222> LOCATION: (85)..(129)
<223> OTHER INFORMATION: This region may encompass 15-45 nucleotides
<220> FEATURE:
<221> NAME/KEY: modified_base
<222> LOCATION: (193)..(237)
<223> OTHER INFORMATION: a, c, t or g
<220> FEATURE:
<221> NAME/KEY: misc_feature
<222> LOCATION: (193)..(237)
<223> OTHER INFORMATION: This region may encompass 15-45 nucleotides
<220> FEATURE:
<221> NAME/KEY: modified_base
<222> LOCATION: (349)..(393)
<223> OTHER INFORMATION: a, c, t or g
<220> FEATURE:
<221> NAME/KEY: misc_feature
<222> LOCATION: (349)..(393)
<223> OTHER INFORMATION: This region may encompass 15-45 nucleotides
<220> FEATURE:
<223> OTHER INFORMATION: See specification as filed for detailed
      description of substitutions and preferred embodiments
```

<400> SEQUENCE: 30

```
gccatggcaa aagcaatgca tgttgcacag cctgcagttg ttctggcaag cagccgtggt    60
attgccagct ttgtttgtga gtatnnnnnn nnnnnnnnnn nnnnnnnnnn nnnnnnnnnn   120
nnnnnnnnng tgcgcgtgac cgttctgcgt caggcagata gccaggttac cgaagtttgt   180
gcagcaacct atnnnnnnnn nnnnnnnnnn nnnnnnnnnn nnnnnnnnnn nnnnnnctg    240
acctttctgg atgatagcat ttgtaccggc accagcagcg gtaatcaggt taatctgacc   300
attcagggtc tgcgtgcaat ggataccggt ctgtatattt gcaaagttnn nnnnnnnnnn   360
nnnnnnnnnn nnnnnnnnnn nnnnnnnnnn nnnctgggca ttggcaatgg cacccagatt   420
tatgttattg atcctgaacc gtcaccggat agcaatgcgg ccgc                    464
```

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 31

His His His His His His
1               5

<210> SEQ ID NO 32
<211> LENGTH: 7
<212> TYPE: PRT
<213> ORGANISM: Homo sapiens

<400> SEQUENCE: 32

Met Tyr Pro Pro Pro Tyr Tyr
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly Gly Ser
1               5

<210> SEQ ID NO 34
<211> LENGTH: 6
<212> TYPE: PRT
<213> ORGANISM: Homo sapiens

<400> SEQUENCE: 34

Met Tyr Pro Pro Pro Tyr
1               5

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)

```
<223> OTHER INFORMATION: This sequence may encompass 3-6 "Gly Gly Gly
      Gly Ser" repeating units

<400> SEQUENCE: 35

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: SITE
<222> LOCATION: (1)..(30)
<223> OTHER INFORMATION: This region may encompass 3-6 "Ser Gly Gly Gly
      Gly" repeating units

<400> SEQUENCE: 36

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser
            20                  25                  30

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Ser Thr Val Ala Ala Pro Ser
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Val Ala Ala Pro Ser Gly Ser
1               5

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ser Thr Val Ala Ala Pro Ser Gly Ser
1               5                   10

<210> SEQ ID NO 40
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 40

Thr Val Ser Asp Val Pro Gly Ser
1               5

<210> SEQ ID NO 41
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Val Ser Asp Val Pro Thr Val Ser Asp Val Pro Gly Ser
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Val Ser Asp Val Pro Thr Val Ser Asp Val Pro
1               5                   10

<210> SEQ ID NO 43
<211> LENGTH: 12
<212> TYPE: PRT
<213> ORGANISM: Homo sapiens

<400> SEQUENCE: 43

Pro Glu Pro Cys Pro Asp Ser Asp Gly Ser Thr Gly
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Pro Glu Pro Ser Pro Asp Ser Asn
1               5
```

MULTI-SPECIFIC MOLECULES

FIELD OF THE DISCLOSURE

The present disclosure relates to multi-specific molecules which are capable of simultaneously binding at least two different target antigens or epitopes. The molecules comprise at least one binding domain molecule (BDM) which binds to a first target antigen or epitope, the BDM being modified for selective binding to a heterologous target, coupled to a pharmacologically active protein or peptide which is an antibody or antigen-binding fragment thereof or a non-antibody protein or peptide which binds to a second target antigen or epitope, the BDMs being coupled to a C-terminus of a polypeptide present within the pharmacologically active protein or peptide.

INCORPORATION BY REFERENCE

All documents cited or referenced herein, and all documents cited or referenced in herein cited documents, together with any manufacturer's instructions, descriptions, product specifications, and product sheets for any products mentioned herein or in any document incorporated by reference herein, are hereby incorporated herein by reference in their entirety.

This application claims priority from Australian Patent Application No. 2016900708 and Australian Patent Application No. 2016900709, the entire contents of which are herein incorporated by reference.

REFERENCE TO SEQUENCE LISTING

The entire content of the electronic submission of the sequence listing is incorporated by reference in its entirety for all purposes. The instant application contains a Sequence Listing which has been submitted electronically in ASCII format and is hereby incorporated by reference in its entirety. Said ASCII copy, created on Aug. 6, 2021, is named 9008-IMUN-001US-CON2_SL.txt and is 70,545 bytes in size.

BACKGROUND OF THE DISCLOSURE

A number of recombinant proteins have been developed as therapeutic agents. However, proteins in their unmodified form are known to be rapidly removed in vivo either by renal filtration, cellular clearance mechanisms in the reticulendothelial system, or proteolytic degradation (Francis (1992) Focus on Growth Factors 3:4-11). Various modifications of proteins and peptides have been developed to increase the therapeutic protein's stability, circulation time and biological activity (see Francis (1992) Focus on Growth Factors 3:4-10). However, there exists a need in the art for mechanisms which allow such therapeutic proteins to subsist in vivo for longer.

Therapeutic monoclonal antibodies and antibody-related products such as antibody-fusion proteins, antibody fragments, and antibody-drug conjugates (collectively referred to hereafter as antibody products) have grown to become the dominant product class within the biopharmaceutical market. Antibody products today are approved for the treatment of a variety of diseases, including some cancers, multiple sclerosis, asthma and rheumatoid arthritis to name but a few.

Notwithstanding this recent unparalleled success of the antibody drug development field, a lack of efficacy against certain disease targets has prompted the search for new strategies to develop more efficacious antibody drugs. One approach used to improve the efficacy of antibodies is to develop antibody-like protein structures that bind to two targets simultaneously; i.e. bi-specifics. A normal antibody can only bind one specific target (i.e. it has one specificity). A bi-specific is generally an engineered protein that is composed of two different antibodies or antibody-like fragments (known as antibody-like scaffolds) that are fused together so that the bi-specific can bind to two different types of targets at the same time (i.e. two specificities). The majority of antibody like scaffolds are generally constructed from fragments of antibodies or made from antibody like proteins that, like antibodies, can bind to specific targets. Dual specificity antibodies allow for more potent antibody drugs which can be designed to redirect and activate immune effector cells such as T-cells to specifically kill tumours; bind to multiple targets and effect multiple pathogenic pathways; bind to multiple sites on the one target cell or protein to increase specificity or induce synergistic induction; and target tumours that are heterogeneous in nature.

Currently, an important differentiator with existing technologies being implemented to generate bi-specific antibody products is the general approach of fusing various antibody-like scaffolds together to generate bi-specifics. This type of bi-specific has a number of significant drawbacks: Firstly, the small size of bi-specifics created by fusing two or more antibody-like scaffolds together, are generally significantly below the renal threshold and typically show very short blood circulation half-life which is in the range of minutes to hours. Such a short half-life necessitates dosing intervals of every day or via constant infusion which can lead to exceeding the toxicity threshold of the drug. And secondly, the affinity of many antibody-like scaffolds for their target is inadequate due to their monovalent nature (i.e. they have only one antigen binding site compared to antibodies which have two). Full antibodies bind with both antigen binding sites improving the overall strength of binding (knows as an avidity effect) giving a certain advantage compared with monovalent antibody-like scaffolds.

At present there are only a limited number of approaches that can generate bi-specific antibody products in a whole IgG format. Generally these approaches engineer the antibody backbone to allow two different parental antibodies with different specificities to come together to form a single IgG with arms that bind different targets (i.e. Catumaxomab). This whole antibody approach has certain advantages over the fusion of smaller fragments, however, while this type of whole IgG bi-specific approach circumvents the half-life issue seen with the small fragment bi-specifics, it does not address the loss of avidity as only one arm of the bi-specific binds to each target.

There is thus a need in the art for approaches which improve existing therapeutic proteins and antigen-binding molecules that assist in improving the therapeutic efficacy and/or half-life of such molecules. Additionally, there is a need in the art for approaches that overcome the shortcomings seen with current bi-specific antibody approaches and their use.

SUMMARY OF THE DISCLOSURE

The present disclosure is based on approaches to improve one or more characteristics of a protein or peptide, including an antibody or an immunoglobulin antigen-binding fragment. More particularly, the present disclosure is based on approaches that improve a poorly therapeutic protein (e.g. therapeutic antibody) by converting it into a multi-specific format. Coupling the protein or peptide to at least one binding domain molecule (BDM) described herein provides a bi-specific or multi-specific molecule thus allowing the molecule to bind to different targets by virtue of exploiting the different binding targets (i.e. antigens or epitopes) of the protein and the BDM. Accordingly, one or more characteristics of the protein or peptide can be improved including therapeutic efficacy, half-life, immune engagement, avidity, cellular penetration and/or tolerability. The molecules thus provide an alternative to traditional bi-specific antibodies.

Preferably, the target antigen or epitope bound by the BDM is different to the target antigen or epitope bound by the protein or peptide. For example, the protein may bind to a target antigen or epitope present on a cell or tissue and the BDM may bind to a target antigen or epitope present on an immune-modulating cell such as a cytotoxic T cell or protein to facilitate cell killing, or a target antigen on human serum albumin (HSA) so that the half-life of the protein or peptide may be extended.

By exploiting the simultaneous binding of the protein or peptide and the BDM to their targets, the therapeutic efficacy of the protein or peptide can be promoted by utilising the functionality of the target to which the BDM binds. By coupling further BDMs to the protein or peptide, the protein or peptide can be converted into bi-specific, tri-specifics or even multi-specifics. In particular, the smaller size, binding affinity characteristics and solubility of the BDMs make them ideal agents for improving the efficacy of poorly therapeutic proteins or peptides, for example, facilitating the body's natural immunological mechanism for destroying tumour cells.

The present disclosure thus provides a multi-specific molecule capable of binding to two or more different target antigens or epitopes, the molecule comprising:

(i) at least one binding domain molecule (BDM) which binds to a first target antigen or epitope, the BDM comprising or consisting of a V-like domain (VLD) scaffold having three exposed binding loops (BLs) contained within and wherein at least two of the three BLs are modified or replaced relative to their corresponding native sequence in the scaffold for selective binding to a heterologous target antigen or epitope; and (ii) a pharmacologically active protein or peptide which is an antibody or antigen-biding fragment thereof or a non-antibody protein or peptide which binds to a second target antigen or epitope;

wherein the at least one BDM is coupled to a C-terminus of a polypeptide present within the pharmacologically active protein or peptide.

In one example, the pharmacologically active protein binds to its native target antigen or epitope.

Preferably, the epitopes are on separate antigens.

In one example, the first and second target antigens are different. In one example, the first and second target antigens are the same but the molecule binds to different epitopes on the target antigen. In one example, the first and second target epitopes are different.

In one example, the molecule is a bi-specific. In one example, the molecule is a tri-specific.

In one example, the molecule comprises one, two, three, four or five BDMs (or multiples thereof e.g. BDM dimers). In another example, the molecule comprises one pair or two pairs of BDMs, wherein the BDMs in the pair are identical. In one example, one, two or three BDMs (or multiples thereof e.g. dimers) are coupled to the non-antibody protein or peptide.

In one example, the molecule comprises least two BDMs, or at least one pair of BDMs, wherein each BDM (or BDM pair) binds to a different target antigen or epitope. In a further example, each BDM (or BDM pair) binds to a target antigen or epitope that is different from the target antigen or epitope to which the pharmacologically active protein or peptide binds.

In another example, two, four, six, or eight BDMs are coupled to the full length antibody, wherein the molecule binds to at least two different target antigens or epitopes. In one example, the molecule binds to two different target antigens or epitopes. In another example, the molecule binds to three different target antigens or epitopes. In another example, the molecule binds to four different target antigens or epitopes.

In one example, the pharmaceutically active protein is a full length antibody or an immunoglobulin antigen-binding fragment thereof. In another example, the protein is a non-antibody protein or peptide.

In one example, the non-antibody protein or peptide is selected from the group consisting of a blood clotting factor, an anticalin, a toxoid, a collagen binding protein, a human serum binding protein (e.g. Human serum albumin, HSA) a tumour necrosis factor (TNF)-alpha receptor binding protein, an integrin binding protein, a vascular endothelial growth factor (VEGF) or mimetic thereof, an erythropoietin (EPO) or mimetic thereof, a C4 binding protein, a urokinase receptor antagonist, a lymphokine, a cytokine, an osteoprotegerin (OPG), or the extracellular domain of a protein selected from programmed cell death 1 protein (PD1), programmed death ligand 1 (PD-L1), NKG2D, MHC class I polypeptide related sequence A (MICA), MHC class I polypeptide related sequence B (MICB), UL16 binding protein (ULBP).

In one example, the blood clotting factor is factor VIII or factor IX.

In one example, the toxoid is botulinum toxoid.

In one example, the lymphokine is IL-2 or mimetic thereof or GM-CSF or mimetic thereof.

In one example, the cytokine is a G-CSF or mimetic thereof or stem cell factor (SCF) or a mimetic thereof.

In one example, the molecule comprises one BDM coupled to the non-antibody protein. In one example, the ratio of BDM to non-antibody protein is 1:1.

In one example, the at least one BDM is coupled to a C-terminus of an antibody heavy chain polypeptide. In one example, the at least one BDM is coupled to a C-terminus of both antibody heavy chain polypeptides.

In one example, the at least one BDM is coupled to a C-terminus of an antibody light chain polypeptide. In one example, the at least one BDM is coupled to a C-terminus of both antibody light chain polypeptides.

In one example, the at least one BDM is coupled to a C-terminus of all antibody heavy and light chain polypeptides.

In one example, the at least one BDM is coupled to a C-terminus of the CH1, CH2 or CH3 domain of an antibody heavy chain polypeptide.

In one example, the at least one BDM is coupled to a C-terminus of an antibody Fc.

In one example, at least one BDM is coupled to:
(i) the C-terminus of an antibody light chain polypeptide;
(ii) the C-terminus of each antibody light chain polypeptide;
(iii) the C-terminus of an antibody heavy chain polypeptide;

(iv) the C-terminus of each antibody heavy chain polypeptide.

The full length antibody or immunoglobulin antigen-binding fragment according to the present disclosure may itself be mono-specific or bi-specific. In the case of a mono-specific antibody, it is meant that the antibody binds to a single target or epitope through complementarity heavy and light chain variable domains (i.e. a pair of $V_H/V_L$) which share the same specificity for the target antigen or epitope. Bi-specific antibodies comprise one $V_H/V_L$ pair on each arm of the Y shaped antibody molecule, wherein each $V_H/V_L$ binds to a different target antigen or epitope.

A full length antibody comprises two heavy chains and two light chains, each forming a pair. Accordingly, in one example, the ratio of antibody chains to BDMs is 4:2. In one example, the molecule comprises four BDMs coupled to an antibody (i.e. one BDM on each light chain and one BDM on each heavy chain). In one example, the ratio of antibody chains to BDMs is 4:4. In one example, the molecule comprises six BDMs coupled to an antibody. In one example, the ratio of antibody chains to BDM is 4:6. In another example, the molecule comprises eight BDM coupled to an antibody. In another example, the ratio of antibody chains to BDM is 4:8. In another example, the ratio of antibody chains to BDMs is 4:2$n$ wherein n is a number between 1 and 5, including 1 and 5.

In one example, the immunoglobulin antigen-binding fragment is selected from the group consisting of Fab, F(ab')$_2$, Fab', scFv, di-scFv, or chemically linked F(ab')$_2$.

In one example, the molecule comprises a single BDM coupled to an immunoglobulin antigen-binding fragment. In one example, the ratio of immunoglobulin antigen binding fragment chains to BDM is 2:1. In one example, the ratio of immunoglobulin antigen-binding fragment chains to BDM is 2:2. In another example, a chain of BDMs may be coupled to the antigen-binding fragment wherein the ratio of immunoglobulin antigen binding fragment chains to BDM is 2:n wherein n is number between 1 and 16. In another example, n is a number between 1 and 14, between 1 and 12, between 1 and 10, between 1 and 8, between 1 and 4, or 2, or 1.

The present disclosure contemplates a number of different configurations in which the at least one BDM may be coupled to a full length antibody, for example:

(i) at least one BDM is coupled to a C-terminus of a CH3 domain of a heavy chain polypeptide of an antibody;

(ii) at least one BDM is coupled to a C-terminus of a CH1 domain of a light chain polypeptide;

(iii) at least one BDM is coupled to a C-terminus of a CH3 domain of a heavy chain polypeptide and to a C-terminus of a CH1 domain of a light chain polypeptide;

(iv) at least one BDM is coupled to the C-terminus of a CH3 domain of both heavy chain polypeptides; or (v) at least one BDM is coupled to the C-terminus of a CH1 domain of both light chain polypeptides.

With respect to an immunoglobulin antigen-binding fragment, an BDM may be coupled to a C-terminus of either the heavy or light chain of the immunoglobulin fragment. In another example, an BDM may be coupled to a C-terminus of both the heavy and light chains of the immunoglobulin fragment. In another example, the BDM may be coupled to a constant domain (e.g. CH1) of either the light and/or heavy chains of the immunoglobulin fragment (e.g. Fab).

For example:

(i) at least one BDM is coupled to a C-terminus of the constant region of a light chain polypeptide of an Fab;

(ii) at least one BDM is coupled to a C-terminus of the CH1 of the heavy chain polypeptide of an Fab; or (iii) at least one BDM is coupled to a C-terminus of the constant region of the light chain polypeptide and a C-terminus of the CH1 of the heavy chain polypeptide of an Fab.

The BDM according to the present disclosure preferably comprises or consists of a scaffold having three exposed binding loops (BLs) contained within. The scaffold may be selected from the group consisting of an immunoglobulin-like (Ig-like) domain containing superfamily member, a V-like domain, an i-body, VNAR or VHH.

In one example, the exposed BL sequences are modified or replaced from the native BL sequences to provide altered binding loops with selective binding to a heterologous target antigen or epitope. These binding loops are designated BL1, BL2 and BL3 respectively as illustrated in FIG. 1A. The BLs are analogous to the CDR1, CDR2 and CDR3 regions of an antibody variable region.

In one example, BL1 and BL3 are modified or replaced from the native BL sequence. In another example, BL1, BL2 and BL3 are modified or replaced from the native BL sequence.

In another example, the BDM scaffold has less than about 20% sequence identity to a human immunoglobulin variable region domain, said scaffold having two or more altered BLs and exhibiting selective binding to a heterologous target antigen or epitope.

The Ig-like domain containing superfamily member may be selected from the group consisting of a V-like domain (VLD), C-set domain, a ThyOx family member polypeptide, a T cell receptor, CD2, CD4, CD8, class I MHC, class II MHC, CD1, cytokine receptor, G-CSF receptor, GM-CSF receptor, hormone receptors, growth hormone receptor, erythropoietin receptor, interferon gamma receptor, prolactin receptor, NCAM, VCAM, ICAM, N-caderin, E-caderin, fibronectin, tenascin, and I-set containing domain polypeptides or a functional fragment thereof.

The BDM scaffold according to the present disclosure may be selected from the group consisting of V-like domain (VLD), a C1 set domain or C2 set domain. Combinations of BDMs coupled to the protein or peptide are also contemplated. By way of illustration, one BDM may be a VLD and another BDM may be C set domain.

In one example, the BDM scaffold comprises or consists of the extracellular portion of a native VLD, or a VLD having altered binding loops (i.e. modified BDM) relative to the native VLD, wherein the VLD is from a protein selected from the group consisting of ACAN, ADORA3, ALCAM, JAML, AMIGO1, AXL, basigin, BCAM, BTNL2, 3, 8, 9 or 10, butyrophilin (BTN), cell adhesion molecule (CAM), CD2, CD4, CD7, CD8, CD28, CD33, CD48, CD79, CD80, CD83, CD86, CD101, CD112, CD226, CD274, CD276, CD300, carcinoembryonic antigen-related cell adhesion molecule (CEACAM), CRTAM, CTLA4, CXADR, C10orf54, ERMAP, ESAM, FAM187A, FCAMR, F11R, GPA33, Hyaluronan and proteoglycan link protein (HAPLN), HAVCR1, HEPACAM, HHLA2, HSPG2, ICOS, IGHA, IGSF, JAM2, JAM3, KDR, KIRREL, LY6G6F, MCAM, MOG, MPZ, MXRA8, NCA, NCR2, NCR3, NPHS1, PD1, PDCD1, PIGR, PILR, PSG, PTGFRN, PVR, Sodium channel subunit proteins (SCN), SEMA3D, Sioadhesin proteins (SIGLEC), signal regulatory proteins (SIRP), SLAMF6, SLAMF7, TIGIT, TIMD4, TREM, TREML, VCAN, VPREB, VSIG, VSTM, and VTCN1.

In one example, the BDM scaffold comprises or consists of the extracellular portion of a native C-set domain (C1-set or C2-set domain), or a C-set domain having altered binding loops (i.e. modified C-set domain) relative to the native C-set domain, wherein the C-set domain is from a protein selected from the group consisting of AZGP1; basigin, B2M; CEACAM1, 3, 4, 5, 6, 7, 8; CD1A; CD1B; CD1C; CD1D; CD1E; DMA; DQB2; DRB1; ELK2P1; FCGRT; HFE; HHLA2; HLA-A; HLA-B; HLA-B35; HLA-B57; HLA-C; HLA-CW; HLA-Cw; HLA-D; HLA-DMA; HLA-DMB; HLA-DOA; HLA-DOB; HLA-DP; HLA-DPA1; HLA-DPB1; HLA-DQA1; HLA-DQA2; HLA-DQB1; HLA-DQB2; HLA-DRA; HLA-DRB1; HLA-DRB2; HLA-DRB3; HLA-DRB4; HLA-DRw12; HLA-Dw12; HLA-E; HLA-F; HLA-G; HLA-G2.2; HLA-H; HLAC; IGHA1; IGHA2; IGHD; IGHE; IGHG1; IGHG2; IGHG3; IGHG4; IGHM; IGHV4-31; IGKC; IGKV1-5; IGKV2-24; IGL@; IGLC1; IGLC3; IGLL1; IGLV2-14; IGLV3-21; IGLV3-25; IGLV4-3; MICA; MICB; MR1; SIRPA; SIRPB1; SIRPG; SNC73; TAPBP; TAPBPL; TRBC1; TRBV19; TRBV21-1; TRBV3-1; TRBV5-4; TRBV7-2; micB, CD2, CD4, CD80, VCAM and ICAM.

In one example, the BDM scaffold comprises or consists of the whole or part thereof of a native Ig-like domain or an Ig-like domain with altered binding loops (i.e. modified Ig-like domain) relative to the native Ig-like domain, wherein the Ig-like domain is selected from the group consisting of a ThyOx family member polypeptide, a T cell receptor, CD2, CD4, CD8, class I MHC, class II MHC, CD1, cytokine receptor, G-CSF receptor, GM-CSF receptor, hormone receptors, growth hormone receptor, erythropoietin receptor, interferon gamma receptor, prolactin receptor, NCAM, VCAM, ICAM, N-caderin, E-caderin, fibronectin, tenascin, and I-set containing domain polypeptides or a functional fragment thereof.

The term "modified VLD", "modified C-set domain" etc. as referred to herein refers to a BDM in which at least two, and preferably all three of the exposed binding loops are altered to provide binding to a heterologous target antigen or epitope. The alteration may be achieved by amino acid substitution or replacement of the whole or part thereof of individual binding loops. The altered amino acid sequences in the binding loops confers selective binding activity towards a target antigen other than that bound by the unaltered Ig-like domain containing scaffold. The amino acid alterations can be made at the nucleic acid or polypeptide level using methods known in the art.

A VLD or C-set domain may encompass a BDM which binds to a heterologous target antigen or epitope. A modified VLD or C-set domain may also comprise one or more modifications which alter the affinity of the BDM to its native target. The affinity towards the native target may be increased or decreased compared to the native VLD or C-set domain.

In one example, the modified BDM comprises or consists of a sequence at least about 60%, 70%, 75%, 80%, 85%, 87%, 90%, or 95% identical to the sequence of a native VLD or C-set domain.

Persons skilled in the art will be familiar with selecting appropriate heterologous binding loop sequences to provide binding of the BDM to a desired target antigen. Such examples include those described in U.S. Pat. No. 7,166,697, the entire contents of which are incorporated by reference herein.

In another example, the BDM comprises or consists of the whole or part thereof of a VLD protein or C-set domain protein comprising between 5 and 30 amino acid substitutions, between 5 and 20 amino acid substitutions, between 5 and 15 amino acid substitutions, between 5 and 10 amino acid substitutions, or up to 5 amino acid substitutions compared to the corresponding native VLD or C-set domain protein. In another example, the BDM is not the CLTA-4 VLD mutant molecule L104EA29Y or L104E described in U.S. Pat. No. 7,094,874.

In certain examples, the modified BDM comprises one heterologous BL sequence. In another example, the modified BDM comprises two heterologous BL sequences. In yet another example, the BDM comprises three heterologous BL sequences.

In particular examples, the BDM is a VLD scaffold comprising or consisting of the extracellular portion of CTLA4, CD28 or ICOS. In a further example, the VLD scaffold is the extracellular portion of human CTLA4. In another example, the BDM VLD comprises or consist of the sequence set forth in

```
                                          (SEQ ID NO: 1)
KAMHVAQPAVVLASSRGIASFVCEYASPGKATEVRVTVLRQADSQVTEV

CAATYMMGNELTFLDDSICTGTSSGNQVNLTIQGLRAMDTGLYICKVEL

MYPPPYYLGIGNGTQIYVIDPEPSPDSN.
```

In one example, the alanine (A) at position 31 is substituted with tyrosine (Y). In one example, the methionine (M) at position 56 is replaced with a threonine (T).

In another example, the BDM VLD scaffold consists of a framework sequence corresponding to residues 1 to 25, 34 to 54, 60 to 96 and 106 to 126 of SEQ ID NO:1.

In another example, the BDM scaffold comprises or consists of a sequence having at least about 70% sequence identity thereto, or at least 75%, 80%, 85%, 87%, 90%, 92%, 93%, 94%, 95%, 96%, 97% 98% or 99% identity to SEQ ID NO:1 or to residues 1 to 25, 34 to 54 and 60-107 and 116 to 136 of SEQ ID NO:1.

In another example a single exposed binding loop, two exposed binding loops or all three exposed binding loops of the native BDM scaffold may be modified by amino acid substitution, addition or deletion, and/or by any change to one or more physical characteristics (e.g. size, shape, charge, hydrophobicity etc.).

In a further example, the exposed binding loop (BL1) sequence ASPGKATE (SEQ ID NO:2) or ASPGKYTE (SEQ ID NO:7), and/or exposed loop (BL2) sequence MMGNE (SEQ ID NO:3) and/or the exposed binding loop (BL3) sequence ELMYPPPYY (SEQ ID NO:4) of the native human CTLA-4 VLD sequence is modified by amino acid substitution, addition or deletion or replaced with a heterologous sequence.

In one example, the amino acid residues at positions 26 to 33, and/or positions 55 to 59 and/or positions 98 to 105 of SEQ ID NO:1 are modified or replaced.

In another example, the amino acid residues at positions 27 to 33, and/or positions 54 to 62 and/or positions 98 to 106 of SEQ ID NO:1 are modified or replaced with heterologous sequence.

In another example, the effect of modifying the native human CTLA-4 VLD is to abolish the natural affinity of the VLD to CD80 and CD86.

In one example, the BDM VLD scaffold comprises or consists of the sequence

```
                                          (SEQ ID NO: 5)
KAMHVAQPAVVLASSRGIASFVCEYXn₁VRVTVLRQADSQVTEVCAATY

Xn₂LTFLDDSICTGTSSGNQVNLTIQGLRAMDTGLYICKVXn₃LGIGNGT

QIYVIDPEPSPDSN
``` wherein X, X and X is any amino acid residue and n is a number between 5 and 15 and the numbers 1, 2 and 3 indicate the binding loop regions. More particularly, 1, 2 and 3 correspond to the BL-1, BL-2 and BL-3 respectively of the BDM.

In one example, the BDM VLD scaffold comprises or consists of the sequence (SEQ ID NO: 6)
KAMHVAQPAVVLASSRGIASFVCEY$Xn_1$EVRVTVLRQADSQVTEVCAATY $Xn_2$LTFLDDSICTGTSSGNQVNLTIQGLRAMDTGLYICKV$Xn_3$GIGNGTQ

IYVIDPEPSPDSN wherein X, X and X is any amino acid residue and n is a number between 5 and 15 and the numbers 1, 2, and 3 indicate the binding loop regions. More particularly, 1, 2 and 3 correspond to the BL-1, BL-2 and BL-3 respectively of the BDM.

In one example, the BL-1, BL-2 and BL-3 of the BDM comprise or consist of respectively ASPGKATE (SEQ ID NO:2) or ASPGKYTE (SEQ ID NO:7), MMGNE (SEQ ID NO:3) and ELMYPPPYYL (SEQ ID NO:9), wherein the BDM binds to B7-1.

In one example, the BL-1, BL-2 and BL-3 of the BDM of the molecule comprise or consist of respectively TVSWVDME (SEQ ID NO:10), WNGRW (SEQ ID NO:11) and QLDPSWGYYVVQGYE (SEQ ID NO:12), wherein the BDM binds to sclerostin.

In one example, the BDM VLD comprises or consists of the sequence (SEQ ID NO: 13)
KAMHVAQPAVVLASSRGIASFVCEYASPGKYTEVRVTVLRQADSQVTEVC

AATYMTGNELTFLDDSICTGTSSGNQVNLTIQGLRAMDTGLYICKVELMY

PPPYYLGIGNGTQIYVIDPEPSPDSN, wherein the BDM binds to B7-1.

In another example, the BDM VLD comprises or consists of the sequence (SEQ ID NO: 14)
KAMHVAQPAVVLASSRGIASFVCEYTVSWVDMEVRVTVLRQADSQVTEV

CAATYWNGRWLTFLDDSICTGTSSGNQVNLTIQGLRAMDTGLYICKVQL

DPSWGYYWQGYEGIGNGTQIYVIDPEPSPDSN, wherein the BDM binds to sclerostin.

In a further example, BL-1, BL-2 and BL-3 of the BDM are replaced with the CDR1, CDR2 and CDR3 sequences respectively of an antibody. The antibody from which the CDR sequences are derived may be derived from any species. In one example, the antibody is derived from a human. In another example, the antibody is derived from a domestic animal, for example, cat, dog, rabbit, guinea pig or horse.

In one example, the at least one BDM may be present in the molecule in monomeric form or dimeric form. In another example, the at least one BDM may consist of a series of BDM monomers linked together.

Accordingly, the term "BDM" as used herein in intended to include a BDM in monomeric form. In one example, the BDM is a dimer. The dimer may be formed through a disulphide bond between cysteine residues ($Cys^{120}$) in the stalks of the CTLA4 monomers (each stalk corresponding to about 10 residues connecting the VLD to the transmembrane region). Alternatively, the dimer may be formed by linking of monomeric units. In one example, a series (or daisy chain) of monomeric BDMs may be linked together. For example, between 2 and 16 BDM monomers may be joined head-to-tail in a daisy chain like arrangement. In another example, between 2 and 14, between 2 and 12, between 2 and 10, between 2 and 8, or between 2 and 4 BDMs are joined head to tail.

Linking of BDM monomers may be achieved for example by use of covalent or non-covalent bonds or by use of a short peptide linker as described further herein. Any of the linking methodologies referred to herein can be employed to link the BDM monomers together. Alternatively adjacent BDM monomers may be directly fused together.

In one example, the BDM is soluble. The 'solubility' of the BDM scaffold of the present disclosure correlates with the production of correctly folded, monomeric domains. The solubility may be assessed for example, by high performance liquid chromatography (HPLC). For example, soluble, monomeric BDMs will give rise to a single peak on the HPLC chromatograph, whereas insoluble (e.g. multimeric or aggregated) BDMs will give rise to a plurality of peaks.

Coupling of the at least one BDM and the pharmacologically active protein may be achieved by methods known to persons skilled in the art. Coupling may be achieved, for example, by use of a linker, by direct fusion, by conjugation or by covalent or non-covalent bonding.

In one example, coupling of the pharmacologically active protein and the at least one BDM is achieved by means of a peptide linker. Any suitable peptide linker known in the art can be utilised in the present disclosure. In one example, the linker comprises a sequence (SGGGG)$_n$S, (SEQ ID NO:15) wherein n is any number from 2 to 8, or from 3 to 6 or from 3 to 4. In one example, the linker comprises or consists of the sequence (SEQ ID NO: 16)
SGGGGSGGGGSGGGGS or (SEQ ID NO: 17)
SGGGGSGGGGSGGGGSGGGGS In another example, coupling of the pharmacologically active protein and the at least one BDM is achieved without use of a linker.

In one example, the molecule is capable of simultaneous binding to the first, second and/or optionally a third target antigen.

In another example, the molecule is capable of simultaneous binding to B7-1-Fc and sclerostin.

In a further example, the pharmacologically active protein or peptide and the at least one BDM specifically bind to their respective target antigens. In another example, the molecule binds selectively to cells that express two or more different target antigens or epitopes recognised by the individual BDM and pharmaceutically active protein moieties of the molecule but not to cells that express only one of the target antigens or epitopes.

The present disclosure also provides a polypeptide comprising a BDM scaffold coupled to a pharmacologically active protein or peptide. In one example, the polypeptide further comprises a linker. In one example, the linker comprises a sequence (SGGGG)nS (SEQ ID NO: 15), wherein n is any number from 2 to 8, or from 3 to 6 or from 3 to 4. In one example, the linker comprises or consists of the sequence

SGGGGSGGGGSGGGGS (SEQ ID NO: 16)

or

SGGGGSGGGGSGGGGSGGGGS. (SEQ ID NO: 17)

The present disclosure also provides a polypeptide selected from the group comprising or consisting of a sequence of any one of SEQ ID NOs: 5, 6, 13, 14, 19, 21, 22, 23, 24, 25, 27, 28 or 29. Preferably, the polypeptide is isolated. In one example, a polypeptide of the present disclosure includes a polypeptide tag. Examples, of suitable tags include, but are not limited to the p97 molecule, myc, hexa-his tag (SEQ ID NO: 31), flag, E7.

In one embodiment, the molecule according to the disclosure is a nucleic acid. The present disclosure also provides a nucleic acid encoding a polypeptide of the present disclosure, in particular a polypeptide of any one of SEQ ID NOs: 5, 6, 13, 19, 21, 22, 23, 24, 25, 27, 28 or 29. Nucleic acid can comprise DNA or RNA or both.

In one example, the molecule comprises or consists of the nucleic acid sequence of a BDM VLD set forth in:

(SEQ ID NO: 30)
GCCATGGCAAAAGCAATGCATGTTGCACAGCCTGCAGTTGTTCTGGCAA

GCAGCCGTGGTATTGCCAGCTTTGTTTGTGAGTATN1GTGCGCGTGACC

GTTCTGCGTCAGGCAGATAGCCAGGTTACCGAAGTTTGTGCAGCAACCT

ATN2CTGACCTTTCTGGATGATAGCATTTGTACCGGCACCAGCAGCGGT

AATCAGGTTAATCTGACCATTCAGGGTCTGCGTGCAATGGATACCGGTC

TGTATATTTGCAAAGTTN3CTGGGCATTGGCAATGGCACCCAGATTTAT

GTTATTGATCCTGAACCGTCACCGGATAGCAATGCGGCCGC wherein N1 is length of nucleotides encoding a first binding loop, N2 is a length of nucleotides encoding a second binding loop and N3 is a length of nucleotides encoding a third binding loop. In one example, N1, N2 and N2 are between 15 and 45 nucleotides. In one example, N1 is between 15 and 24 nucleotides. N2 is 15 nucleotides and N3 is between 30 and 45 nucleotides. N is any nucleotide (A, C, T, G).

In one example the nucleic acid is provided in an expression construct in which the nucleic acid is operably linked to a promoter. Such an expression construct can be in a vector e.g. a plasmid. In one example, the expression construct may be a bicistronic expression construct. The present disclosure also contemplates separate expression constructs for the heavy and light chains of the antibody or immunoglobulin antigen-binding fragment. For example, one vector may comprise a nucleic acid encoding the immunoglobulin light chain and a BDM VLD and the other which comprises a nucleic acid encoding the immunoglobulin heavy chain or vice versa.

The nucleic acid may further include a moiety e.g. FLAG to facilitate purification and identification. Systems for cloning and expression of a polypeptide in a variety of different host cells are known and as described further herein.

The present disclosure also provides a host cell transformed with a nucleic acid described herein. Suitable host cells include bacteria, mammalian cells, yeast, moss (bryophytes), and baculovirus systems.

The present disclosure also provides a method for producing the polypeptide molecule of the present disclosure comprising culturing the host cell of the present disclosure under conditions enabling expression of the polypeptide and optionally recovering the polypeptide. Depending upon the choice of host cell, the polypeptide may be glycosylated or unglycosylated.

The present disclosure also provides a method for making a multi-specific molecule comprising at least one BDM VLD coupled to a pharmacologically active protein, the method comprising:

(i) providing a nucleic acid encoding a BDM VLD sequence, wherein at least two of the three BLs of the VLD are modified or replaced with heterologous sequence;

(ii) providing a nucleic acid encoding a pharmacologically active protein or peptide; and (iii) optionally providing a nucleic acid encoding a linker sequence;

(iv) expressing the nucleic acid sequences in a suitable vector;

(v) recovering the expressed protein.

The present disclosure also provides a method or making a multi-specific molecule comprising at least one BDM VLD coupled to an antibody, the method comprising:

(i) providing a nucleic acid encoding an antibody light chain sequence or part thereof;

(ii) providing a nucleic acid encoding an antibody heavy chain sequence or part thereof;

(iii) providing a nucleic acid encoding a BDM VLD sequence, wherein at least two of the three BLs of the VLD are modified or replaced with heterologous sequence;

(iv) expressing the nucleic acid sequences in a suitable vector(s); and (v) recovering the expressed protein.

In one example according to the method, the antibody heavy chain consists of the full length sequence. In another example according to the method, the antibody heavy chain consists of the variable region and at least the CH1 region. In another example, the antibody heavy chain consists of the variable region and at least the CH1 and CH2 regions.

In one example according to the method no linker sequence is present and the nucleic acid sequences of the pharmacologically active protein or peptide and BDM VLD are contiguous. In another example, no linker sequence is present and the nucleic acid sequences encoding the antibody heavy and/or light chain and BDM sequences are contiguous.

The antibody nucleic acid sequence may further comprise the hinge region.

The present disclosure also provides a vector(s) comprising one or more nucleic acid sequences described herein. In one example, the vector comprises a nucleic acid sequence encoding a pharmacologically active protein as described herein and the BDM VLD and optionally a nucleic sequence encoding the linker. In one example, the vector(s) comprises a nucleic acid sequence encoding an antibody light or heavy chain as described herein and a nucleic acid sequence encoding an BDM VLD and optionally a nucleic acid sequence encoding the linker. In another example, the vector(s) comprises nucleic acid sequences encoding both the antibody heavy and light chains as described herein and a nucleic acid sequence encoding a BDM VLD and optionally a nucleic acid sequence encoding the linker.

The present disclosure also provides a host cell containing a vector or containing one or more nucleic acid sequences described herein.

The present disclosure also provides a multi-specific molecule produced by a method described herein.

The molecule of the present disclosure may be provided in a composition. Accordingly, in another embodiment, the present disclosure provides a pharmaceutical composition comprising the multi-specific molecule described herein, together with a pharmaceutically acceptable carrier and/or excipient. The composition may be provided as a medicament. In one example, the composition is for use in the treatment of a disorder. In another example, the composition is for anti-ageing or as a cosmetic.

In another example, the molecule may be labelled with an agent to facilitate detection. The composition of the present disclosure may also be provided in the form of a kit with instructions for use according to a particular treatment indication.

The present disclosure also provides use of the multi-specific molecule as described herein for detection of one or more target antigens to which one or more moieties of the molecule bind.

BRIEF DESCRIPTION OF THE DRAWINGS

FIG. 1 provides (A) a schematic of the sequence of the native human CTLA4 VLD scaffold showing where the framework sequences and the sequences of binding loops 1, 2 and 3 are located (designated as BL1, BL2 and BL3). B shows the location of the binding loop replacements in the CTLA4 VLD wherein BL1 is designated by $Xn_1$, BL2 is designated by $Xn_2$ and BL3 is designated by $Xn_3$ wherein X is any amino acid and n is a number between 5 and 15. C shows the sequence of the sclerostin human VLD scaffold wherein the sequence of the binding loop regions are underlined. FIG. 1C discloses SEQ ID NO: 14.

Tri-specific injected: Point at which the IgG VLDx4 (Scl-HC)(B7-LC) is added to the sensor surface. The trace shows the IgG VLDx4 (Scl-HC)(B7-LC) binding to lysozyme immobilised on the biosensor surface.

Buffer injected 1: Point at which the injection of IgG VLDx4 (Scl-HC)(B7-LC) is stopped and replaced with buffer. The trace shows the dissociation of the IgG VLDx4 (Scl-HC)(B7-LC) from the lysozyme immobilised on the biosensor surface.

B7-1-Fc injected: Point at which the second analyte B7-1-Fc is added. The trace shows B7-1-Fc binding to the IgG VLDx4 (Scl-HC)(B7-LC) that is still bound to the lysozyme immobilised on the biosensor surface.

Buffer injected 2: Point at which the injection of B7-1-Fc is stopped and replaced with buffer. The trace shows the dissociation of B7-1-Fc from IgG VLDx4 (Scl-HC)(B7-LC) still attached to the lysozyme immobilised on the biosensor surface Sclerostin injected: Point at which the third analyte sclerostin is added. The trace shows sclerostin binding to the IgG VLDx4 (Scl-HC)(B7-LC) that is still bound to the lysozyme immobilised on the biosensor surface while IgG VLDx4 (Scl-HC)(B7-LC) is simultaneously still binding B7-1-Fc.

Buffer injected 3: Point at which the injection of sclerostin is stopped and replaced with buffer. The trace shows the dissociation of sclerostin from IgG VLDx4 (Scl-HC)(B7-LC) still attached to the lysozyme immobilised on the biosensor surface.

Figure 23:
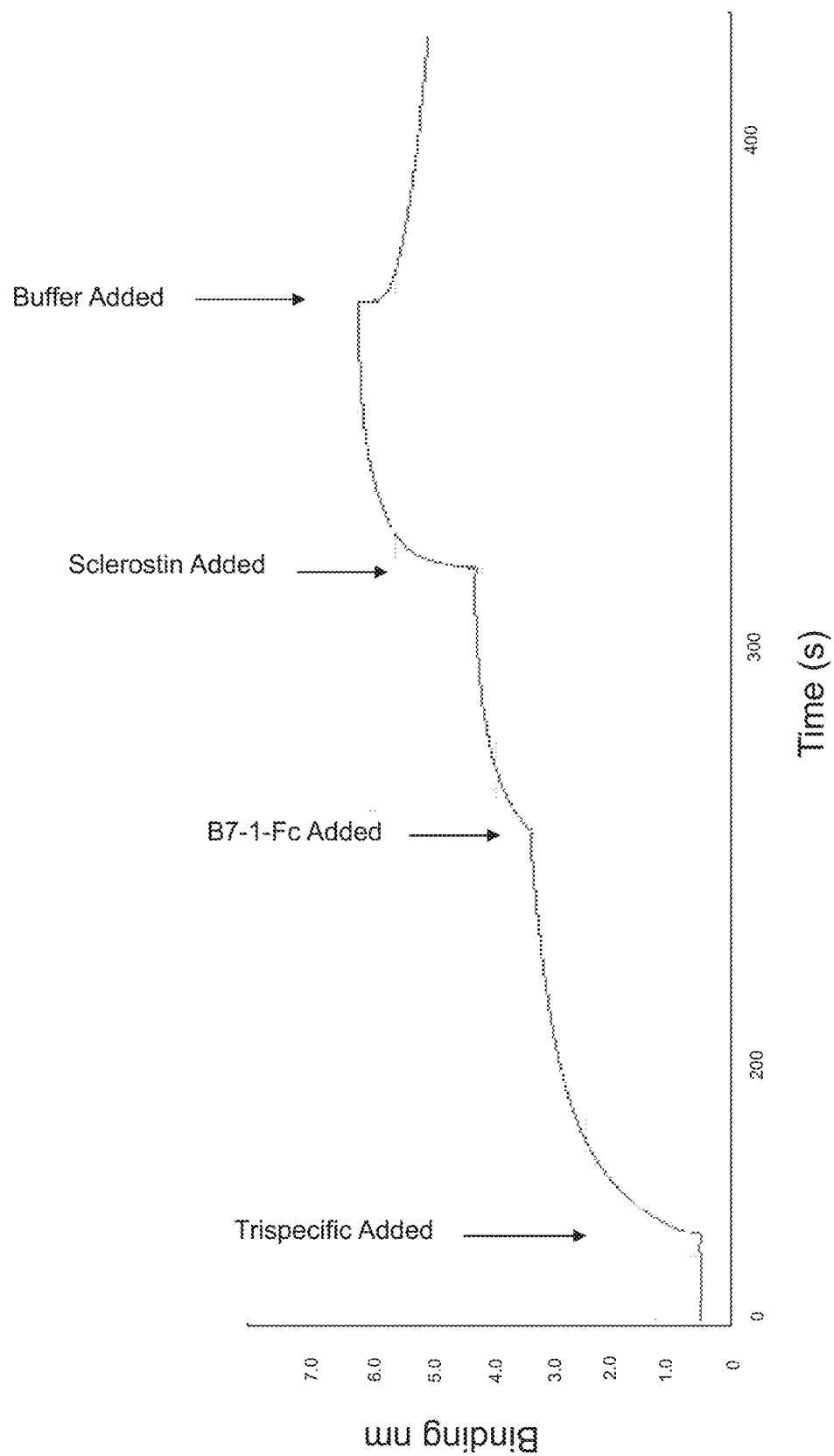

FIG. 23 shows BLitz® binding analysis demonstrating initial binding of the tri-specific [Fab VLDx2 (B7-HC)(Scl-LC)] to streptavidin captured biotin labelled lysozyme followed by sequential and simultaneous binding to B7-1-Fc and sclerostin. The tri-specific has a sclerostin binding VLD fused to the D1.3 Fab [D1.3 Fab] light chain and a B7-1 binding VLD fused to the heavy chain. The trace shows the tri-specific binding to lysozyme immobilised on the biosensor surface followed by the addition of B7-1-Fc. The binding trace demonstrates simultaneous, dual target binding to lysozyme and B7-1-Fc. Sclerostin is added to demonstrate simultaneous, tri-target binding to lysozyme and B7-1-Fc and sclerostin.

Tri-specific Added: Point at which the Fab VLDx2 (B7-I-HC)(Scl-LC) is added to the sensor surface. The trace shows the Fab VLDx2 (B7-I-HC)(Scl-LC) binding to lysozyme immobilised on the biosensor surface.

B7-1-Fc Added: Point at which B7-1-Fc is added. The trace shows B7-1-Fc binding to the Fab VLDx2 (B71-HC)(Scl-LC) that is still bound to the lysozyme immobilised on the biosensor surface.

Sclerostin Added: Point at which sclerostin is added. The trace shows sclerostin binding to the Fab VLDx2 (B71-HC)(Scl-LC) that is still bound to the lysozyme immobilised on the biosensor surface while Fab VLDx2 (B71-HC)(Scl-LC) is simultaneously still binding B7-1-Fc.

Buffer Added: Point at which sclerostin is replaced with buffer.

Figure 24:
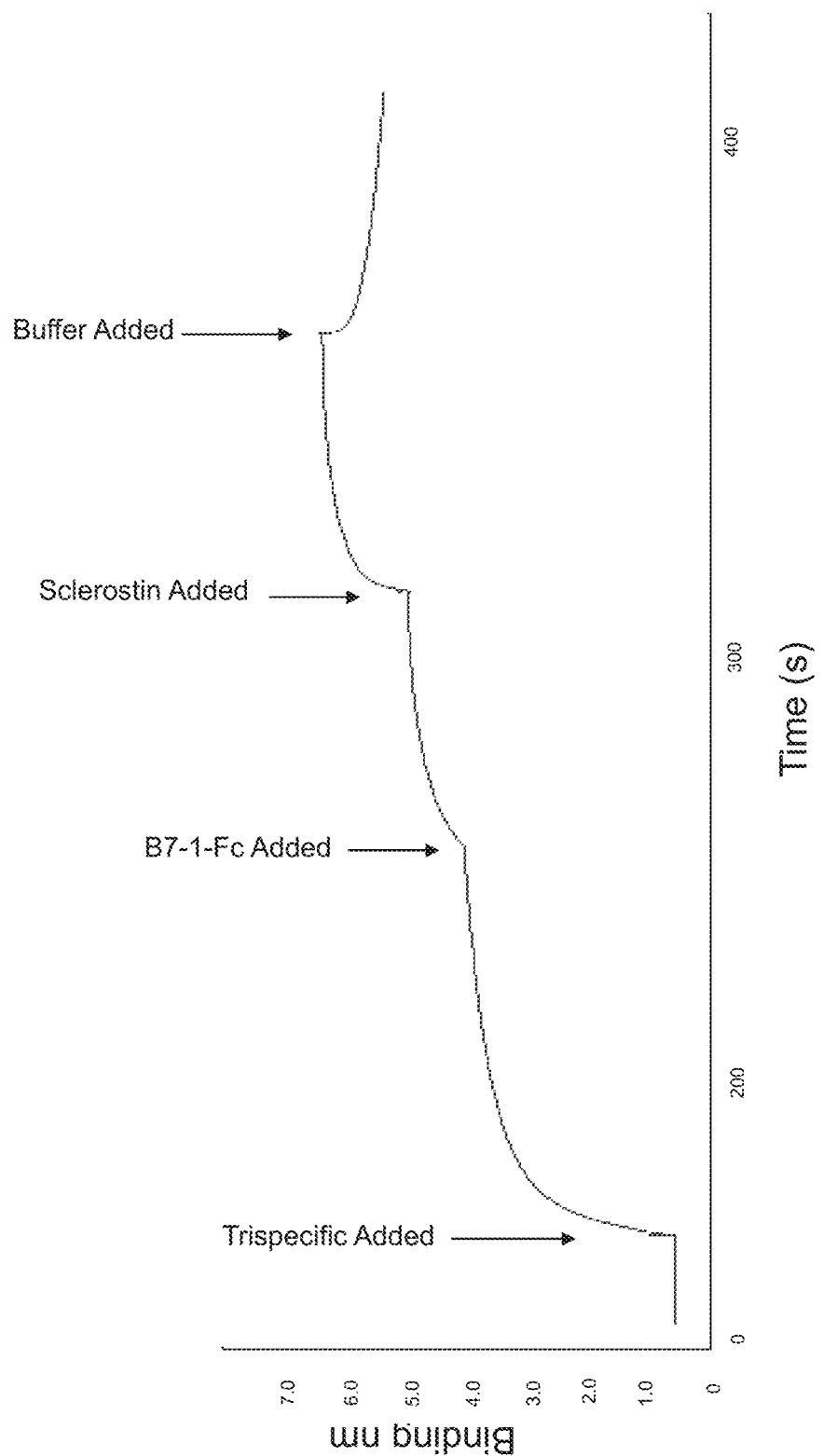

FIG. 24 shows BLitz® binding analysis demonstrating initial binding of the tri-specific [Fab VLDx2 (Scl-HC)(B7-LC)] to streptavidin captured biotin labelled lysozyme followed by sequential and simultaneous binding to B7-1-Fc and sclerostin. The tri-specific has a sclerostin binding VLD fused to the D1.3 Fab [D1.3 Fab] heavy chain and a B7-1 binding VLD fused to the light chain. The trace shows the tri-specific binding to lysozyme immobilised on the biosensor surface followed by the addition of B7-1-Fc. The binding trace demonstrates simultaneous, dual target binding to lysozyme and B7-1-Fc. Sclerostin is added to demonstrate simultaneous, tri-target binding to lysozyme and B7-1-Fc and sclerostin.

Tri-specific Added: Point at which the Fab VLDx2 (Scl-HC)(B7-LC) is added to the sensor surface. The trace shows the Fab VLDx2 (Scl-HC)(B7-LC) binding to lysozyme immobilised on the biosensor surface.

B7-1-Fc Added: Point at which B7-1-Fc is added. The trace shows B7-1-Fc binding to the Fab VLDx2 (Scl-HC)(B7-LC) that is still bound to the lysozyme immobilised on the biosensor surface.

Sclerostin Added: Point at which sclerostin is added. The trace shows sclerostin binding to the Fab VLDx2 (Scl-HC)(B7-LC) that is still bound to the lysozyme immobilised on the biosensor surface while Fab VLDx2 (Scl-HC)(B7-LC) is simultaneously still binding B7-1-Fc.

Buffer Added: Point at which sclerostin is replaced with buffer.

Figure 25:
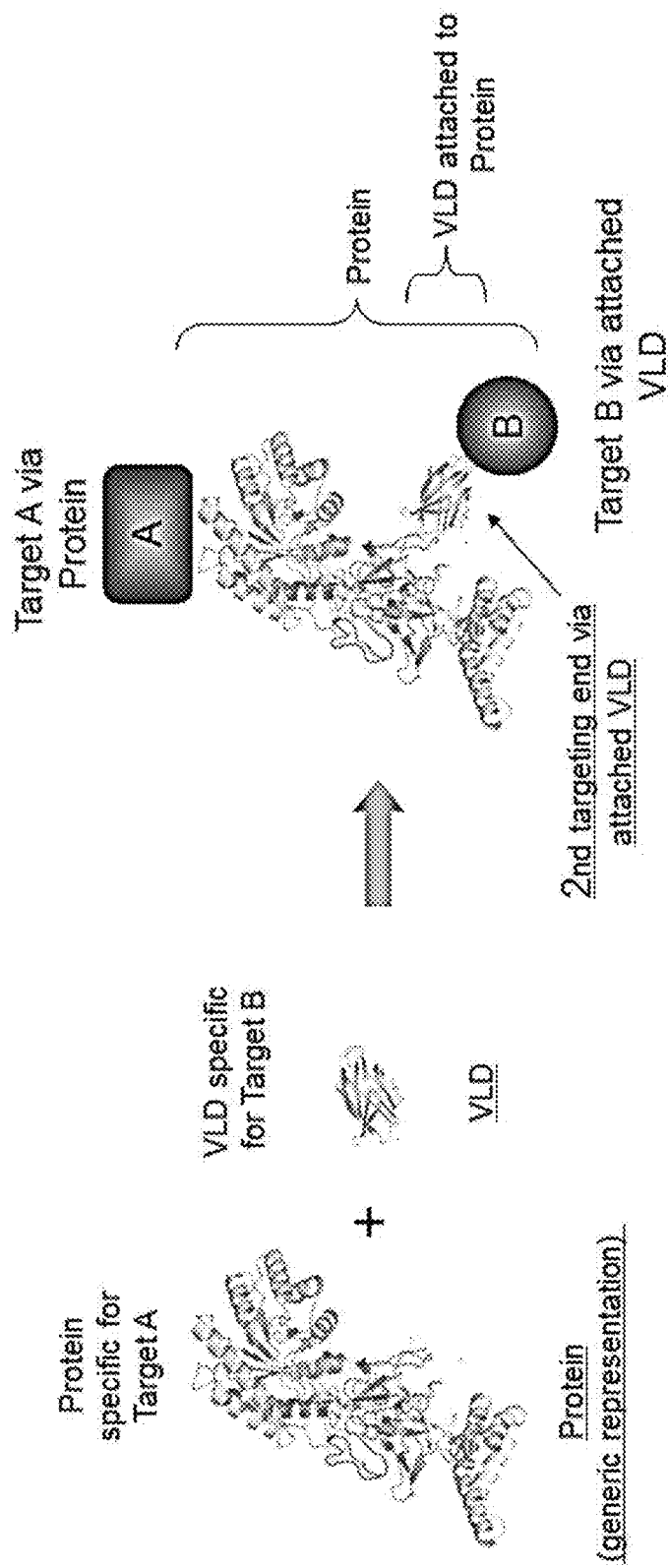

FIG. 25 shows a schematic of a protein (generic representation) coupled to a VLD according to one example of the disclosure. The protein binds to target A. A VLD is attached to the C-terminus of the protein polypeptide and binds to Target B. The bi-specific can bind to both Target A and B either individually or at the same time.

Figure 26:
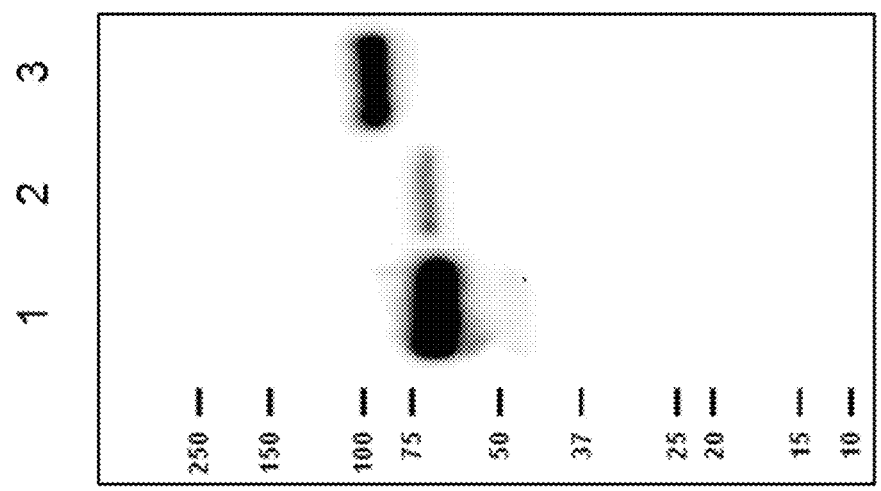

FIG. 26 shows Western blot analysis and detection with anti-His horse radish peroxidase (HRP) of the purified human serum albumin (HAS)—VLD fusion proteins. Lane 1 is HSA with the VLD fused to the C-terminus; Lane 2 is HSA with the VLD fused to the N-terminus; Lane 3 is HSA with VLDs fused to both the N-terminus and C-terminus.

Figure 27:
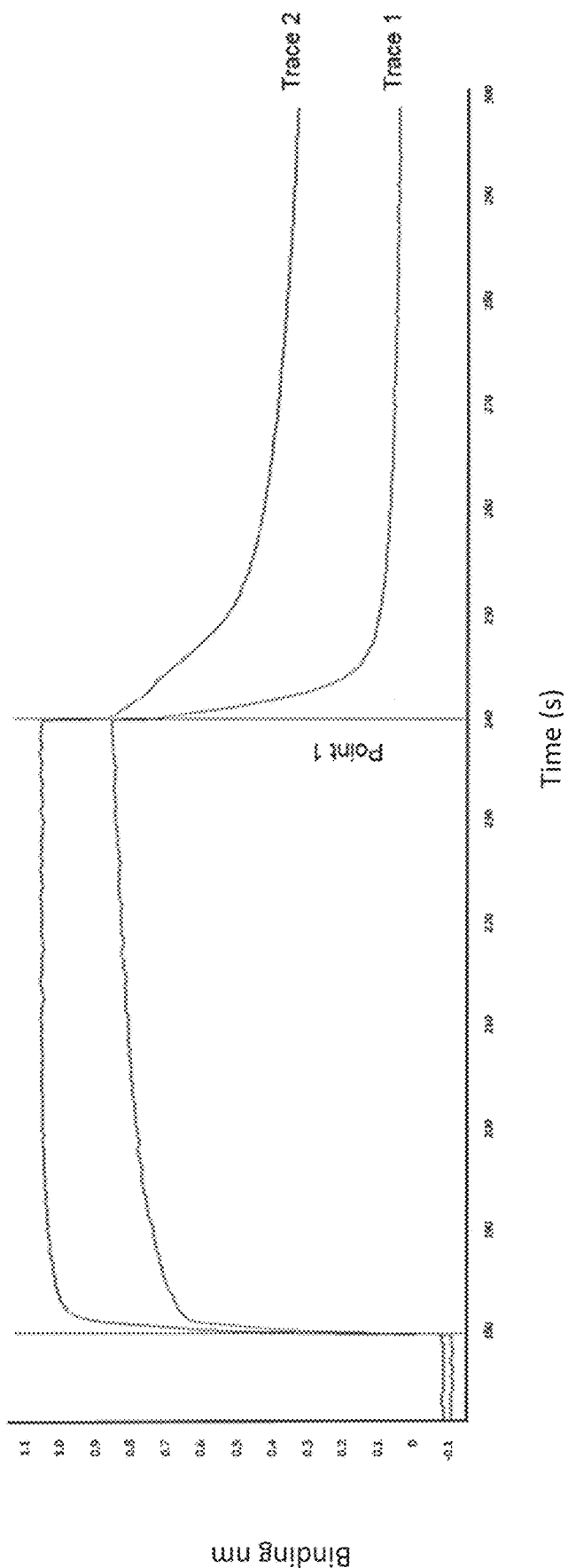

FIG. 27 shows analysis using the ForteBio Blitz biosensor to demonstrate binding of the HSA-VLD fusion proteins to B7-2-Fc. Trace 1 corresponds to the HSA-VLD fusion protein which as a B7-2 binding VLD attached to the C-terminus of HSA. Trace 2 corresponds to the VDL-HSA-VLD construct having a B7-2 binding VLD attached to both the N and C-terminus of HSA. Point 1 corresponds to the addition of buffer.

Figure 28:
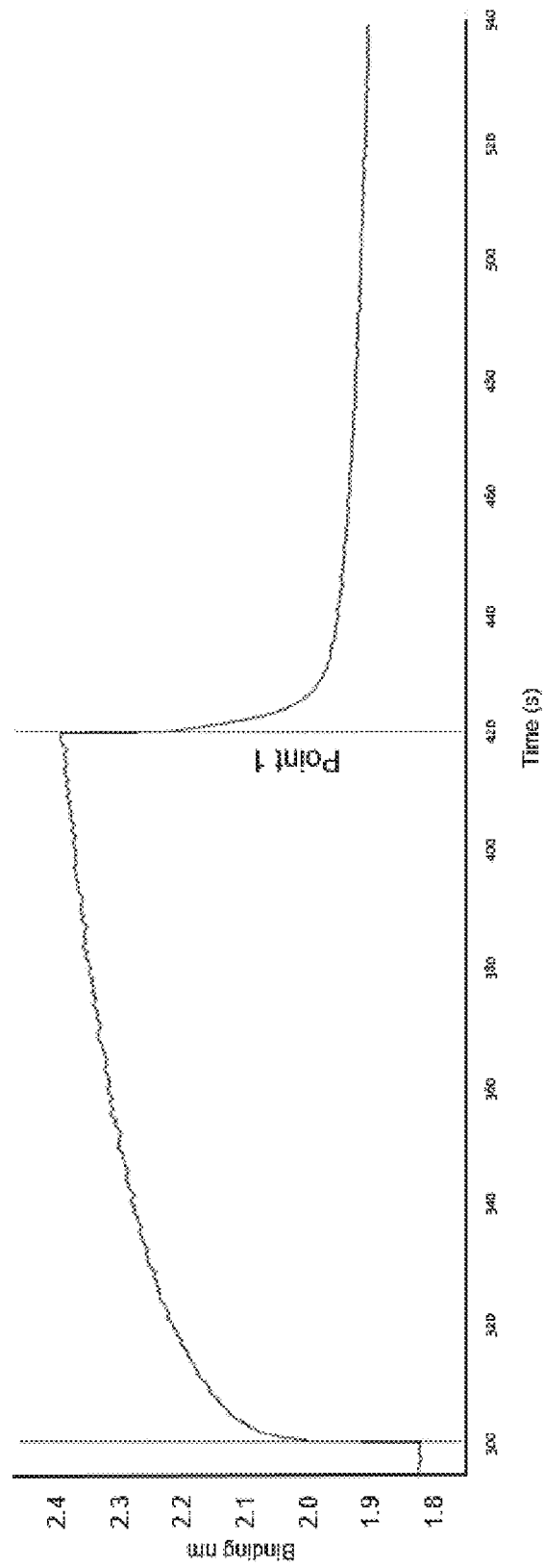

FIG. 28 shows analysis using the ForteBio Blitz biosensor to demonstrate binding of the HSA-VLD to CD3. The trace shown corresponds to the binding of the molecule to CD3de. Point 1 corresponds to the addition of buffer.

Figure 29:
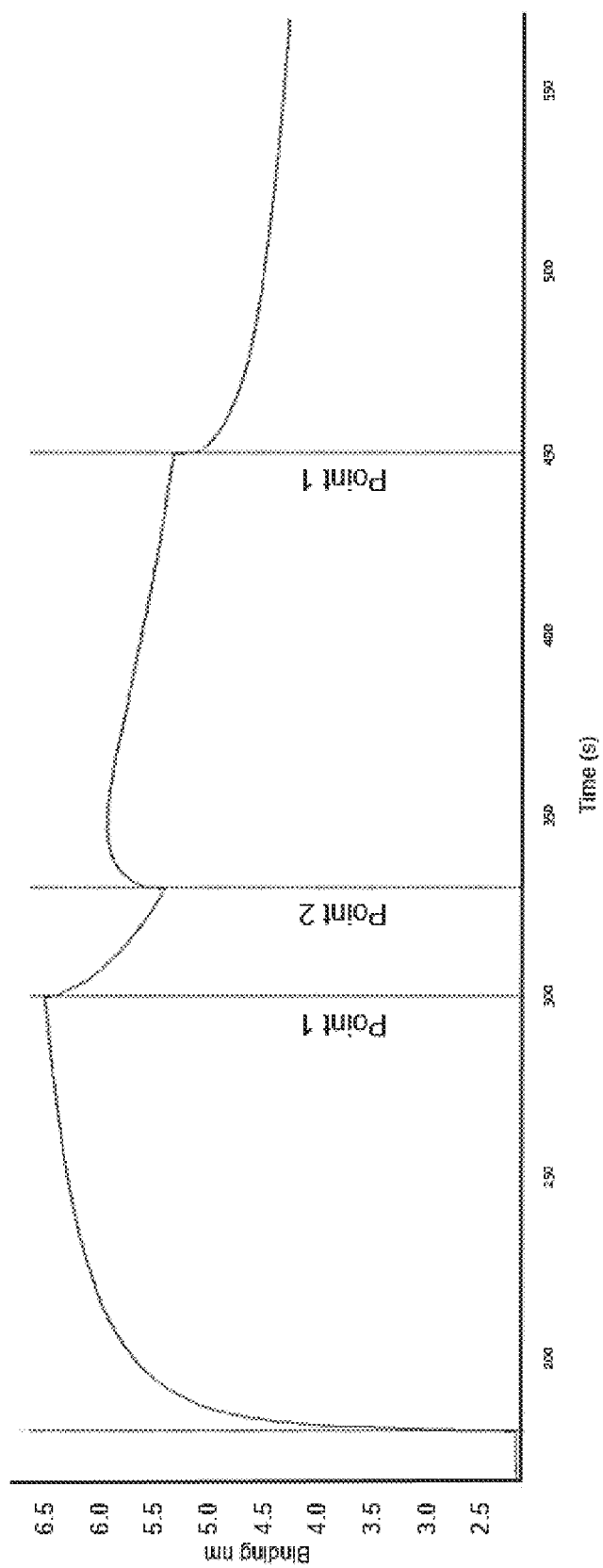

FIG. 29 shows analysis using the ForteBio Blitz biosensor to demonstrate binding of HSA-VLD fusion protein to anti-HSA affibody and B7-2-Fc. The trace shown corresponds to the binding of the molecule to an anti-HSA affibody. Points 1, 2 and 3 correspond to the addition of buffer.

Key to Sequence Listing

SEQ ID NO:1 sequence of the human native CTLA4 scaffold (extracellular domain)
SEQ ID NO:2 sequence of exposed binding loop 1 of CTLA4
SEQ ID NO:3 sequence of exposed binding loop 2 of CTLA4
SEQ ID NO:4 sequence of exposed binding loop 3 of CTLA4
SEQ ID NO:5 sequence of a BDM VLD scaffold
SEQ ID NO:6 sequence of a BDM VLD scaffold
SEQ ID NO:7 binding loop 1 sequence
SEQ ID NO:8 signal peptide sequence
SEQ ID NO:9 binding loop 3 sequence
SEQ ID NO:10 binding loop 1 sequence
SEQ ID NO:11 binding loop 2 sequence
SEQ ID NO:12 binding loop 3 sequence
SEQ ID NO:13 sequence of B7-1 binding VLD scaffold
SEQ ID NO:14 sequence of a sclerostin binding VLD scaffold
SEQ ID NO:15 linker sequence
SEQ ID NO:16 linker sequence
SEQ ID NO:17 linker sequence
SEQ ID NO:18 sequence of anti-lysozyme IgG1 heavy chain
SEQ ID NO:19 sequence of anti-lysozyme IgG1 heavy chain coupled to a B7-1 binding VLD by a linker
SEQ ID NO:20 sequence of anti-lysozyme IgG kappa light chain
SEQ ID NO:21 sequence of anti-lysozyme IgG kappa light coupled to a B7-1 binding VLD by a linker
SEQ ID NO:22 sequence of anti-lysozyme Fab kappa light chain coupled to B7-1 binding VLD by a linker
SEQ ID NO:23 sequence of anti-lysozyme Fab heavy chain coupled to B7-1 binding VLD by a linker
SEQ ID NO:24 sequence of anti-lysozyme Fab heavy chain with C-terminal histidine and myc tags
SEQ ID NO:25 sequence of anti-lysozyme IgG1 heavy chain fused to anti-sclerostin VLD
SEQ ID NO:26 sequence of the B7-2 binding VLD fused to the C-terminus of human serum albumin SEQ ID NO:27 sequence of the B7-2 binding VLD fused to the N-terminus of human serum albumin SEQ ID NO:28 sequence of the B7-2 binding VLD fused to both the N-terminus and the C-terminus of human serum albumin SEQ ID NO:29 sequence of CD3 binding VLD fused to the C-terminus of human serum albumin SEQ ID NO:30 nucleotide sequence of BDM VLD scaffold.

DETAILED DESCRIPTION

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

Any example or embodiment of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat Sequences of Proteins of Immunological Interest, National Institutes of Health, Bethesda, Md., 1987 and 1991, Bork et al., J Mol. Biol. 242, 309-320, 1994, Chothia and Lesk J. Mol Biol. 196:901-917, 1987, Chothia et al. Nature 342, 877-883, 1989 and/or or Al-Lazikani et al., J Mol Biol 273, 927-948, 1997.

The term “and/or”, e.g., “X and/or Y” shall be understood to mean either “X and Y” or “X or Y” and shall be taken to provide explicit support for both meanings or for either meaning.

As used herein, “a” or “an” means “at least one” or “one or more” unless the context implies otherwise.

Throughout this specification the word ‘comprise’, or variations such as ‘comprises’ or ‘comprising’, will be understood to imply the inclusion of a stated element, integer or step, or group of elements, integers or steps, but not the exclusion of any other element, integer or step, or group of elements, integers or steps.

Selected Definitions

The letter “x” as used in amino acid sequences herein is intended to indicate that any of the twenty standard amino acids may be placed at this position unless specifically noted otherwise.

As used herein, “identity” means the percentage of identical nucleotide or amino acid residues at corresponding positions in two or more sequences when the sequences are aligned to maximize sequence matching, i.e., taking into account gaps and insertions. Identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990) and Altschul et al. Nuc. Acids Res. 25: 3389-3402 (1997)). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990).

The term “sequence identity” as used herein means the percentage of pair-wise identical residues following alignment of the a sequence of a polypeptide of the present disclosure with a sequence in question with respect to the number of residues in the longer of these two sequence. Identity is measured by dividing the number of identical residues by the total number of residues and multiplying the product by 100. Thus the identity between two sequences will typically be expressed as a percentage.

The term “immunoglobulin” refers to a family of polypeptides which retain the immunoglobulin fold characteristics of antibody molecules, which contains two beta sheets and, usually, a conserved disulphide bond. Members of the Ig superfamily include antibodies, T-cell receptor molecules and the like, ICAM molecules (which are involved in cell adhesion), receptor molecules such as the PDGF receptor which are involved in intracellular signalling. Preferably the present invention relates to antibodies.

An “immunoglobulin-like domain” refers to a beta-sandwich structural motif found in proteins of diverse function including for example, extracellular matrix proteins, muscle proteins, immune proteins, cell-surface receptors and enzymes. Ig-like domain members have been divided into various superfamilies, including for example, the immunoglobulin, fibronectin type III and cadherin superfamilies. Other superfamilies containing the Ig-like domain structural motif include, for example, members of the PKD domain, β-galactosidase/glucuronidase domain, transglutamase two C-terminal domains, actinoxanthin-like, CuZn superoxide dismutase-like, CBD9-like, lamin NC globular tail domain, clathrin adaptor appendage domain, integrin domains, PapD-like, purple acid phosphatase N-terminal domain, superoxide reductase-like, thiol:disulfide interchange protein DsbD N-terminal domain and invasin/intimin cell adhesion fragments superfamilies. Ig-like domain structural similarity is maintained between members of different superfamilies irrespective of significant sequence identity. The term is intended to include Ig-like domain members within and across each superfamily. Therefore, the term "immunoglobulin-like (Ig-like) domain containing superfamily" is intended to refer to an Ig-like domain containing member polypeptide within any of these superfamilies as well as others known in the art. A description of the different Ig-like domain containing superfamilies can be found, for example, in Clarke et al., Structure Fold. Des. 7:1145-53 (1999) and within structural databases such as at the URL pdb.weizmann.ac.il/scop/data/scop.b.c.b.html.

The term "antibody" can include all classes, for example IgG, IgM, IgA, IgD or IgE or sub-classes e.g. $IgG_1$, $IgG_2$, $IgG_3$, $IgG_4$, $IgA_1$ and $IgA_2$ whether derived from any species naturally producing an antibody, or created by recombinant DNA technology, whether isolated from serum, B cells, hybridomas, transfectomas, yeast or bacteria or synthetically produced. The term 'antibody' covers monoclonal antibodies, polyclonal antibodies, human antibodies, humanised antibodies, chimeric antibodies, primatised antibodies or synhumanized antibodies. The term "human antibody" refers to antibodies containing sequences of human origin, except for possible non-human CDR regions and which has minimal immunogenicity in humans.

The term "full-length antibody" as used herein is intended to refer to an antibody in its substantially intact form, as opposed to an antigen binding fragment of an antibody. It may be isolated or recombinant. Specifically, whole antibodies include those with heavy and light chains including an Fc region. The constant domains may be wild-type sequence constant domains (e.g., human wild-type sequence constant domains) or amino acid sequence variants thereof. The antibody protein comprises a variable region made up of a plurality of polypeptide chains, e.g., a polypeptide comprising a light chain variable region (VL) and a polypeptide comprising a heavy chain variable region (VH). An antibody also comprises constant domains, some of which can be arranged into a constant region, which includes a constant fragment or fragment crystallizable (Fc), in the case of a heavy chain. A VH and a VL interact to form a Fv comprising an antigen binding region that is capable of specifically binding to one or a few closely related antigens. Binding interaction of the antibody with an antigen can be manifested as an intermolecular contact with one or more amino acid residues of a complementarity determining region (CDR). Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., IgG1, IgG2, IgG3, IgG4, IgA1 and IgA2) or subclass. The antibody may be a human, humanised, or chimeric antibody. In yet another example, the antibody is a shark, camelid, feline or canine antibody.

The term "immunoglobulin antigen-binding fragment" as used herein is intended to refers to a fragment of an antibody, which fragment includes a light chain variable region and a heavy chain variable region having complementarity determining regions (CDRs). The term encompasses an Fab, $F(ab')_2$, Fab', scFv, di-scFv, or chemically linked $F(ab')_2$.

The term "Fab is understood to refer to a region of an antibody that binds antigen and is composed of one constant and one variable domain of each of the heavy and the light chain.

The term "complementary" refers to immunoglobulin domains which form cognate pairs. For example, a VH and a VL domain of an antibody are complementary, two VH domains are not complementary and two VL domains are not complementary.

The term "domain" refers to a folded protein structure which retains its tertiary structure independently of the rest of the protein.

The term 'CDR' or 'complementarity determining region' is intended to mean the non-contiguous antigen combining sites found within the variable region of both heavy and light chain polypeptides within an antibody or antibody fragment (which binds to an antigen). These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein.

A "binding domain molecule (BDM)" refers to a monomeric domain which has similar structural features to the variable heavy (VH) chain or variable light (VL) chain of an antibody. These similar structural features include BL (Binding Loop) sequences which are surface polypeptide loop structures or regions that function in a similar manner to the complementarity determining regions (CDRs) in antibody variable domains that bind to specific antigens. The BDM scaffold consists of a framework sequence and three BL sequences contained within. A BDM herein is not an antibody variable domain. BDM scaffolds are described herein, including for example CTLA-4, lipocallins, fibronectin, ICOS and CD28.

A "BL sequence" is surface polypeptide loop structure or region that function in a similar manner to the complementarity determining regions (CDRs) in antibody variable domains that bind to specific antigens. Three antigen binding loop sequences (referred to herein as BL-1, BL-2 and BL-3 respectively) are present in the BDM and they sit within a scaffold sequence which provides the required three dimensional conformation of the loop sequences. Native BL sequences can be replaced with one or more corresponding antibody CDRs which can be grafted onto the scaffold. Diversity can be introduced into the BL sites of the BDM by randomising the amino acid sequence of the specific loops of the scaffold e.g. by introducing NNK codons followed by selection for desired binding characteristics using, for example, display technologies. This mechanism is similar to natural selection of high affinity, antigen-specific antibodies.

The term 'binding specificity' in the context of a protein, polypeptide or peptide, refers to the ability of the protein or peptide and/or BDM to bind its respective target antigen or epitope which is dependent upon the presence of a particular structure (e.g., an antigenic determinant or epitope) on the target antigen or epitope. For example, a protein and/or BDM recognizes and binds to a specific protein structure rather than to proteins generally. By way of example, if a protein binds to epitope "A", the presence of a molecule containing epitope "A" (or free, unlabelled "A"), in a reaction containing labelled "A" and the protein, will reduce the amount of labelled "A" bound to the protein. The term should also be understood to include that the pharmacologically active protein or peptide and/or BDM "specifically binds" to a target antigen. The term 'specifically binds' or 'binds specifically' shall be taken to mean that the pharmacologically active protein (or antigen binding domain thereof in the case of an antibody) or peptide and/or the BDM of the present disclosure reacts or associates more frequently, more rapidly, with greater duration and/or with greater affinity with a particular target antigen than it does with alternative target antigens. Reference to 'binding' provides explicit support for the term 'specific binding' and vice versa. Typically, the term is used to describe the affinity of a moiety (i.e. protein or BDM herein) for a given target antigen. In some circumstances, it may be desirable to have low affinity binding where toxicity may be an issue. In other circumstances it may be desirable to have high affinity binding to minimise cross-reactivity to other target antigens. In one example, the binding is specific binding as defined herein.

The term "selective binding" is described in more detail elsewhere herein. The term "binding affinity" or "affinity" of a moiety of the molecule (i.e. the protein or the BDM) to a selected target can be measured. The term 'affinity' refers to the equilibrium constant for the reversible binding of two agents and is expressed as a dissociation constant (Kd) or equilibrium dissociation constant (KD).

As used herein, the term 'avidity' refers to the resistance of a complex of two or more agents to dissociation after dilution.

The term 'antigen' as used herein means a substance to which the pharmacologically active protein or peptide or BDM binds. An antigen will typically comprise one or more antigenic epitopes which are recognised by the BDM or protein or peptide. The protein antigen may be a soluble protein or membrane bound protein. Examples of soluble proteins include, but are not limited to transcription factors, antibodies, growth factors, blood proteins (e.g. albumin), or drugs (e.g. steroid, pharmaceutical drugs etc.). Types of membrane bound proteins include growth factor receptors, tumour markers, cell surface markers, or markers which mediate transport into a cell (e.g. transferrin), or Fc receptor. It typically refers to a substance which is capable of raising an immune response in vivo. It may be a polypeptide, protein, nucleic acid (e.g. DNA, RNA or a combination of DNA and RNA) or other molecule.

As used herein, the term 'epitope' (syn. "antigenic determinant") shall be understood to mean a region to which a protein (or an antigen-binding domain of an antibody or immunoglobulin antigen-binding fragment) binds or which the BDM of the present disclosure binds. Conventionally, the term refers to a structure bound by an immunoglobulin VH/VL pair. An epitope defines the minimum binding site for an antibody or antibody-like domain (e.g. BDM). This term is not necessarily limited to the specific residues or structure to which a protein and/or the BDM of the molecule makes contact. For example, this term includes a region spanning amino acids contacted by the CDRs of the antibody or immunoglobulin antigen-binding fragment or BL sequences of the BDM respectively, and 5-10 (or more) or 2-5 or 1-3 amino acids outside of this region. In some examples, the epitope comprises a series of discontinuous amino acids that are positioned close to one another when a polypeptide is folded and, for example, associated with another polypeptide, i.e., a 'conformational epitope'. The term includes those composed of a linear peptide sequence (i.e., "continuous") or those composed of non-contiguous amino acid sequences (i.e., "conformational" or "discontinuous").

The term "target" as used herein refers to an antigen or an epitope. In certain examples, the target refers to a cell-surface protein e.g. receptor or a viral coat protein. In other examples, the target is a secreted protein.

As used herein, the term 'antigen binding domain' in the context of an antibody or immunoglobulin antigen-binding fragment shall be taken to mean a region of an antibody or immunoglobulin antigen-binding fragment that is capable of specifically binding to an antigen, more particularly an epitope present on an antigen. In an antibody, the antigen binding domain corresponds to the $V_H$ and $V_L$. Within the $V_H$ and $V_L$ regions are the CDRs which make contact with the epitope.

The term "position" or "positions" as used herein means the position of an amino acid within an amino acid sequence depicted herein, typically counting from the left or 5' end of the sequence. The term "corresponding" as used herein in the context of the amino acid sequence positions of a BDM refers to the position of an amino acid by reference to the native or "wild-type" BDM sequence. Preferably, the positions will be the amino acids corresponding to the BLS1, and/or BLS2 and/or BLS3 respectively in the native BDM sequence.

As used herein, the term "native sequence" is intended to refer to a sequence that has the same amino acid sequence as the corresponding polypeptide derived from nature. Thus, a "native BDM" refers to that polypeptide having an amino acid sequence that is the same amino acid sequence as the corresponding polypeptide derived from nature. Such native sequence polypeptide can be produced by recombinant or synthetic means.

The term 'protein' shall be taken to include a single continuous and unbranched polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulfide bond. Examples of non-covalent bonds include hydrogen bonds, ionic bonds, Van der Waals forces, and hydrophobic interactions.

The term "peptide" as used herein is taken to refer to a short chain (typically of about 50 amino acids or less) of amino acid monomers linked by peptide (amide) bonds.

The term "isolated" as used herein refers to a polypeptide, antibody, protein etc. that has been identified and separated and/or recovered from a component of its natural environment or the environment from which it has been produced. Contaminant components of its natural environment are materials that would interfere with therapeutic uses for the polypeptide, and can include, for example, enzymes, hormones, and other proteinaceous or non-proteinaceous solutes. In one example, the polypeptide will be purified (1) to greater than 80%, 85%, 90%, 95%, or 99% by weight as determined by the Lowry method, (2) to a degree sufficient to obtain at least 15 residues of N-terminal or internal amino acid sequence by use of a spinning cup sequenator, and/or (3) to homogeneity by SDS-PAGE under reducing or non-reducing conditions using Coomassie blue or silver stain. The term 'isolated polypeptide' includes within its scope a polypeptide in situ within recombinant cells since at least one component of the polypeptides natural environment will not be present. Generally, isolation of the polypeptide will include at least one purification step.

The term "recombinant" shall be understood to mean the product of artificial genetic recombination. A recombinant polypeptide also encompasses a polypeptide expressed by artificial recombinant means when it is within a cell, tissue or subject, e.g., in which it is expressed.

The term "detect" or "detecting" as used herein is understood both on a quantitative and a qualitative level, as well as a combination thereof. It thus includes quantitative, semi-quantitative and qualitative measurements of a molecule of interest.

As used herein, the term 'subject' shall be taken to mean any animal including humans, for example a mammal. Exemplary subjects include but are not limited to humans and non-human primates. For example, the subject is a human. The term 'subject' is also intended to include non-human subjects such as for example, hamsters, rats, rabbits, cats, dogs and horses.

Binding Domain Molecules (BDMs)

The binding domain molecules (BDMs) of the present disclosure preferably contain a protein scaffold having three exposed binding loops (BLs). The BLs can be altered i.e. replaced or modified by amino acid substitution to confer binding specificity of the BDM to a given target antigen. The BDM scaffold of the present disclosure may be selected from the group consisting of an immunoglobulin-like (Ig-like) domain containing superfamily member, i-body, VNAR or VHH.

The Ig-like domain containing superfamily member may be selected from the group consisting of V-like domain (e.g. VLD) such as CTLA-4, C-set domain, a ThyOx family member polypeptide, a T cell receptor, CD2, CD4, CD8, class I MHC, class II MHC, CD1, cytokine receptor, G-CSF receptor, GM-CSF receptor, hormone receptors, growth hormone receptor, erythropoietin receptor, interferon gamma receptor, prolactin receptor, NCAM, VCAM, ICAM, N-caderin, E-caderin, fibronectin, tenascin, and I-set containing domain polypeptides or a functional fragment thereof.

Examples of BDMs according to the disclosure include lipocalin, protein A derived molecules such as Z-domain of Protein A (affibody, SpA), an affibody, adnectin (e.g., fibronectin) or Ankyrin repeat protein (DARPin).

The BDMs of the present disclosure have the advantages of being stable and modular in both the scaffold domain structures as well as in the ability to accept a broad range of heterologous binding loop sequences. Additionally, the BDM scaffold can be readily obtainable from human sources so that their immunogenicity when used as a human therapeutic is negligible. The BDM scaffolds can also be readily constructed to contain or omit naturally occurring polysaccharide chains.

Joinder of the heterologous binding loop sequences into the BDM scaffold can be performed by, for example, chemical, biochemical or recombinant means.

Preferably, a BDM of the present disclosure refers to a molecule other than a human antibody as produced by a B cell. A BDM molecule of the present disclosure is also intended to exclude antibody fragments greater than complementarity determining regions (CDRs). Therefore human antibody variable region fragments greater than about 50, 75, 100 or 110 amino acids are not encompassed within the term BDM. Furthermore, a BDM does not include an antibody variable region such as dAb, VH-VH or VL-VL structures.

The term "scaffold" is intended to mean a supporting polypeptide framework used to organise, orient and harbour heterologous binding loops or altered amino acid sequences conferring binding specificity to a given target. A scaffold can be structurally separable from the amino acid sequences conferring binding specificity. The structurally separable portion of a scaffold can include a variety of different structural motifs including, for example, beta-sandwich, beta-sheet, alpha-helix, beta-barrel, coil-coiled and other polypeptide secondary and tertiary structures known in the art. A scaffold of the present disclosure will also contain one or more regions that can be varied in amino acid sequence without substantially reducing the stability of the supporting framework structure. An exemplary region that can be varied includes a binding loop segment that joins two strands of a beta-sandwich or beta-sheet.

A BDM scaffold of the present disclosure preferably exhibits less than about 50% amino acid identity to a human immunoglobulin variable heavy or light chain sequence. Generally, the scaffold will exhibit, for example, amino acid sequence identity less than about 45%, about 40%, about 30%, about 20%, about 15%, or about 10% compared to a human immunoglobulin variable heavy or light chain amino acid sequence.

Residues of a scaffold that can be varied are referred to herein as external binding loops or binding loop sequences (designed herein as BL-1, BL-2 and BL-3 respectively). Residues conferring secondary or tertiary structural properties can be retained, modified or conserved so long as the overall structure of the scaffold is maintained. Those skilled in the art know, or can determine which residues function in structural stability of a polypeptide scaffold as well as the extent to which such residues can be modified.

In one example, the BDM scaffold is a V-like domain (VLD) protein.

VLDs are typically distinguished from those of antibodies or T-cell receptors because they have no propensity to join together into Fv-type molecules. VLD are discussed in The Leucocyte Antigen Facts Book 1993, Eds Barclay et al., Academic Press, London; and in CD Antigens 1996 (1997) Immunology Today 18, 100-101, and in Arlene H Sharpe and Gordon J Freeman, (2002) Nature Reviews Immunology 2, 116-126, the entire contents of which are incorporated herein by reference.

A person skilled in the art in the subject matter of the present disclosure can readily determine appropriate VLD containing proteins suitable for use herein for example by conducting a search of the Uniprot database (www.uniprot.org).

VLD containing proteins such as CTLA-4 can provide an alternative framework for the development of novel binding moieties with high affinities for target molecules. Single domain V-like binding molecules derived from these binding moieties are soluble and therefore desirable. Examples of suitable binding moieties containing a VLD are CTLA-4, CD28 and ICOS (Hutloff A et al, (1999) Nature 397(6716): 263-6).

Cytotoxic T-lymphocyte associated antigen 4 (CTLA-4) and the homologous cell-surface proteins CD28 and ICOS, are involved in T-cell regulation during the immune response. CTLA-4 is a 44 kDa homodimer expressed primarily and transiently on the surface of activated T-cells, where it interacts with CD80 and CD86 surface antigens on antigen presenting cells to effect regulation of the immune response (Waterhouse et al. (1996) Immunol Rev 153:183-207, van der Merwe et al. (1997) J Exp Med 185(3):393-403).

CD28 is a 44 kDa homodimer expressed predominantly on T-cells and, like CTLA-4, interacts with CD80 and CD86 surface antigens on antigen presenting cells to effect regulation of the immune response (Linsley et al. (1990) J Immunol 182(5):2559-63). Current theory suggests that competition between CTLA-4 and CD28 for available ligands controls the level of immune response, for example, gene deletion of CTLA-4 in knock-out mice results in a massive over-proliferation of activated T-cells (Waterhouse et al. (1995) Science 270(5238):985-8).

Each CTLA-4 monomeric subunit consists of an N-terminal extracellular domain, transmembrane region and C-terminal intracellular domain. The extracellular domain comprises an N-terminal V-like domain (VLD; of approximately 14 kDa predicted molecular weight by homology to the immunoglobulin superfamily) and a stalk of about 10 residues connecting the VLD to the transmembrane region. The VLD comprises surface loops corresponding to BL-1, BL-2 and BL-3 respectively (Metzler W J et al (1997) Nat Struct Biol 4(7):527-31) which binds to CD80 and/or CD86. The sequence of human CTLA-4 has been previously determined (U.S. Pat. Nos. 5,434,131; 5,844,095; 5,851,795).

Structural and mutational studies on CTLA-4 suggest that binding to CD80 and CD86 occurs via the VLD surface formed from A'GFCC' V-like beta-strands and also from the highly conserved MYPPPYY (SEQ ID NO: 32) sequence in the BL-3. Dimerisation between CTLA-4 monomers occurs through a disulphide bond between cysteine residues ($Cys^{120}$) in the two stalks, which results in tethering of the two extracellular domains, but without any apparent direct association between V-like domains (Metzler W J et al (1997) Nat Struct Biol 4(7):527-31). Dimerisation appears to contribute exclusively to increased avidity for the ligands.

CD278 or ICOS (inducible T-cell co-stimulator) is an immune checkpoint protein that is encoded by the/COS gene. It is expressed on activated T cells. The protein belongs to the CD28 and CTLA-4 cell surface receptor family. It forms homodimers and plays a role in signalling, immune responses and regulation of cell proliferation.

The sequences of human CTLA4, CD28 and ICOS are available on publically accessible databases.

The human sequence for CTLA-4 is available as UniProt reference P16410. The extracellular domain of CTLA-4 corresponds to positions 36-161 of the sequence (wherein the CTLA-4 has a total length of 126 amino acids). Amino acid residues 1-35 correspond to the signal peptide.

The human sequence for CD28 is available as UniProt reference P10747. The extracellular domain corresponds to positions 19-152 of the sequence.

The human sequence for ICOS is available as UniProt reference Q9Y6W8. The Ig-like VLD corresponds to positions 30-132 of the sequence.

In one example, the BDM is an immunoglobulin C-set domain protein, more preferably a C1-set domain protein. C-set domains are classical Ig-like domains resembling the antibody constant domain and are found almost exclusively in molecules involved in the immune system, including the major histocompatibility complex (MHC) class I and II complex molecules and in various T cell receptors.

A person skilled in the art in the subject matter of the present disclosure can readily determine proteins containing a C-set domain which are suitable for use herein. For example, a search of the uniprot database (www.uniprot.org) reveals over 300 human proteins.

Proteins such as basigin contain a C-set domain (Xiao-Ling Yu et al. (2008) JBC vol 283(26)18056-18065). Further examples of C-set domains include ROR1 extracellular domain, CEA family members such as CEACAM1-8.

BDMs can be affinity matured using known selection and/or mutagenesis methods. Affinity matured BDMs can have an affinity which is two times, five times, ten times, twenty times, thirty times or greater than the starting BDM. Apparent affinities can be determined by methods such as ELISA or other technique familiar to persons skilled in the art e.g. surface plasmon resonance technique.

An i-body is a single domain antibody-like molecule of human origin. The i-body framework resembles the single domain antibody from sharks and as a result shares the favourable biophysical and targeting properties of the shark antibody. They are described in for example, U.S. Pat. No. 7,977,071.

A VNAR (variable new antigen receptor) refers to a single variable region domain fragment derived from a shark immunoglobulin new antigen receptor antibody (IgNAR). They are described for example in Griffiths K et al (2013) Antibodies 2(1):66-81.

A VHH (variable domain of heavy chain) domain or nanobody refers to a single monomeric variable antibody domain derived from camelid antibodies. They are described, for example in Harmsen M M and H J De Haard (2007) Appl Microbiol Biotechnol. 77(1):13-22.

The binding specificity of the BDM and pharmacologically active protein moieties of the molecule can be exploited to allow the molecule to bind to one or more different target antigens or epitopes, preferably at least two different target antigens or epitopes. In one example, the protein has binding specificity for a first target antigen and the at least one BDM has binding specificity for a second target antigen.

In examples where multiple BDMs are coupled to a protein, the protein can have binding specificity for a first target antigen, and the BDM can have binding specificity for a second target antigen, and a further BDM (if present) can have binding specificity for a third target antigen. In other examples where the protein is an antibody or immunoglobulin antigen-binding fragment, the antibody or antigen-binding fragment can have binding specificity for a first target antigen, and BDM (or pair thereof if an BDM is present for example on each heavy chain or each light chain) can have binding specificity for a second target antigen, and a further BDM (or pair thereof) can have binding specificity for a third target antigen.

The molecule of the present disclosure may bind to at least one target antigen, at least two different target antigens, at least three different target antigens, at least four different target antigens or at least five different target antigens.

Preferably, the molecule binds to one target antigen, two different target antigens or three different target antigens. Various non-limiting examples are contemplated, including:

(i) the protein or peptide binds to a first target antigen which is the same or different as the second target antigen bound by the BDM;

(ii) the antibody or immunoglobulin antigen-binding fragment binds to a first target antigen which is the same as the second target antigen bound by the BDM;

(iii) the antibody or immunoglobulin antigen-binding fragment binds to a first target antigen which is different from the second target antigen bound by the BDM;

(iv) the antibody or immunoglobulin antigen-binding fragment binds to a first target antigen, an BDM binds to a second target antigen which is the same as the first target antigen, and a further BDM binds to a third target antigen which is different from the first and second target antigens;

(v) the antibody or immunoglobulin antigen-binding fragment binds to a first target antigen, a BDM and further BDM bind to a second and third target antigen respectively, wherein the second and third target antigens may be the same or different, but wherein the second and third target antigens are different from the first target antigen;

(vi) the antibody or immunoglobulin antigen-binding fragment binds to a first target antigen, a BDM binds to a second target antigen and a further BDM binds to a third target antigen wherein the first, second and third target antigens are different.

It will be appreciated that when two or more BDM are linked together, the number of potential targets that can be bound by the molecule may increase.

Generation of BDMs

As shown herein, replacement of one or more binding loop structures in the BDM domain (e.g. CTLA-4) with heterologous binding loop sequences for sclerostin or CD3 resulted in the production of soluble, monomeric, unglycosylated binding molecules using a bacterial expression system. The V-like domains thus provide a basic framework for constructing soluble, single domain molecules wherein the binding specificity of the molecule may be engineered by modifications of the binding loop structures.

The framework residues of the BDM may be modified in accordance with structural features present in camelid antibodies. The camel heavy chain immunoglobulins differ from conventional antibody structures by consisting of a single VH domain.

Several non-conventional substitutions (predominantly hydrophobic to polar in nature) at exposed framework residues reduce the hydrophobic surface, while maintaining the internal beta-sheet framework structure (Desmyter et al. (1996) Nat Struct Biol 3:803-811). Within the three binding loops several structural features compensate for the loss of antigen binding-surface usually provided by the VL domain. While the BL2 loop does not differ extensively from other VH domains, the BL1 and BL3 adopt non-canonical conformations which are extremely heterologous in length. For example, the H1 loop may contain anywhere between 2-8 residues compared to the usual five in Ig molecules. However, it is the BL3 which exhibits greatest variation: in 17 camel antibody sequences reported, the length of this region varies between 7 and 21 residues (Muyldermans et al. (1994) Protein Eng 7:1129-1135). Thirdly, many camelid VH domains possess a disulphide linkage interconnecting BL1 and BL3 in the case of camels and interconnecting CDRs-1 and -2 in the case of llamas (Vu et al. 1997). The function of this structural feature appears to be maintenance of loop stability and providing a more contoured, as distinct from planar, loop conformation which both allows binding to pockets within the antigen and gives an increased surface area. However, not all camelid antibodies possess this disulphide bond suggesting that it is not an absolute structural requirement.

These foregoing features have enabled camelid V-domains to present as soluble molecules in vivo and with sufficiently high affinity to form an effective immune response against a wide variety of target antigens.

Methods for generating and selecting single VLD molecules with novel binding affinities for target molecules have been described in U.S. Pat. No. 7,166,697, the entire contents of which are incorporated by reference. The method involves the application of well-known molecular evolution techniques to V-like domains derived from members of the immunoglobulin superfamily. The method may involve the production of phage or ribosomal display libraries for screening large numbers of mutated V-like domains.

Filamentous fd-bacteriophage genomes are engineered such that the phage display, on their surface, proteins such as the Ig-like proteins (Fabs) which are encoded by the DNA that is contained within the phage (Smith, 1985; Huse et al., 1989; McCafferty et al., 1990; Hoogenboom et al., 1991). Protein molecules can be displayed on the surface of Fd bacteriophage, covalently coupled to phage coat proteins encoded by gene III, or less commonly gene VIII. Insertion of antibody genes into the gene III coat protein give expression of 3-5 recombinant protein molecules per phage, situated at the ends. In contrast, insertion of antibody genes into gene VIII has the potential to display about 2000 copies of the recombinant protein per phage particle, however this is a multivalent system which could mask the affinity of a single displayed protein. Fd phagemid vectors are also used, since they can be easily switched from the display of functional Ig-like fragments on the surface of Fd-bacteriophage to secreting soluble Ig-like fragments in *E. coli*. Phage-displayed recombinant protein fusions with the N-terminus of the gene III coat protein are made possible by an amber codon strategically positioned between the two protein genes. In amber suppressor strains of *E. coli*, the resulting Ig domain-gene III fusions become anchored in the phage coat.

A selection process based on protein affinity can be applied to any high-affinity binding reagents such as antibodies, antigens, receptors and ligands (see, for example, Winter and Milstein, (1991) Nature 349:293-299, the entire contents of which are incorporated herein by reference). Thus the selection of the highest affinity binding protein displayed on bacteriophage is coupled to the recovery of the gene encoding that protein. Ig-displaying phage can be affinity selected by binding to cognate binding partners covalently coupled to beads or adsorbed to plastic surfaces in a manner similar to ELISA or solid phase radioimmunoassays. While almost any plastic surface will adsorb protein antigens, some commercial products are especially formulated for this purpose, such as Nunc Immunotubes.

Ribosomal display libraries involve polypeptides synthesized de novo in cell-free translation systems and displayed on the surface of ribosomes for selection purposes (Hanes and Pluckthun, (1997) Proc Natl Acad Sci USA 94:4937-4942; He and Taussig, (1997) Nucl Acids Res 25:5132-5134). The "cell-free translation system" comprises ribosomes, soluble enzymes required for protein synthesis (usually from the same cell as the ribosomes), transfer RNAs, adenosine triphosphate, guanosine triphosphate, a ribonucleoside triphosphate regenerating system (such as phosphoenol pyruvate and pyruvate kinase), and the salts and buffer required to synthesize a protein encoded by an exogenous mRNA. The translation of polypeptides can be made to occur under conditions which maintain intact polysomes, i.e. where ribosomes, mRNA molecule and translated polypeptides are associated in a single complex. This effectively leads to "ribosome display" of the translated polypeptide.

For selection, the translated polypeptides, in association with the corresponding ribosome complex, are mixed with a target molecule which is bound to a matrix (e.g. Dynabeads). The target molecule may be any compound of interest (or a portion thereof) such as a DNA molecule, a protein, a receptor, a cell surface molecule, a metabolite, an antibody, a hormone or a virus. The ribosomes displaying the translated polypeptides will bind the target molecule and these complexes can be selected and the mRNA re-amplified using RT-PCR.

Although there are several alternative approaches to modify binding molecules the general approach for all displayed proteins conforms to a pattern in which individual binding reagents are selected from display libraries by affinity to their cognate receptor. The genes encoding these reagents are modified by any one or combination of a number of in vivo and in vitro mutation strategies and constructed as a new gene pool for display and selection of the highest affinity binding molecules.

BDM Dimers

In one example, the BDM moiety of the molecule is dimer of BDM monomers. Dimer formation may occur naturally or be facilitated by use of a linker. For example, where the BDM is a CTLA-4 VLD, dimerization may occur through a disulphide bond between cysteine residues ($Cys^{120}$) in the two stalks if these sequences are retained.

Alternatively, a linker can be used to couple BDM monomers (e.g. CTLA-4 monomers) together. This same principle can also be used to link a number of BDM monomers together in tandem to form a string. The linker can facilitate enhanced flexibility, and/or reduce the steric hindrance between any two monomers. The linker can be of natural origin.

Other types of linkers that can be used are those described further below, including the (Gly-Gly-Gly-Gly-Ser)n linker (SEQ ID NO: 33).

In Vitro Expression of Soluble Forms of CTLA-4

Neither the extracellular domains nor V-like domains (VLDs) of human CTLA-4 molecule have been successfully expressed as soluble monomers in bacterial cells, presumably due to aggregation of the expressed proteins (Linsley P S et al, (1995) J. Biol. Chem 270:15417-24). Expression of the extracellular N-terminal domain (Met1 to Asp124, comprising Cys120) in *E. coli* results in production of a dimeric 28 kDa MW protein, in which two CTLA-4 V-like domains are joined by a disulphide linkage at Cys120. Truncation at Val114 removes these cysteines and was intended to enable expression of a 14 kDa VLD in soluble, monomeric form. However, the product aggregated and it was concluded that hydrophobic sites, which were normally masked by glycosylation, were now exposed and caused aggregation (Linsley P S et al, (1995) J. Biol. Chem 270:15417-24).

There have been some reports of successful expression of monomeric, glycosylated CTLA-4 extracellular domains in eukaryotic expression systems (i.e. CHO cells and the yeast *Pichia pastoris*; Linsley P S et al, (1995) J. Biol. Chem 270:15417-24; Metzler W J et al (1997) Nat Struct Biol 4(7):527-31; Gerstmayer B et al. (1997) FEBS Lett 407(1): 63-8). Glycosylation in these eukaryotic expression systems is presumed to occur at the two N-linked glycosylation sites in the VLD (Asn76 and Asn108). However, high yields have only been described for expression of a gene encoding a CTLA-4 VLD fused to Ig-CH2/CH3 domains which produces a dimeric recombinant protein with 2 CTLA-4 VLDs attached to an Fc subunit (WO 95/01994 and AU 16458/95). AU 60590/96 describes mutated forms of CTLA-4 VLDs with single amino acid replacements of the first tyrosine (Y) in the MYPPPY (SEQ ID NO: 34) surface loop which retain and modifies the affinity for the natural CD80 and CD86 ligands. AU 60590/96 describes the preferred soluble form of CTLA-4 VLDs as a recombinant CTLA-4/Ig fusion protein expressed in eukaryotic cells and does not solve the aggregation problem in prokaryote expression systems. EP 0757099A2 describes the use of CTLA-4 mutant molecules, for example the effect of changes on ligand binding of mutations in the BL sequence.

B7-1 (CD80) Protein and B7-2 (CD86) Protein

The B7 protein is a peripheral membrane protein found on activated antigen presenting cells (APC) that, when paired with either a CD28 or CD152 (CTLA-4) surface protein on a T-cell, can produce a co-stimulatory signal or a co-inhibitory signal to enhance or decrease the activity of a MHC-TCR signal between the APC and the T cell, respectively. As well as being present on activated APCs, B7 is also found on T-cells.

The B7 protein comprises a number of family members which include B7-1, B7-2, B7-DC, B7-H1 to B7-H7. The B7-1 protein is also referred to as CD80 and binds to CD28 and CTLA-4 (cytotoxic T-lymphocyte-associated protein 4). The Uniprot reference of the human sequence is P33681.

In one example, the BDM binds to B7-1 human protein. In one example the BDM binds to the B7-2 protein.

Sclerostin

Sclerostin is a secreted glycoprotein with a C-terminal cysteine knot-like domain and sequence similarity to the DAN (differential screening-selected gene aberrative in neuroblastoma) family of bone morphogenic protein (BMP) antagonists. Sclerostin is produced by the osteocyte and has anti-anaebolic effects of bone formation. The Uniprot reference of the human sequence is Q9BQB4.

In one example, the BDM binds to sclerostin human protein.

Pharmacologically Active Proteins

The types of protein completed in the present disclosure are those which are pharmacologically active. Such proteins include an antibody (e.g. full-length antibody) or immunoglobulin antigen-binding fragment or non-antibody proteins as described herein.

The term "pharmacologically active" means a substance which is determined to have activity that affects a medical parameter or a disease state or causes activation of a cell involved in the immune response. The protein may be an agonist protein, an antagonist protein or mimetic. The protein may also be a therapeutic antibody.

The terms "mimetic" or "agonist" refer to proteins (or peptides) having biological activity comparable to the natural protein (e.g. EPO or G-CSF).

Exemplary proteins that are suitable in accordance with the present disclosure include, but are not limited to a blood clotting factor, an anticalin, a toxoid, a human serum albumin, a collagen binding protein, a TNF-alpha receptor binding protein, an integrin binding protein, a VEGF or mimetic thereof, an EPO or mimetic thereof, a C4 binding protein, a urokinase receptor antagonist, a lymphokine, a cytokine, an osteoprotegerin (OPG), or the extracellular domain of a protein selected from programmed cell death 1 protein (PD1), programmed death ligand 1 (PD-L1), NKG2D, MHC class I polypeptide related sequence A (MICA), MHC class I polypeptide related sequence B (MICB), UL16 binding protein (ULBP).

Blood clotting factors are known in the art, examples include factor VIII and factor IX which are associated with haemophilia.

In one example, the toxoid is botulinium toxoid. The toxoid may be botulinium type A or botulinium type B. Synthetic forms of botulinium toxoid are also contemplated.

In one example, the lymphokine is IL-2 or GM-CSF or mimetic thereof.

In one example, the cytokine is a G-CSF or mimetic thereof or stem cell factor or mimetic thereof.

In one example, the protein is coupled to an BDM which binds to human serum albumin so that the half-life of the protein is extended in vivo compared to the protein without the presence of the BDM.

Antibodies

In certain examples, the multi-specific molecule comprises a full length antibody. In one example, the antibody is a humanised antibody. In another example, the antibody is a human antibody. In another example, the antibody is a chimeric antibody.

The term 'humanized antibody' shall be understood to refer to a subclass of chimeric antibodies having an antigen binding site or variable region derived from an antibody from a non-human species and the remaining antibody structure based upon the structure and/or sequence of a human antibody. In a humanized antibody, the antigen-binding site generally comprises the complementarity determining regions (CDRs) from a non-human antibody grafted onto appropriate framework regions (FRs) in the variable regions of a human antibody and the remaining regions from a human antibody. Antigen binding sites may be wild-type (i.e., identical to those of the non-human antibody) or modified by one or more amino acid substitutions. In some instances, FR residues of the human antibody are replaced by corresponding non-human residues. In general the humanised antibody will comprise substantially all of at least one, and typically two variable domains in which all or substantially all of the CDR regions correspond to those of a non-human immunoglobulin and all or substantially all of the FR regions are those of a human immunoglobulin consensus sequence.

A humanised antibody of the present disclosure will also contain an immunoglobulin constant region (Fc), typically that of a human immunoglobulin (Jones et al., (1986) Nature, 321:522-525; Riechmann et al., (1988) Nature, 332:323-329; and Presta, (1992) Curr. Op. Struct. Biol. 2:593-596).

Methods for humanizing non-human antibodies or parts thereof (e.g., variable regions) are known in the art. Humanization can be essentially performed following the method of Winter and co-workers (Jones et al., Nature, 321:522 525 (1986); Riechmann et al., Nature, 332:323 327 (1988)); Verhoeyen et al. Science, 239:1534 1536 (1988)) or as described in U.S. Pat. No. 5,225,539, or U.S. Pat. No. 5,585,089. Other methods for humanizing an antibody are not excluded.

The term 'human antibody' as used herein refers to antibodies having variable regions (e.g. VH, VL) and, optionally constant regions derived from or corresponding to sequences found in humans, e.g. in the human germline or somatic cells. The 'human' antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4, 5 or 6 of the residues of the antibody, e.g. in 1, 2, 3, 4, 5 or 6 of the residues making up one or more of the CDRs of the antibody). These 'human antibodies' do not actually need to be produced by a human, rather, they can be produced using recombinant means and/or isolated from a transgenic animal (e.g., mouse in which the endogenous immunoglobulin genes have been partially or completely inactivated) comprising nucleic acid encoding human antibody constant and/or variable regions (e.g., as described above). Human antibodies can be produced using various techniques known in the art, including phage display libraries (e.g., as described in U.S. Pat. No. 5,885,793).

Human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (e.g., as described in U.S. Pat. No. 5,565,332).

Humanized immunoglobulins, including humanized antibodies, have been constructed by means of genetic engineering. Most humanized immunoglobulins that have been previously described have comprised a framework that is identical to the framework of a particular human immunoglobulin chain (i.e., an acceptor or recipient), and three CDRs from a non-human (donor) immunoglobulin chain. Humanization can also include criteria by which a limited number of amino acids in the framework of a humanized immunoglobulin chain are identified and chosen to be the same as the amino acids at those positions in the donor rather than in the acceptor, in order to increase the affinity of an antibody comprising the humanized immunoglobulin chain.

Humanized antibodies generally have at least three potential advantages over mouse or chimeric antibodies for use in human therapy. Because the effector portion of an antibody is human, it is believed to interact better with the other parts of the human immune system (e.g., destroy the target cells more efficiently by complement-dependent cytotoxicity (CDC) or antibody-dependent cellular cytotoxicity (ADCC)). Additionally, the human immune system should not recognize the framework or constant region of the humanized antibody as foreign, and therefore the antibody response against such an injected antibody should be less than against a totally foreign mouse antibody or a partially foreign chimeric antibody. Finally, mouse antibodies are known to have a half-life in the human circulation that is much shorter than the half-life of human antibodies. Humanized antibodies can, presumably, have a half-life more similar to naturally-occurring human antibodies, allowing smaller and less frequent doses to be given.

It will be appreciated that any full length antibody which binds to a desired target can be used in the present disclosure. In one example, the full length antibody is further affinity matured before coupling to the BDM.

In another example, the full length immunoglobulin is a non-human immunoglobulin. In one example, the immunoglobulin is a mouse, rat, hamster, cat, dog, horse or cow immunoglobulin.

Conventional methods can be used to prepare antibodies. For example, by using a peptide or full length target protein, polyclonal antisera or monoclonal antibodies can be made using standard methods. A mammal, (e.g., a mouse, hamster, or rabbit) can be immunized with an immunogenic form of the peptide that elicits an antibody response in the mammal. Techniques for conferring enhanced immunogenicity on a peptide include conjugation to carriers or other techniques well known in the art. For example, the protein or peptide can be administered in the presence of adjuvant. The progress of immunization can be monitored by detection of antibody titres in plasma or serum. Standard ELISA or other immunoassay procedures can be used with the immunogen as antigen to assess the levels of antibodies. Folio wing immunization, antisera can be obtained and, if desired, polyclonal antibodies isolated from the sera.

The antibodies can be generated in cell culture, in phage, or in various animals, including but not limited to cows, rabbits, goats, mice, rats, hamsters, guinea pigs, sheep, dogs, cats, monkeys, chimpanzees, apes. Therefore, an antibody useful in the present disclosure is typically a mammalian antibody. Phage techniques can be used to isolate an initial antibody or to generate variants with altered specificity or avidity characteristics. Such techniques are routine and well known in the art. In one example, the antibody is one produced by recombinant means known in the art. For example, a recombinant antibody can be produced by transfecting a host cell with a vector comprising a DNA sequence encoding the antibody. One or more vectors can be used to transfect the DNA sequence expressing at least one VL and one VH region in the host cell. Exemplary descriptions of recombinant means of antibody generation and production include: Delves, Antibody Production: Essential Techniques (Wiley, 1997); Shephard, et al., Monoclonal Antibodies (Oxford University Press, 2000); and Goding, Monoclonal Antibodies: Principles and Practice (Academic Press, 1993).

It may be desirable to modify the antibody with respect to effector function, as to enhance the effectiveness of the antibody in vivo. For example, cysteine residue(s) may be introduced into the Fc region, thereby allowing interchain disulphide bond formation in this region. The antibody thus generated can have improved internalisation capability and/or increased complement mediated cell killing and antibody-dependent cellular cytotoxicity (ADCC). See Caron et al., (1992) J. Exp Med., 176: 1191-1195 and Shopes, (1992) J. Immunol., 148: 2918-2922.

Antibody Fragments

Antibody fragments comprise a portion of an intact antibody and can include the antigen binding or variable region of an intact antibody. Examples of antibody fragments suitable for use in the present disclosure include Fab, F(ab')$_2$, Fab', scFv, di-scFv, or chemically linked F(ab')$_2$. In a particular example, the antibody fragment is an Fab.

An Fv refers to antibody fragment which contain a complete antigen-recognition and binding site. This region consists of a dimer of one heavy and one light chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody fragment.

An Fab fragment contains an Fv and also contains the constant domain of the light chain and the first constant domain (CH1) of the heavy chain. Fab fragments differ from Fab' fragments by the addition of a few residues at the carboxy terminus of the heavy chain CH1 domain include one or more cysteines from the antibody hinge region. F(ab')$_2$ fragments are produced as pairs of Fab' fragments which have hinge cysteines between them.

Chemically linked F(ab')$_2$ are bi-specific molecules formed by pairing two different Fab' fragments together each of which has a different binding specificity. Techniques for generating bi-specific antibodies from antibody fragments have been described in the literature. For example, bi-specific antibodies can be prepared using chemical linkage. Brennan et al (1985) Science 229:81 describe a procedure wherein intact antibodies are proteolytically cleaved to generate F(ab')$_2$ fragments. These fragments are reduced in the presence of dithiol complexing agent sodium arsenite to stabilise vicinal dithiols and prevent intermolecular disulphide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bi-specific antibody.

Production of the Multi-Specific Molecules

The present disclosure also provides methods for making a multi-specific molecule of the present disclosure.

Expression of the molecules can be in prokaryotic or eukaryotic cells. Prokaryotes most frequently are represented by various strains of bacteria. The bacteria may be a gram positive or a gram negative. Typically, gram-negative bacteria such as *E. coli* are preferred. Other microbial strains may also be used.

Sequences encoding the molecules can be cloned into vectors designed for expressing foreign sequence in prokaryotic cells such as *E. coli*. These vectors can include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., (1977) Nature 198:1056), the tryptophan (trp) promoter system (Goeddel, et al., (1980) Nucleic Acids Res. 8:4057) and the lambda derived PL promoter and N-gene ribosome binding site (Shimatake, et al., (1981) Nature 292:128).

Such expression vectors will also include origins of replication and selectable markers, such as a beta-lactamase or neomycin phosphotransferase gene conferring resistance to antibiotics, so that the vectors can replicate in bacteria and cells carrying the plasmids can be selected for when grown in the presence of antibiotics, such as ampicillin or kanamycin.

The expression of antibodies in unicellular organisms such as *E. coli* and yeast is well established in the art. For a review, see for example André Frenzel et al (2013) Front Immunol 4:217. Expression in eukaryotic cells in culture is also known to those skilled in the art as an option for production of the bi-specific molecules described herein, see for recent reviews, for example Raff, M. E. (1993) Curr. Opinion Biotech. 4: 573-576; Trill J. J. et al. (1995) Curr. Opinion Biotech 6: 553-560.

Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or 5,530,101.

Systems for cloning and expression of a polypeptide in a variety of different host cells are well known. Suitable host cells include bacteria, mammalian cells, yeast and baculovirus systems. Suitable host cells include bacteria, mammalian cells, yeast and baculovirus systems. Mammalian cell lines available in the art for expression of a heterologous polypeptide include Chinese hamster ovary cells, HeLa cells, Human Embryonic Kidney Cells, baby hamster kidney cells, NSO mouse melanoma cells and many others. Suitable hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Following isolation, the nucleic acid is inserted operably linked to a promoter in an expression construct or expression vector for further cloning (amplification of the DNA) or for expression in a cell-free system or in cells. Vectors can be plasmids, viral e.g. 'phage, or phagemid, as appropriate.

To produce the vector constructs of the present disclosure, a nucleic acid sequence encoding an antibody light chain sequence, heavy chain sequence, and a linker sequence as described herein and an BDM sequence is cloned by standard methods into a suitable vector.

In some examples, the BDM will be cloned at a C-terminal end of the antibody light chain sequence. In some examples, the BDM will be cloned at a C-terminal end of the antibody heavy chain sequence. In some examples, the BDM will be cloned at an N-terminal end of the antibody light chain sequence. In some examples, the BDM will be cloned at a N-terminal end of the antibody heavy chain sequence. In some examples, BDMs will be cloned at both an N-terminal and a C-terminal ends of the antibody light chain sequence. In some examples, BDMs will be cloned at both an N-terminal and a C-terminal ends of the antibody heavy chain sequence. In some examples, BDMs will be cloned at both an N-terminal and a C-terminal ends of both the antibody light chain sequence and heavy chain sequence. In some examples, the nucleic acid sequence encoding the antibody heavy or light chain and BDM is provided in one vector and the other antibody chain is provided on another vector. In other examples, a nucleic acid sequence encoding an antibody light chain sequence, a linker sequence and a BDM sequence are cloned into one vector and a nucleic acid sequence encoding an antibody heavy chain sequence, a linker sequence and a BDM sequence are cloned into another vector. Alternatively a bicistronic vector may be used whereby both antibody light and heavy chains are expressed on the same vector. In certain examples, the heavy and light chain coding sequences (one of which will also include the BDM) may reside on a single vector, for example in tow expression cassettes in the same vector.

Nucleic acid sequences encoding the molecules can also be inserted into a vector designed for expressing foreign sequences in a eukaryotic host. The regulatory elements of the vector can vary according to the particular eukaryotic host.

Useful expression vectors, for example, can consist of segments of chromosomal, non-chromosomal and synthetic DNA sequences. Suitable vectors include derivatives of SV40 and known bacterial plasmids, e.g., *E. coli* plasmids col El, Pcr1, Pbr322, Pmb9 and their derivatives, plasmids such as RP4; phage DNAs, e.g., the numerous derivatives of phage A, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Nucleic acid sequences encoding the molecules can integrate into the genome of the eukaryotic host cell and replicate as the host genome replicates. Alternatively, the vector carrying the nucleic acid sequences can contain origins of replication allowing for extrachromosomal replication.

As used herein, the term 'promoter' is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term 'operably linked to' means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, polyadenylation sequences and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells sub-cloned for growth in suspension culture; baby hamster kidney cells (BHK, ATCC CCL 10); or Chinese hamster ovary cells (CHO).

Means for introducing the isolated nucleic acid or expression construct comprising same into a host cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, retroviral transduction, electroporation and microparticle bombardment such as by using DNA-coated tungsten or gold particles (Agracetus Inc., WI, USA) amongst others.

The introduction can be followed by causing or allowing expression from the nucleic acid, e.g. by culturing host cells under conditions for expression.

The present disclosure also provides a method which comprises using a construct as stated above in an expression system in order to express the antibody or immunoglobulin antigen-binding fragment chains and BDM.

The present disclosure also provides a recombinant host cell which comprises one or more nucleic acid sequences described herein. The host cells used to produce the protein may be cultured in a variety of media, depending on the cell type used. Commercially available media such as Ham's FIO (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

A wide variety of host/expression vector combinations can be employed in expressing the nucleic acid sequences of this disclosure. Useful expression vectors, for example, can consist of segments of chromosomal, non-chromosomal and synthetic DNA sequences. Suitable vectors include derivatives of SV40 and known bacterial plasmids, e.g., *E. coli* plasmids col El, Pert, Pbr322, Pmb9 and their derivatives, plasmids such as RP4; phage DNAs, e.g., the numerous derivatives of phage \ e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like Also provided herein is a recombinant host cell which comprises one or more polynucleotides described herein.

Any of a wide variety of expression control sequences-sequences that control the expression of a nucleic acid sequence operatively linked to it—can be used in these vectors to express the nucleic acid sequences. Such useful expression control sequences include, for example, the early or late promoters of SV40, CMV, vaccinia, polyoma or adenovirus, the lac system, the tip system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

One skilled in the art will be able to select the proper vectors, expression control sequences, and hosts without undue experimentation to accomplish the desired expression without departing from the scope of this disclosure. For example, in selecting a vector, the host must be considered because the vector must function in it. The vector's copy number, the ability to control that copy number, and the expression of any other proteins encoded by the vector, such as antibiotic markers, will also be considered. One of ordinary skill in the art can select the proper vectors, expression control sequences, and hosts to accomplish the desired expression without departing from the scope of this application. For example, in selecting a vector, the host is considered because the vector functions in it. The vector's copy number, the ability to control that copy number, and the expression of any other proteins encoded by the vector, such as antibiotic markers, can also be considered.

The present disclosure provides an isolated polynucleotide (nucleic acid) encoding a polypeptide as described herein, vectors containing such polynucleotides, and host cells and expression systems for transcribing and translating such polynucleotides into polypeptides. The present disclosure also provides constructs in the form of plasmids, vectors, transcription or expression cassettes as described elsewhere herein which comprise at least one polynucleotide as above.

The present disclosure also provides a host cell containing one or more polynucleotides as disclosed herein.

Following production by expression, the molecule can be isolated and/or purified using any suitable technique. Encoding nucleic acid molecules and vectors described herein can be provided isolated and/or purified, e.g., from their natural environment, in substantially pure or homogeneous form, or, in the case of nucleic acid, free or substantially free of nucleic acid or genes origin other than the sequence encoding a polypeptide with the required function. Nucleic acid can comprise DNA or RNA and can be wholly or partially synthetic.

For expressing the nucleic acid sequences in *Saccharomyces cerevisiae*, the origin of replication from the endogenous yeast plasmid, the 2p circle can be used. (Broach, (1983) Meth. Enz. 101:307). Alternatively, sequences from the yeast genome capable of promoting autonomous replication can be used (see, for example, Stinchcomb et al., (1979) Nature 282:39); Tschemper et al., (1980) Gene 10:157; and Clarke et al., (1983) Meth. Enz. 101:300).

Transcriptional control sequences for yeast vectors include promoters for the synthesis of glycolytic enzymes (Hess et al., (1968) J. Adv. Enzyme Reg. 7:149; Holland et al., (1978) Biochemistry 17:4900). Additional promoters known in the art include the CMV promoter provided in the CDM8 vector (Toyama and Okayama, (1990) FEBS 268: 217-221); the promoter for 3-phosphoglycerate kinase (Hitzeman et al., (1980) J. Biol. Chem. 255:2073), and those for other glycolytic enzymes.

Expression of the polypeptides can be detected by methods known in the art. For example, the molecules can be detected by Coomassie staining SDS-PAGE gels and immunoblotting using antibodies that bind either the antibody, immunoglobulin antigen-binding fragment or BDM. Protein recovery can be performed using standard protein purification means, e.g., affinity chromatography or ion-exchange chromatography, to yield substantially pure product (R. Scopes in: "Protein Purification, Principles and Practice", Third Edition, Springer-Verlag (1994)).

The present disclosure also provides a method of producing a multi-specific molecule of the present disclosure which method comprises the steps of:

(i) providing a vector(s) comprising polynucleotides encoding the proteins (e.g. antibody) and BDM;

(ii) transforming a mammalian host cells (e.g. CHO) with the vector;

(iii) culturing the host cells of step (b) under conditions conducive to the secretion of the proteins from the host cell into the culture media; and (iv) recovering the secreted proteins of step (iii).

In one example, the method comprises:

(i) providing a first vector encoding a heavy chain of the multi-specific molecule;

(ii) providing a second vector encoding a light chain of the multi-specific molecule; and (iii) transforming a mammalian host cell (e.g. CHO) with said first and second vectors.

Synthetic Production

A nucleic acid encoding a polypeptide of the present disclosure can be prepared synthetically in addition to, or rather than, cloned. The nucleic acid can be designed with the appropriate codons for the polypeptide moieties (e.g. immunoglobulin and BDM). In general, one will select preferred codons for an intended host if the sequence will be used for expression. In general one will select preferred codons for the intended host if the sequence will be used for expression. The complete polynucleotide can be assembled from overlapping oligonucleotides prepared by standard methods and assembled into a complete coding sequence.

See, e.g., Edge, Nature, 292:756 (1981); Nambair et al., Science, 223:1299 (1984); Jay et al., J. Biol. Chem., 259: 6311 (1984).

Isolation of Proteins

Methods for isolating a polypeptide are known in the art and/or described herein.

Where a polypeptide is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the polypeptide, e.g., using continuous centrifugation.

The polypeptides prepared from the host cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

In some examples, a polypeptide of the present disclosure is fused to a heterologous amino acid sequence, without affecting the biological activity (i.e. binding to its targets), such as for instance a signal sequence or an affinity tag.

The skilled artisan will also be aware that a polypeptide can be modified to include an affinity tag to facilitate purification or detection, e.g., a poly-histidine tag, e.g., a hexa-histidine tag (SEQ ID NO: 31), or an influenza virus hemagglutinin (HA) tag, or a Simian Virus 5 (V5) tag, or a FLAG tag, or a glutathione S-transferase (GST) tag. The resulting polypeptide is then purified using methods known in the art, such as, affinity purification. For example, a polypeptide comprising a hexa-his tag (SEQ ID NO: 31) is purified by contacting a sample comprising the polypeptide with nickel-nitrilotriacetic acid (Ni-NTA) that specifically binds a hexa-his tag SEQ ID NO: 31) immobilized on a solid or semi-solid support, washing the sample to remove unbound protein, and subsequently eluting the bound protein.

Coupling of the Pharmacologically Active Protein and BDMs

Coupling of the pharmacologically active protein or peptide and at least BDM according to present disclosure can be prepared using chemical linkage (Brennan et al (1985) Science 229:81) or chemical coupling (Shalaby et al (1992) J Exp Med 175:217-225) or gene fusion.

Additionally, fusion or linkage between a protein (e.g. antibody) and a BDM may be achieved by conventional covalent or ionic bonds, protein fusions, or heterobifunctional cross-linkers, e.g., carbodiimide, glutaraldehyde, and the like. Conventional inert linker sequences (e.g. peptide linkers) which simply provide for a desired amount of space between the protein and BDM may also be used. The design of such linkers is well known to those of skill in the art and is described for example in U.S. Pat. Nos. 8,580,922; 5,525,491; and 6,165,476.

A variety of coupling or cross-linking agents can be used for covalent conjugation of proteins. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky el al. (1984) J. Exp. Med 160 1686, Liu, M A et al. (1985) Proc. Natl. Acad. Sci. USA 82 8648). Other methods include those described in Paulus (1985) Behring Ins Mitt No 78, 1 18-132, Brennan et al. (1985) Science 229 81-83 and Glennie et al. (1987). J Immunol 39 2367-2375).

The linker can facilitate enhanced flexibility, and/or reduce steric hindrance between any two proteins. The linker can be of natural origin, such as a sequence determined to exist in random coil between two domains of a protein. An exemplary linker sequence is the linker found between the C-terminal and N-terminal domains of the RNA polymerase alpha subunit. Other examples of naturally occurring linkers include linkers found in the 1CI and LexA proteins.

Within the linker, the amino acid sequence may be varied based on the preferred characteristics of the linker as determined empirically or as revealed by modelling. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. In some cases, particularly when it is necessary to span a longer distance between subunits or when the domains must be held in a particular configuration, the linker may optionally contain an additional folded domain.

In some examples it is preferable that the design of a linker involve an arrangement of domains which requires the linker to span a relatively short distance, preferably less than about 10 Angstroms (Å). However, in certain embodiments, linkers span a distance of up to about 50 Å or more.

The term 'peptide linker' refers to a short peptide fragment that connects or couples the protein and the BDM moieties of the polypeptide of the multi-specific molecule. The linker is preferably made up of amino acids linked together by peptide bonds. For example, the peptide linker can comprise small amino acid residues or hydrophilic amino acid residues (e.g. glycine, serine, threonine, proline, aspartic acid, asparagine, etc.). For example, the peptide linkers are peptides with an amino acid sequence with a length of at least 5 amino acids, or with a length of about 5 to about 100 amino acids, or with a length of about 10 to 50 amino acids, or a length of about 10 to 15 amino acids.

In one example, the linker is made up of a majority of amino acids that are sterically unhindered such as glycine and alanine. Thus in a further example, the linkers are polyglycines, polyalanines or polyserines.

One skilled in the art would appreciate that many commonly used peptide linkers may be used in embodiments of the present disclosure. In certain embodiments, the short peptide linkers may comprise repeat units to increase the linker length. For example, a double, triple or quadruple repeated linker. In one example, the linker comprises a formula (Gly-Gly-Gly-Gly-Ser)n (SEQ ID NO: 35) or comprising the formula (Ser-Gly-Gly-Gly-Gly)n Ser (SEQ ID NO: 36) wherein n is a number from 3 to 6.

In one example, the linker comprises or consist of the sequence

SGGGGSGGGGSGGGGS (SEQ ID NO: 16)

or

SGGGGSGGGGSGGGGSGGGGS. (SEQ ID NO: 17)

Non-peptide linkers are also possible. For example, alkyl linkers such as —NH—$(CH_2)_s$—C(O)—, wherein s=2-20 could be used. These alkyl linkers may be further substituted by any non-sterically hindering group such as lower alkyl (e.g. $C_1$-$C_6$), lower acyl, halogen (e.g. Cl, Br), CN, $NH_2$, phenyl. An exemplary non-peptide linker is a PEG linker having a molecular weight of 100 to 5000 kD, preferably 100 to 500 kD.

Examples of other linkers which are suitable for use include GSTVAAPS (SEQ ID NO: 37), TVAAPSGS (SEQ ID NO: 38) or GSTVAAPSGS (SEQ ID NO: 39) or multiples of such linkers. Other examples include (TVSDVP)n (GS)m wherein n=1 and m=1 or wherein n=2 and m=1 or wherein n=2 and m=0 (SEQ ID NO: 40, 41 and 42, respectively, in order of appearance).

In another example, the linker is GS.

Assaying Polypeptide Activity

The protein (or peptide) and BDM moieties of the present disclosure can be assayed by various means according to known methods. Such assays may include functional assays e.g. cell killing assays, cAMP or calcium flux assays or binding assays e.g. ELISA or competition assays.

The type of functional assays employed will depend on the targets to which the protein or peptide and BDM moieties of the polypeptide bind.

Half-life assays may also be employed. Such methods are known in the art. Two methods commonly used to determine a protein's half-life are the radioactive pulse-chase analysis and the cycloheximide chase (Zhou P (2004) Methods Mol. Biol. 284:67-77.

Measuring Binding Affinity

Binding of epitopes can be measured by conventional by conventional antigen binding assays, such as ELISA, by fluorescence based techniques, including FRET, or by techniques such as surface plasmon resonance which measure the mass of molecules. Specific binding of an antigen binding protein (e.g. BDM) to an antigen or epitope can be determined by suitable assay, including, for example, Scatchard analysis and/or competitive binding assays such as radioimmunoassay (RIA), enzyme immunoassays such as ELISA and sandwich competition assays.

Competition assays such as surface plasmon resonance assays can be used to determine whether a BDM which has been engineered to bind a particular target is capable of doing so. By way of illustration, a BDM can be engineered to bind to the stem cell factor receptor (CSFR or c-kit receptor) and tested for its ability to compete with binding of the natural ligand (c-kit). In vitro competition assays for determining the ability of a modified BDM to compete for binding to a target as well as determining the dissociation constant ($K_D$) are known in the art.

The binding affinity or dissociation constant ($K_D$) of the interaction between the protein or BDM moiety of the polypeptide and its respective target can be measured by a number of methods known in the art. Such methods include, but are not limited to, fluorescence titration, competition ELISA, calorimetric methods, such as isothermal titration calorimetry (ITC) and surface plasmon resonance (BIAcore) or Bio-layer interferometry (e.g. Blitz system (ForteBio).

A preferred surface plasmon resonance assay is BIAcore which is known in the art.

Most binding moieties have $K_D$ values in the low micromolar ($10^{-6}$) to nanomolar ($10^{-7}$ to $10^{-9}$) range. High affinity binding moieties are generally considered to be in the low nanomolar range ($10^{-9}$) with very high affinity binding moieties being in the picomolar ($10^{-12}$) range.

The complex formation between the respective moiety and its target is influenced by many different factors such as the concentrations of the respective binding partners, the presence of competitors. pH and the ionic strength of the buffer system used, and the experimental method used for determination of the $K_D$ (for example, fluorescence titration, competition ELISA or surface plasmon resonance) or even the mathematical algorithm which is used for evaluation of the experimental data.

It is therefore clear to the person skilled in the art that the $K_D$ values may vary within a certain experimental range, depending on the method and experimental setup that is used for determining the affinity of a particular immunoglobulin or BDM for a given target. This means that there may be a slight deviation in the measured KD values or a tolerance range depending on whether the KD value was determined by surface plasmon resonance (Biacore), by competition ELISA or by "direct ELISA".

In a preferred example, the KD value is determined by using surface plasmon resonance assays, e.g., using BIAcore surface plasmon resonance (BIAcore, Inc., Piscataway, N.J.) to an immobilised target.

Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of the protein or the BDM for unrelated amino acid sequences. Affinity of a protein or BDM to a target (e.g. protein antigen) can be, for example, from about 100 nanomolar (nM) to about 0.1 nM, from about 100 nM to about 1 picomolar (pM), or from about 100 nM to about 1 femtomolar (fM) or more.

In one example, the protein has an affinity measured by KD of about 200 nM or lower, about 100 nM or lower, about 50 nM or lower, about 25 nM or lower, about 10 nM or lower, of about 5 nM or lower, of about 1 nM or lower or of about 0.5 nM or lower.

In one example, the BDM has an affinity measured by KD of about 200 nM or lower, about 100 nM or lower, about 50 nM or lower, about 25 nM or lower, 10 nM or lower, of about 5 nM or lower, of about 1 nM or lower or of about 0.5 nM or lower.

Bio-layer interferometry is a label-free technology for measuring biomolecular interactions within the interactome. It is an optical analytical technique that analyses the interference pattern of white light reflected from two surfaces: a layer of immobilized protein on the biosensor tip, and an internal reference layer. Any change in the number of molecules bound to the biosensor tip causes a shift in the interference pattern that can be measured in real-time.

The binding between a ligand immobilized on the biosensor tip surface and an analyte in solution produces an increase in optical thickness at the biosensor tip, which results in a wavelength shift, Δλ which is a direct measure of the change in thickness of the biological layer. Interactions are measured in real time, providing the ability to monitor binding specificity, rates of association and dissociation, or concentration, with precision and accuracy.

Only molecules binding to or dissociating from the biosensor can shift the interference pattern and generate a response profile. Unbound molecules, changes in the refractive index of the surrounding medium, or changes in flow rate do not affect the interference pattern. This is a unique characteristic of bio-layer interferometry and extends its capability to perform in crude samples used in applications for protein-protein interactions, quantitation, affinity, and kinetics.

Target

The target according to the present disclosure is preferably an antigen. The antigen may be selected from a protein, a glycan, a lipid, a lipoprotein or nucleic acid. The protein may be a human protein, non-human protein (e.g. primate, canine, feline etc.), viral protein, yeast protein, bacterial protein, algae protein, plant protein or protozoal protein. The protein may be a soluble protein or membrane bound protein. Examples of soluble proteins include, but are not limited to transcription factors, antibodies, growth factors, blood proteins (e.g. albumin), or drugs (e.g. steroid, pharmaceutical drugs etc.). Types of membrane bound proteins include growth factor receptors, tumour markers, or markers which mediate transport into a cell (e.g. transferrin), or Fc receptor.

The nucleic acid target may be DNA, RNA or a combination of DNA and RNA.

More particularly, the target is an epitope present on the antigen. Persons skilled in the art will appreciate that an antigen may comprise a number of unique epitopes, each of which will be recognised by a protein (e.g. antibody) or BDM.

The polypeptide of the present disclosure can bind to different targets. In one example, the different targets are two or three different antigens. Each antigen may be present on different cells. In another example, the polypeptide may bind to two or three different targets (e.g. epitopes) on the same antigen. Preferably, the target to which protein binds, is different from the target to which the BDM binds.

The "target antigen" according to the present disclosure may be a protein, peptide, a glycoprotein, a polysaccharide, a glycan, a lipid, a lipoprotein or nucleic acid. Target antigens according to the present disclosure may be secreted or membrane bound. Such antigens may be derived from bacterial, mammalian (human and non-human), fungal, algael, protozoal sources. The protein may be a human protein, non-human protein (e.g. primate, canine, feline etc.), viral protein, yeast protein, bacterial protein, algae protein, plant protein or protozoal protein.

The reference to "first target antigen", "second target antigen" etc. being the same will be understood to mean that the pharmacologically active protein and the at least one BDM moiety bind to the same antigen but may bind to different epitopes present on the antigen.

Reference to the "first target antigen", "second target antigen" etc. being different will be understood to mean that the pharmacologically active protein moiety and the at least one BDM moiety bind to different antigens and thus different epitopes present on different cells.

(i) Bacterial Antigens

The antigen can be derived from bacteria, including but not limited to, *Helicobacter pylori, Chlamydia pneumoniae, Chlamydia trachomatis, Ureaplasma urealyticum, Mycoplasma pneumoniae, Staphylococcus* spp., *Staphylococcus aureus, Streptococcus* spp., *Streptococcus pyogenes, Streptococcus pneumoniae, Streptococcus viridans, Enterococcus faecalis, Neisseria meningitidis, Neisseria gonorrhoeae, Bacillus anthracis, Salmonella* spp., *Salmonella typhi, Vibrio cholera, Pasteurella pestis, Pseudomonas aeruginosa, Campylobacter* spp., *Campylobacter jejuni, Clostridium* spp., *Clostridium difficile, Mycobacterium* spp., *Mycobacterium tuberculosis, Treponema* spp., *Borrelia* spp., *Borrelia burgdorferi,* Leptospira spp., Hemophilus *ducreyi, Corynebacterium diphtheria, Bordetella pertussis, Bordetella parapertussis, Bordetella bronchiseptica,* hemophilus influenza, *Escherichia coli, Shigella* spp., *Erlichia* spp., and *Rickettsia* spp.

(ii) Viral Antigens

The antigen can be derived from viruses, including but not limited to, Influenza viruses, a Parainfluenza viruses, Mumps virus, Adenoviruses, Respiratory syncytial virus, Epstein-Barr virus, Rhinoviruses, Polioviruses, Coxsackieviruses, Echoviruses, Rubeola virus, Rubella virus, Varicell-zoster virus, Herpes viruses (human and animal), Herpes simplex virus, Parvoviruses (human and animal), Cytomegalovirus, Hepatitis viruses, Human papillomavirus, Alphaviruses, Flaviviruses, Bunyaviruses, Rabies virus, Arenaviruses, Filoviruses, HIV 1, HIV 2, HTLV-1, HTLV-II, FeLV, Bovine LV, FeIV, Canine distemper virus, Canine contagious hepatitis virus, Feline calicivirus, Feline rhinotracheitis virus, TGE virus (swine), and Foot and mouth disease.

(iii) Tumour Antigens

The target antigen may be a tumour associated antigen. Such tumour associated antigens include, but are not limited to, MUC-1 and peptide fragments thereof, protein MZ2-E, polymorphic epithelial mucin, folate-binding protein LK26, MAGE-1 or MAGE-3 and peptide fragments thereof, Human chorionic gonadotropin (HCG) and peptide fragments thereof, Carcinoembryonic antigen (CEA) and peptide fragments thereof, Alpha fetoprotein (AFP) and peptide fragments thereof, Pancreatic oncofetal antigen and peptide fragments thereof, CA 125, 15-3, 19-9, 549, 195 and peptide fragments thereof, Prostate-specific antigens (PSA) and peptide fragments thereof, Prostate-specific membrane antigen (PSMA) and peptide fragments thereof, Squamous cell carcinoma antigen (SCCA) and peptide fragments thereof, Ovarian cancer antigen (OCA) and peptide fragments thereof, Pancreas cancer associated antigen (PaA) and peptide fragments thereof, Her1/neu and peptide fragments thereof, gp-100 and peptide fragments thereof, mutant K-ras proteins and peptide fragments thereof, mutant p53 and peptide fragments thereof, nonmutant p53 and peptide fragments thereof, truncated epidermal growth factor receptor (EGFR), chimeric protein p210BCR-ABL, telomerase and peptide fragments thereof, survivin and peptide fragments thereof, Melan-A/MART-1 protein and peptide fragments thereof, WT1 protein and peptide fragments, LMP2 protein and peptide fragments, HPV E6 E7 protein and peptide fragments, Idiotype protein and peptide fragments, NY-ESO-1 protein and peptide fragments, PAP protein and peptide fragments, cancer testis proteins and peptide fragments, and 5T4 protein and peptide fragments.

(iv) Other Mammalian Antigens

The target antigen may be an antigen or epitope present on a cell located within the heart, blood system, lungs, intestine, stomach, rectum, prostate, thyroid, liver or oesophagus. The target antigen may be an antigen or epitope present on a secreted protein. Examples of secreted proteins include, but are not limited to hormones, enzymes, toxins and anticmicrobial, peptides. Alternatively, the antigen or epitope is present on a non-membrane bound protein.

Selective Binding

In one example, the molecule can bind selectively to cells that express two or more of the different target antigens of the multi-specific molecule over cells that express only one of the target antigens.

Such cell selectivity can be achieved by titrating the binding affinity of each moiety (e.g. protein or BDM) on the bi-specific or tri-specific such that each individual moiety bound insufficiently to its target to enable fluorescence activated cell sorting (FACS) or immunofluorescence labelling or cell killing or cells expressing that target in the absence of the other targets bound by the bi-specific or tri-specific but wherein the combination of the weak binding moieties prompt sufficient avidity of the bi-specific or tri-specific to enable selective binding of cells co-expressing the relevant target molecules compared to cells expressing only one such target, such that selective FACS sorting, immunofluorescent labelling or cell killing could be achieved.

Compositions

The multi-specific molecules of the present disclosure can be used as a composition when combined with a pharmaceutically acceptable carrier or excipient. Such pharmaceutical compositions are useful for administration to a subject in vivo.

Pharmaceutically acceptable carriers are physiologically acceptable to the administered patient and retain the therapeutic properties of the molecule with which it is administered. Pharmaceutically-acceptable carrier and their formulations are generally described in, for example, Remington pharmaceutical Sciences 18$^{th}$ edn. Ed. A Gennaro, Mack Publishing Co., Easton Pa. 1990). One exemplary carrier is physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the polypeptides from the administration site of one organ or portion of the body, to another organ, or portion of the body. Each carrier must be acceptable in the sense of being compatible with the other ingredients of the formulation and not injurious to the patient.

The pharmaceutically acceptable excipient may include a preservative or cyropreservative.

Pharmaceutical compositions can be formulated to be compatible with a particular route of administration, systemic or local.

In one example, the composition described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term 'parenteral' as used herein includes subcutaneous, intravenous, intramuscular, intraperitoneal, intrathecal, intraventricular, intrasternal, and intracranial injection or infusion techniques.

Methods for preparing a molecule into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this disclosure are particularly useful for parenteral administration, such as intravenous administration or administration into a body cavity or lumen of an organ or joint. The compositions for administration will commonly comprise a solution of polypeptide dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of proteins of the present disclosure in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Non-aqueous vehicles such as mixed oils and ethyl oleate may also be used. Liposomes may also be used as carriers. The vehicles may contain minor amounts of additives that enhance isotonicity and chemical stability, e.g., buffers, preservatives or additives.

Upon formulation, polypeptides of the present disclosure will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver compounds of the present disclosure.

For intravenous administration, suitable carriers include physiological saline, bacteriostatic water, Cremophor ELTM (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration.

Pharmaceutically acceptable carriers can contain a compound that stabilizes, increases or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting polypeptides from digestion are known in the art (see, e.g., Fix (1996) Pharm Res. 13:1760 1764; Samanen (1996) J. Pharm. Pharmacol. 48:119 135; and U.S. Pat. No. 5,391,377, describing lipid compositions for oral delivery of therapeutic agents).

Biodegradable, biocompatible polymers can be used, such as ethylene vinyl acetate, polyanhydrides, polyglycolic acid, collagen, polyorthoesters, and polylactic acid. Methods for preparation of such formulations are known to those skilled in the art. The materials can also be obtained commercially from Alza Corporation and Nova Pharmaceuticals, Inc. Liposomal suspensions (including liposomes targeted to cells or tissues using antibodies or viral coat proteins) can also be used as pharmaceutically acceptable carriers. These can be prepared according to methods known in the art, for example, as described in U.S. Pat. Nos. 4,235,871; 4,501, 728; 4,522,811; 4,837,028; 6,110,490; 6,096,716; 5,283, 185; 5,279,833; Akimaru (1995) Cytokines Mol. Ther. 1:197 210; Alving (1995) Immunol. Rev. 145: 5 31; and Szoka (1980) Ann. Rev. Biophys. Bioeng. 9:467). Biodegradable microspheres or capsules or other biodegradable polymer configurations capable of sustained delivery of small molecules including peptides are known in the art (see, e.g., Putney (1998) Nat. Biotechnol. 16:153 157).

Molecules of the present disclosure can be incorporated within micelles (see, e.g., Suntres (1994) J. Pharm. Pharmacol. 46:23 28; Woodle (1992) Pharm. Res. 9:260 265). The molecule can be attached to the surface of the lipid monolayer or bilayer. For example, molecules can be attached to hydrazide-PEG-(distearoylphosphatidy-I) ethanolamine-containing liposomes (see, e.g., Zalipsky (1995) Bioconjug. Chem. 6: 705 708). Alternatively, any form of lipid membrane, such as a planar lipid membrane or the cell membrane of an intact cell, e.g., a red blood cell, can be used. Liposomal and lipid-containing formulations can be delivered by any means, including, for example, intravenous, transdermal (see, e.g., Vutla (1996) J. Pharm. Sci. 85:5 8), transmucosal, or oral administration.

Compositions of the present disclosure can be combined with other therapeutic moieties or imaging/diagnostic moieties as provided herein. Therapeutic moieties and/or imaging moieties can be provided as a separate composition, or as a conjugated moiety. Linkers can be included for conjugated moieties as needed and have been described elsewhere herein.

The molecules disclosed herein may also be formulated as immunoliposomes. Liposomes containing the polypeptide are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Formulations for in vivo administration are sterile. Sterilization can be readily accomplished via filtration through sterile filtration membranes.

Compositions of the present disclosure can be administered with other therapeutic agents, e.g. chemotherapeutic agents. Chemotherapeutic agents are known in the art and include cytotoxic and cytostatic drugs. Non-limiting examples include paclitaxel, cisplatin, methotrexate, doxorubicin, fludarabine etc. Other therapeutic agents are contemplated depending on the condition to be treated.

One embodiment of the present disclosure contemplates the use of any of the pharmaceutical compositions of the present disclosure to make a medicament for treating a disorder. Medicaments can be packaged in a suitable pharmaceutical package with appropriate labels wherein the label is for the indication of treating a disorder in a subject.

Labelling and Detection

The present disclosure provides a molecule described herein labelled with an agent. In one example, the agent is an imaging/detectable moiety. In another example, the agent is a therapeutic moiety. Methods for labelling a polypeptide will be familiar to persons skilled in the art.

The term "label" or "labelled" is intended to encompass direct labelling of the protein (e.g. antibody) or BDM by coupling coupling (i.e. physically linking) a detectable substance to said protein or BDM, as well as indirect labelling by reactivity with another reagent that is directly labelled. The term also includes covalent or non-covalent coupling.

In one example, the molecule can be labelled with a toxin, a radionuclide, iron-related compound, a dye, an imaging agent or a fluorescent label or a chemotherapeutic agent.

Alternatively, the molecule can be labelled with detectable label, such as a radionuclide, iron-related compound, a dye, an imaging agent or a fluorescent agent for immunodetection of target antigens.

Non-limiting examples of radiolabels include, for example, $^{32}P$, $^{33}P$, $^{43}K$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{81}Rb/^{81m}Kr$, $^{87m}Sr$, $^{90}Y$, $^{97}Ru$, $^{99}Tc$, $^{100}Pd$, $^{101}Rh$, $^{103}Pb$, $^{105}Rh$, $^{109}Pd$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, 189Re, 191Os, 193Pt, $^{194}Ir$, $^{197}Hg$, $^{199}Au$, $^{203}Pb$, $^{211}At$, $^{212}Pb$, $^{212}Bi$, and $^{213}Bi$.

A variety of radionuclides are available for the production of radioconjugated proteins. Examples include, but are not limited to, low energy radioactive nuclei (e.g., suitable for diagnostic purposes), such as $^{13}C$, $^{15}N$, $^{2}H$, $^{125}I$, $^{123}I$, $^{99}Tc$, $^{43}K$, $^{52}Fe$, $^{67}Ga$, $^{68}Ga$, $^{111}In$ and the like. For example, the radionuclide is a gamma, photon, or positron-emitting radionuclide with a half-life suitable to permit activity or detection after the elapsed time between administration and localization to the imaging site. The present disclosure also encompasses high energy radioactive nuclei (e.g., for therapeutic purposes), such as $^{125}I$, $^{131}I$, $^{123}I$, $^{105}Rh$, $^{153}Sm$, $^{67}Cu$, $^{67}Ga$, $^{166}Ho$, $^{177}Lu$, $^{186}Re$ and $^{188}Re$. These isotopes typically produce high energy α- or β-particles which have a short path length. Such radionuclides kill cells to which they are in close proximity, for example neoplastic cells to which the conjugate has attached or has entered. They have little or no effect on non-localized cells and are essentially non-immunogenic. Alternatively, high-energy isotopes may be generated by thermal irradiation of an otherwise stable isotope, for example as in boron neutron-capture therapy (Guan et al., 1998). Other isotopes which may be suitable are described in Carter. (2001) Nature Reviews Cancer 1, 118-129, Goldmacher et al. (2011) Therapeutic Delivery 2; 397-416, Payne (2003) Cancer Cell 3, 207-212, Schrama et al, (2006) Nature Rev. Drug Discov. 5, 147-159, Reichert et al. (2007) Nature Reviews Drug Discovery 6; 349-356.

A toxin includes any agent that is detrimental to (e.g., kills) cells. Additional techniques relevant to the preparation of antibody immunotoxin conjugates are provided in for instance in U.S. Pat. No. 5,194,594 and may be utilised in the present disclosure. Non-limiting examples of toxins include, for example, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, tricothecenes, *Clostridium perfringens* phospholipase C (PLC), bovine pancreatic ribonuclease (BPR), antiviral protein (PAP), abrin, cobra venom factor (CVF), gelonin (GEL), saporin (SAP) viscumin.

Non-limiting examples of iron-related compounds include, for example, magnetic iron-oxide particles, ferric or ferrous particles, $Fe_2O_3$ and $Fe_3O_4$. Iron-related compounds and methods of labelling polypeptides, proteins and peptides can be found, for example, in U.S. Pat. Nos. 4,101,435 and 4,452,773, and U.S. published applications 20020064502 and 20020136693, all of which are hereby incorporated by reference in their entirety.

In certain examples, the molecule can be labelled to a cytotoxin or other cell proliferation inhibiting compound, in order to localize delivery of that agent to a tumor cell. For instance, the agent can be selected from the group consisting agents, enzyme inhibitors, proliferation inhibitors, lytic agents, DNA or RNA synthesis inhibitors, membrane permeability modifiers, DNA metabolites, dichloroethylsulfide derivatives, protein production inhibitors, ribosome inhibitors, inducers of apoptosis, and neurotoxins.

In one example, a molecule as described herein comprises one or more detectable markers to facilitate detection and/or isolation. For example, the polypeptide comprises a fluorescent label such as, for example, fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7, fluorescein (5-carboxyfluorescein-N-hydroxysuccinimide ester), rhodamine (5,6-tetramethyl rhodamine). The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm).

In certain examples, the molecule can be coupled with an agent useful in imaging tumours. Such agents include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many examples, such secondary functionality/moiety will be relatively large, e.g., at least 25 amu in size, and in many instances can be at least 50,100 or 250 amu in size. In certain examples, the secondary functionality is a chelate moiety for chelating a metal, e.g., a chelator for a radiometal or paramagnetic ion. In additional examples, it is a chelator for a radionuclide useful for radiotherapy or imaging procedures.

Alternatively, or in addition, the molecule may be labelled with, for example, a magnetic or paramagnetic compound, such as, iron, steel, nickel, cobalt, rare earth materials, neodymium-iron-boron, ferrous-chromium-cobalt, nickel-ferrous, cobalt-platinum, or strontium ferrite.

In another example, the molecule is conjugated to a "receptor" (such as streptavidin) for utilization in cell pretargeting wherein the conjugate is administered to the patient, followed by removal of unbound conjugate from the circulation using a clearing agent and then administration of a "ligand" (e.g., avidin) that is conjugated to a therapeutic agent (e.g., a radionucleotide).

Exemplary therapeutic agents include, but are not limited to an anti-angiogenic agent, an anti-neovascularization and/or other vascularization agent, an anti-proliferative agent, a pro-apoptotic agent, a chemotherapeutic agent, anti-mitotic agents (eg anti-mitotic agent Auristatin, (MMAF/MMAE as per Angew. Chem. Int. Ed. 2014, 53, 1-6) or a therapeutic nucleic acid.

Chemotherapeutics useful as agents herein include cytotoxic and cytostatic drugs. Chemotherapeutics may include those which have other effects on cells such as reversal of the transformed state to a differentiated state or those which inhibit cell replication. Examples of known cytotoxic agents useful in the present invention are listed, for example, in Goodman et al., "The Pharmacological Basis of Therapeutics," Sixth Edition, A. B. Gilman et al., eds./Macmillan Publishing Co. New York, 1980. These include taxanes, such as paclitaxel and docetaxel; nitrogen such as mechlorethamine, melphalan, uracil mustard and chlorambucil; ethylenimine derivatives, such as thiotepa; alkyl sulfonates, such as busulfan; nitrosoureas, such as lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, and mitomycin; enzymes, platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, acetate and megestrol acetate), estrogens (diethylstilbestrol and ethinyl estradiol), and androgens (testosterone propionate and fluoxymesterone).

In one example, multi-specific molecule as described herein is further conjugated or linked to another protein (e.g. Human Serum Albumin or HSA). In another example, the non-antibody protein is HSA.

The molecule may also be conjugated or linked to a therapeutic agent or a liposome (e.g. drug containing liposome).

Drugs that interfere with protein synthesis can also be used; such drugs are known to those skilled in the art and include puromycin, cycloheximide, and ribonuclease.

Additionally, other labels, such as biotin followed by streptavidin-alkaline phosphatase (AP), horseradish peroxidase are contemplated by the present disclosure.

The molecules of the present disclosure can be modified to contain additional nonproteinaceous moieties that are known in the art and readily available. For example, the moieties suitable for derivatization of the protein are physiologically acceptable polymer, e.g., a water soluble polymer. Non-limiting examples of water soluble polymers include, but are not limited to, polyethylene glycol (PEG), polyvinyl alcohol (PVA), or propropylene glycol (PPG).

Uses

In one example, the molecules of the present disclosure can be used for affinity purification or detection of desired antigens bearing an epitope to which the protein (or peptide) and/or BDM binds.

The present disclosure also provides a method for detecting a target to which either or both of the protein and BDM moieties of the polypeptide bind. Such methods may for example, employ the use of detectable labels as described above. In one example, different labels could be utilised for the protein and the BDM to identify whether the target bound is that bound by the protein or the BDM.

A variety of formats can be employed to determine whether a sample contains a target (e.g. protein) that binds to the protein or peptide and/or BDM. Examples of such formats include, but are not limited to, enzyme immunoassay (EIA), radioimmunoassay (RIA), Western blot analysis and enzyme linked immunoabsorbant assay (ELISA).

In one format, the polypeptide can be used in methods such as Western blots or immunofluorescence techniques to detect a target.

The polypeptide or target antigen to which the protein (or peptide) or BDM binds may be immobilised on a solid support. Alternatively, the multi-specific molecule may be bound to a solid support. Suitable solid phase supports or carriers include any support capable of binding an antigen (i.e. target) or an immunoglobulin or BDM. Well-known supports or carriers include glass, polystyrene, polypropylene, polyethylene, dextran, nylon, amylases, natural and modified celluloses, polyacrylamides, gabbros, and magnetite. One skilled in the art will know many other suitable carriers for binding the protein, BDM or target antigen, and will be able to adapt such support for use with the present disclosure. For example, target protein can be run on a polyacrylamide gel electrophoresis and immobilized onto a solid phase support such as nitrocellulose. The support can then be washed with suitable buffers followed by treatment with the detectably labelled polypeptide. The solid phase support can then be washed with the buffer a second time to remove unbound polypeptide. The amount of bound label on the solid support can then be detected by conventional means.

In one example, the molecules of the present disclosure can be used as medicaments.

Advantages of the Multi-Specific Molecules of the Disclosure

With regard to non-antibody proteins, the addition of the BDM to such proteins can assist in increasing the proteins stability, circulation time and/or biological activity. For example, a factor VIII protein can be coupled to a VLD that binds to human serum albumin so that the half-life of the protein is increased. This has obvious advantages in terms of less frequent dosing for subjects with haemophilia.

With regard to antibodies, the molecules according to the present disclosure provide advantages over therapeutics based on bi-specific antibodies. A simple and efficient approach for improving one or more characteristics of an antibody, e.g. poorly therapeutic antibody is to attach one or more single binding domain molecules (BDM) that bind to specific therapeutic targets to an antibody or an immunoglobulin antigen-binding fragment which has specificity to a target of interest.

The advantages with this bi-specific approach are: simple and highly efficient bi-specific antibody generation; the approach is applicable to any antibody sequence; the parent antibody retains its original binding sites and specificity; the parent antibody retains its avidity; the parent antibody retains its original structure and function and antibody-mediated effector functions are retained for select applications; antibody pharmacokinetics including serum half-life are retained; the bi-specific product integrates seamlessly into existing IgG production processes such as manufacturing, purification, formulation and all other processes based on standard IgG processes.

In select applications, bi-specifics based on antibody Fab fragments will also be desirable due to their smaller molecular weight, shorter half-life in the blood stream and an improved molecular weight to binding site ratio relative to whole antibodies.

As one example, the neutralisation of toxic substances which have been traditionally treated with whole antibodies can be more effectively treated with Fabs. Due to the relatively large molecular weight of an antibody (150 kDa) as compared to the toxic substance (typically less than 1 kDa), a large quantity of antibody is required to bind stoichiometrically to the toxin. Bi-specific or tri-specific Fabs described herein can be used at lower dose due to the multiple binding sites offered by the bi-specific or tri-specific. The small size of Fabs relative to antibodies sees the toxic substance-Fab complexes quickly excreted via the kidneys. Again, an efficient and simple approach for generating Fab-based bi-specifics is to attach BDM's that bind to specific targets to an existing Fab which has specificity to a target of interest.

Kits

The present disclosure also provides a kit comprising a multi-specific molecule described herein, together with instructions for use. Where the compositions are lyophilized, the kit can contain further preparations of solutions to reconstitute the preparations. The instructions may be on 'printed matter', e.g., on paper or cardboard within or affixed to the kit, or on a label affixed to the kit or packaging material, or attached to a vial or tube containing a component of the kit.

Additionally, the kits can further include any of the other moieties provided herein such as, for example, a chemotherapeutic agent.

The kits can further include the components for an assay provided herein, for example an ELISA assay.

The kit may further include a label specifying, for example a product description, mode of administration and indication of treatment. The label or packaging insert can include appropriate written instructions.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

Example 1 Generation of Antibody Bi-Specific and Tri-Specific Molecules i) Vector Generation Gene construction and cloning of CTLA-4 BDMs was by standard and well-described techniques and further as previously described in U.S. Pat. No. 7,166,697. The CTLA-4 BDM were obtained from a library (Geneart). The gene library 1696327 was assembled using synthetic degenerated oligonucleotides with the objective of containing different substitutions in the DNA sequence corresponding to the binding loop regions.

The CTLA-4 sequence used in these examples comprise a C-terminal modification of the native sequence wherein the native sequence PEPCPDSDGSTG (SEQ ID NO: 43) is replaced with PEPSPDSN (SEQ ID NO: 44). These sequence does not contain the C-terminus Cys residue which allows the BDM to remain in monomeric form.

Nucleic acid constructs encoding anti-lysozyme IgG1 heavy chain sequence fused to the B7-1 binding CTLA-4 V-like domain sequence (designated D1.3 IgG-VLDx2 (HC)) and anti-lysozyme IgG kappa light chain sequence fused to B7-1 binding V-like domain sequence (designated D1.3 IgG-VLDx2 (LC)) were produced. The VLD was coupled to the antibody heavy (H) or light (L) chain respectively through a Gly-Ser linker sequence. All DNA constructs were verified by restriction analysis and DNA sequencing and tested for expression of recombinant protein by standard and well-understood techniques.

The sequences of these constructs are shown below. The antigen-binding loops are underlined where relevant:

Sequence of the B7-1 binding V-like domain (VLD)
(SEQ ID NO: 13)

KAMHVAQPAVVLASSRGIASFVCEYASPGKYTEVRVTVLRQADSQVTEVCAATYMTGNELTFL

DDSICTGTSSGNOVNLTIQGLRAMDTGLYICKVELMYPPPYYLGIGNGTQIYVIDPEPSPDSN

The binding loops of the VLD are underlined.

Linker sequence (SEQ ID NO: 16)

SGGGGSGGGGSGGGGS

Linker sequence (SEQ ID NO: 17)

SGGGGSGGGGSGGGGSGGGGS

Anti-Lysozyme IgG1 heavy chain sequence used in antibody-VLD fusions (SEQ ID NO: 18)

EVKLQESGPGLVAPSQSLSITCTVSGFSLTGYGVNWVRQPPGKGLEWLGMIWGDGNTDYNS

ALKSRLSISKDNSKSQVFLKMNSLHTDDTARYYCARERDYRLDYWGQGTTVTVSSASTKGPS

VFPLAPSSKSTSGGTAALGCLVKDYFPEPVTVSWNSGALTSGVHTFPAVLOSSGLYSLSSVVT

VPSSSLGTQTYICNVNHKPSNTKVDKKVEPPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHEALHNH

YTQKSLSLSPGK

Sequence of the Anti-Lysozyme IgG1 heavy chain coupled to B7-1 binding VLD by a linker (D1.3 IgG-VLDx2 (HC))

(SEQ ID NO: 19)

EVKLQESGPGLVAPSQSLSITCTVSGFSLTGYGVNWVRQPPGKGLEWLGMIWGDGNTDYNS

ALKSRLSISKDNSKSQVFLKMNSLHTDDTARYYCARERDYRLDYWGQGTTVTVSSASTKGPS

VFPLAPSSKSTSGGTAALGCLVKDYFPEPVTVSWNSGALTSGVHTFPAVLQSSGLYSLSSVVT

VPSSSLGTQTYICNVNHKPSNTKVDKKVEPPKSCDKTHTCPPCPAPELLGGPSVFLFPPKPKD

TLMISRTPEVTCVVVDVSHEDPEVKFNWYVDGVEVHNAKTKPREEQYNSTYRVVSVLTVLHQ

DWLNGKEYKCKVSNKALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVFSCSVMHEALHNH

YTQKSLSLSPGKSGGGGSGGGGSGGGGSKAMHVAQPAVVLASSRGIASFVCEYASPGKYTE

VRVTVLRQADSQVTEVCAATYMTGNELTFLDDSICTGTSSGNQVNLTIQGLRAMDTGLYICKV

ELMYPPPYYLGIGNGTQIYVIDPEPSPDSN

The binding loops of the VLD are underlined.

Anti-Lysozyme IgG kappa light chain (SEQ ID NO: 20)

DIELTQSPASLSASVGETVTITCRASGNIHNYLAWYQQKQGKSPQLLVYYTTTLADGVPSRFSG

SGSGTQYSLKINSLOPEDFGSYYCQHFWSTPRTFGGGTKLELKRTVAAPSVFIFPPSDEQLKS

GTASVVCLLNNFYPREAKVQWKVDNALQSGNSQESVTEQDSKDSTYSLSSTLTLSKADYEKH

KVYACEVTHQGLSSPVTKSFNRGEC

Anti-Lysozyme IgG kappa light chain coupled to B7-1 binding VLD with a 21 aa Gly-Ser linker (designated D1.3 IgG-VLDx2 (LC))

(SEQ ID NO: 21)

DIELTQSPASLSASVGETVTITCRASGNIHNYLAWYQQKQGKSPQLLVYYTTTLADGVPSRFSG

SGSGTQYSLKINSLQPEDFGSYYCQHFWSTPRTFGGGTKLELKRTVAAPSVFIFPPSDEQLKS

GTASVVCLLNNFYPREAKVQWKVDNALQSGNSQESVTEQDSKDSTYSLSSTLTLSKADYEKH

KVYACEVTHQGLSSPVTKSFNRGECSGGGGSGGGGSGGGGSGGGGSKAMHVAQPAVVLA

-continued

```
SSRGIASFVCEYASPGKYTEVRVTVLRQADSQVTEVCAATYMTGNELTFLDDSICTGTSSGNQ

VNLTIQGLRAMDTGLYICKVELMYPPPYYLGIGNGTQIYVIDPEPSPDSN
The binding loops of the VLD are underlined.

Anti-lysozyme Fab kappa light chain coupled to B7.1 binding VLD with a 21 aa
Gly-Ser linker (designated D1.3 Fab-VLDx1 (LC)
                                                                    (SEQ ID NO: 22)
DIELTQSPASLSASVGETVTITCRASGNIHNYLAWYQQKQGKSPQLLVYYTTTLADGVPSRFSG

SGSGTQYSLKINSLOPEDFGSYYCQHFWSTPRTFGGGTKLELKRTVAAPSVF1FPPSDEQLKS

GTASVVQLLNNFYPREAKVQWKVDNALQSGNSQESVTEQDSKDSTYSLSSTLTLSKADYEKH

KVYACEVTHQGLSSPVTKSFNRGECSGGGGSGGGGSGGGGSGGGGSKAMHVAQPAVVLA

SSRGIASFVCEYASPGKYTEVRVTVLRQADSQVTEVCAATYMTGNELTFLDDSICTGTSSGNQ

VNLTIQGLRAMDTGLYICKVELMYPPPYYLGIGNGTQIYVIDPEPSPDSN
The binding loops of the VLD are underlined.

Anti-lysozyme Fab heavy chain coupled to B7.1 binding VLD with 21 aa Gly-Ser
linker (designated D1.3 Fab-VLDx1 (HC)
                                                                    (SEQ ID NO: 23)
EVKLQESGPGLVAPSQSLSITCTVSGFSLTGYGVNWVRQPPGKGLEWLGMIWGDGNTDYNS

ALKSRLSISKDNSKSQVFLKMNSLHTDDTARYYCARERDYRLDYWGQGTTVTVSSASTKGPS

VFPLAPSSKSTSGGTAALGCLVKDYFPEPVTVSWNSGALTSGVHTFPAVLQSSGLYSLSSVVT

VPSSSLGTQTYICNVNHKPSNTKVDKKVEPKSCSGGGGSGGGGSGGGGSGGGGSKAMHVA

QPAVVLASSRGIASFVCEYASPGKYTEVRVTVLRQADSQVTEVCAATYMTGNELTFLDDSICT

GTSSGNQVNLTIQGLRAMDTGLYICKVELMYPPPYYLGIGNGTQIYVIDPEPSPDSN
The binding loops of the VLD are underlined.

Anti-lysozyme Fab Heavy chain (with C-terminal His6
(SEQ ID NO: 31) and myc tags)
                                                                    (SEQ ID NO: 24)
EVKLQESGPGLVAPSQSLSITCTVSGFSLTGYGVNWVRQPPGKGLEWLGMIWGDGNTDYNS

ALKSRLSISKDNSKSQVFLKMNSLHTDDTARYYCARERDYRLDYWGQGTTVTVSSASTKGPS

VFPLAPSSKSTSGGTAALGCLVKDYFPEPVTVSWNSGALTSGVHTFPAVLQSSGLYSLSSVVT

VPSSSLGTQTYICNVNHKPSNTKVDKRVEPKSCAAAGLGGHHHHHHGAAEQKLISEEDL
``` ii) Production of Bi-Specific and Tri-Specific Molecules

Individual heavy and light chains encoding the antibody-VLD or Fab-VLD sequences were cloned into expression vector pcDNA3.4 (Thermo Fisher). The vectors were produced/amplified in *E. coli* cells (Electro Ten Blue from Agilent Technologies).

Figure 2:
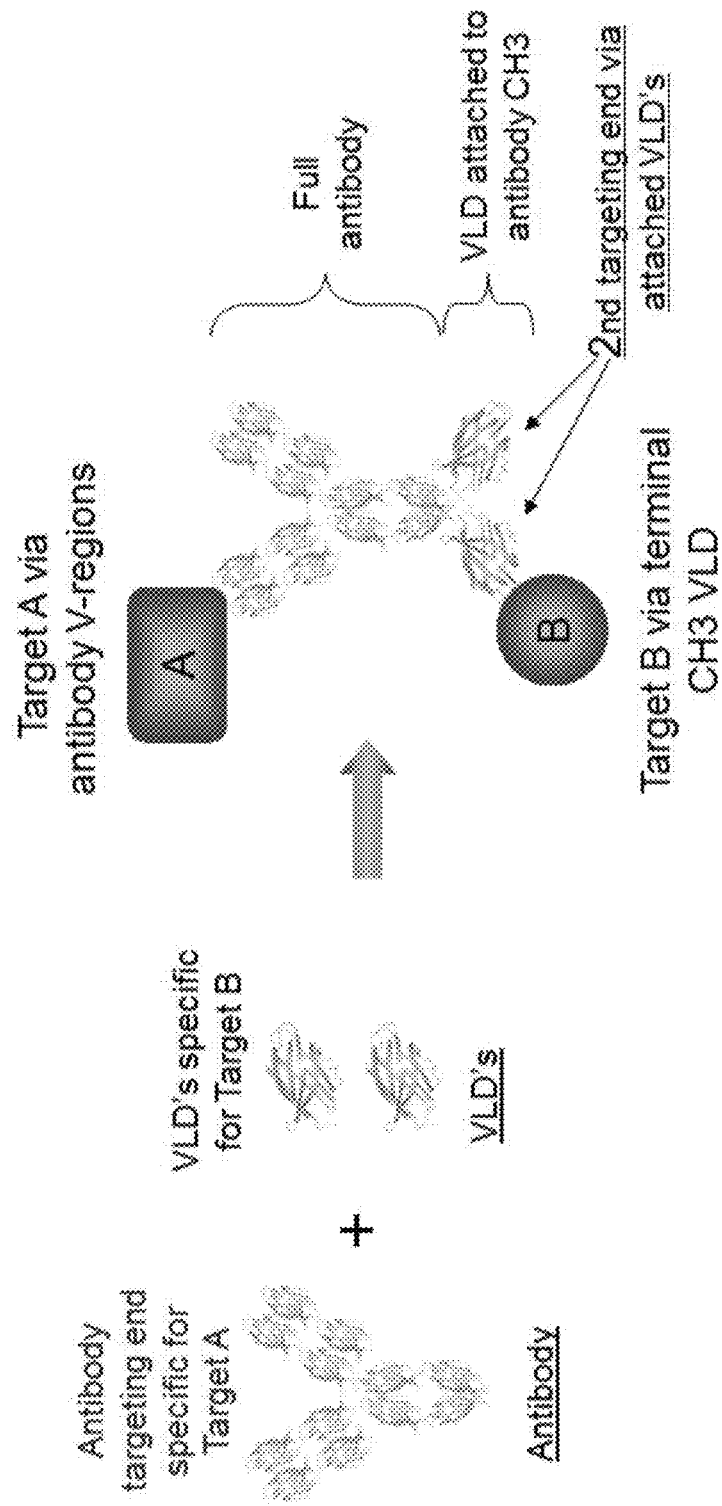
FIG. 2 shows a schematic of an antibody-VLD bi-specific molecule according to one example of the disclosure. The antibody binds to target A via its heavy and light chain V domains. The VLDs which are attached to the C-terminus CH3 constant domain of the antibody heavy chain bind to Target B. The bi-specific can bind to both Target A and B either individually or at the same time.
Figure 3:
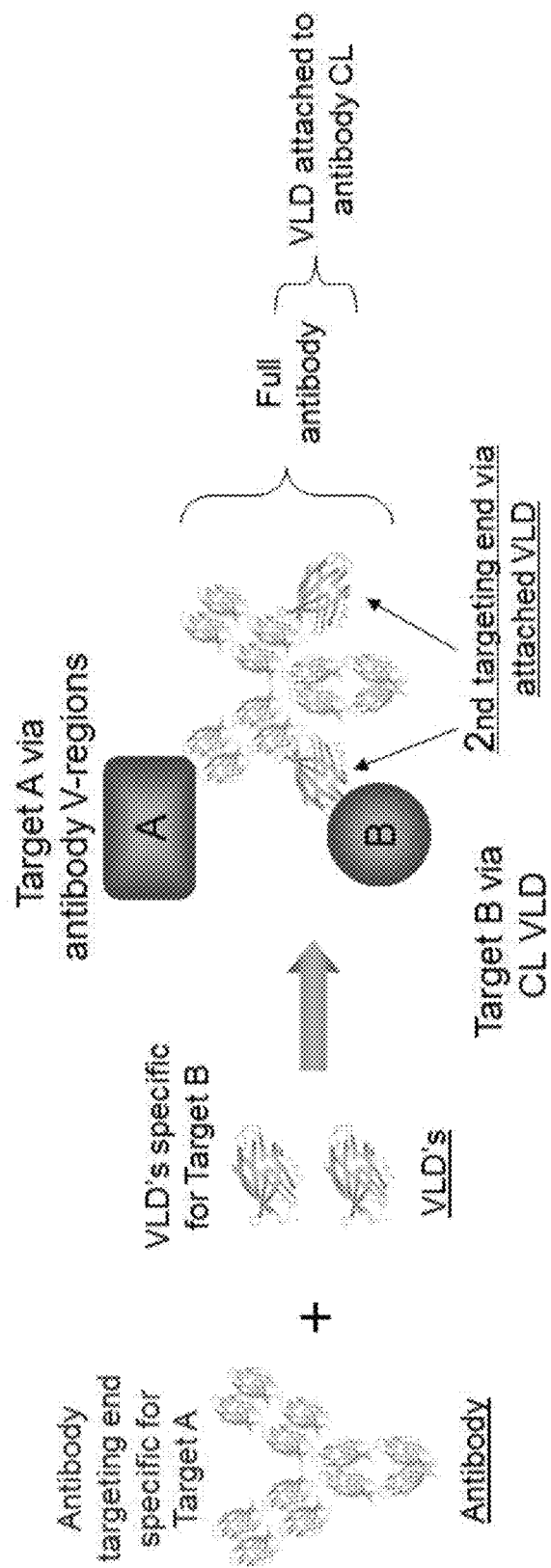
FIG. 3 shows a schematic of an antibody-VLD bi-specific molecule according to one example of the disclosure. The antibody binds to Target A via its heavy and light chain V domains. A VLD is attached at the C-terminus of each constant domain of the light chain (constant light, CL) and binds to Target B. The bi-specific can bind to both Target A and B either individually or at the same time.
Figure 4:
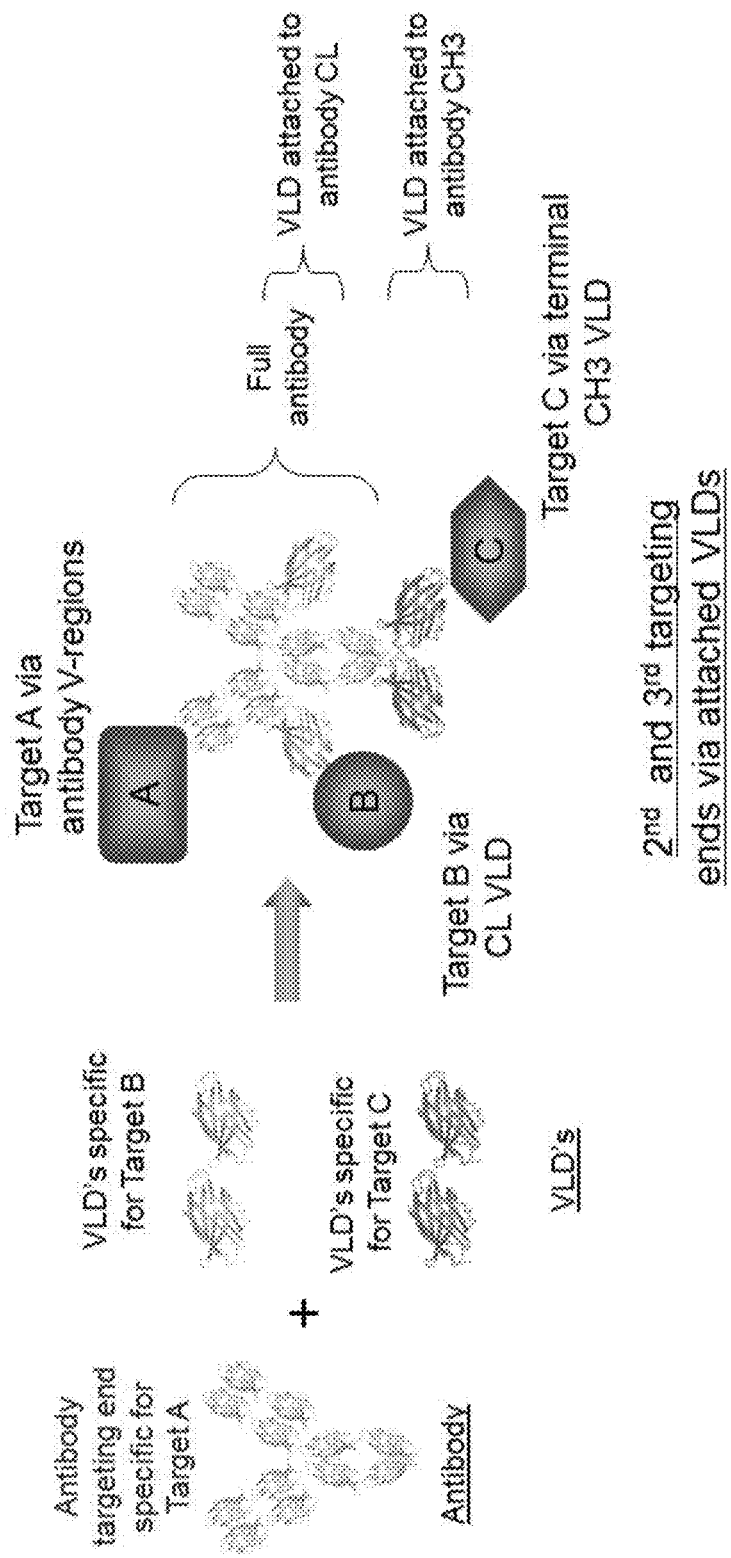
FIG. 4 shows a schematic of an antibody-VLD tri-specific molecule according to one example of the disclosure. The antibody binds to Target A via its heavy and light chain V domains. A VLD is attached to the C-terminus of each light chain constant domain (CL) and heavy chain constant domain (CH3). The tri-specific can bind to Target A and B and C either individually or at the same time or in a combination of the three targets (e.g. Target A and B or Target A and C or Target B and C).
Figure 5:
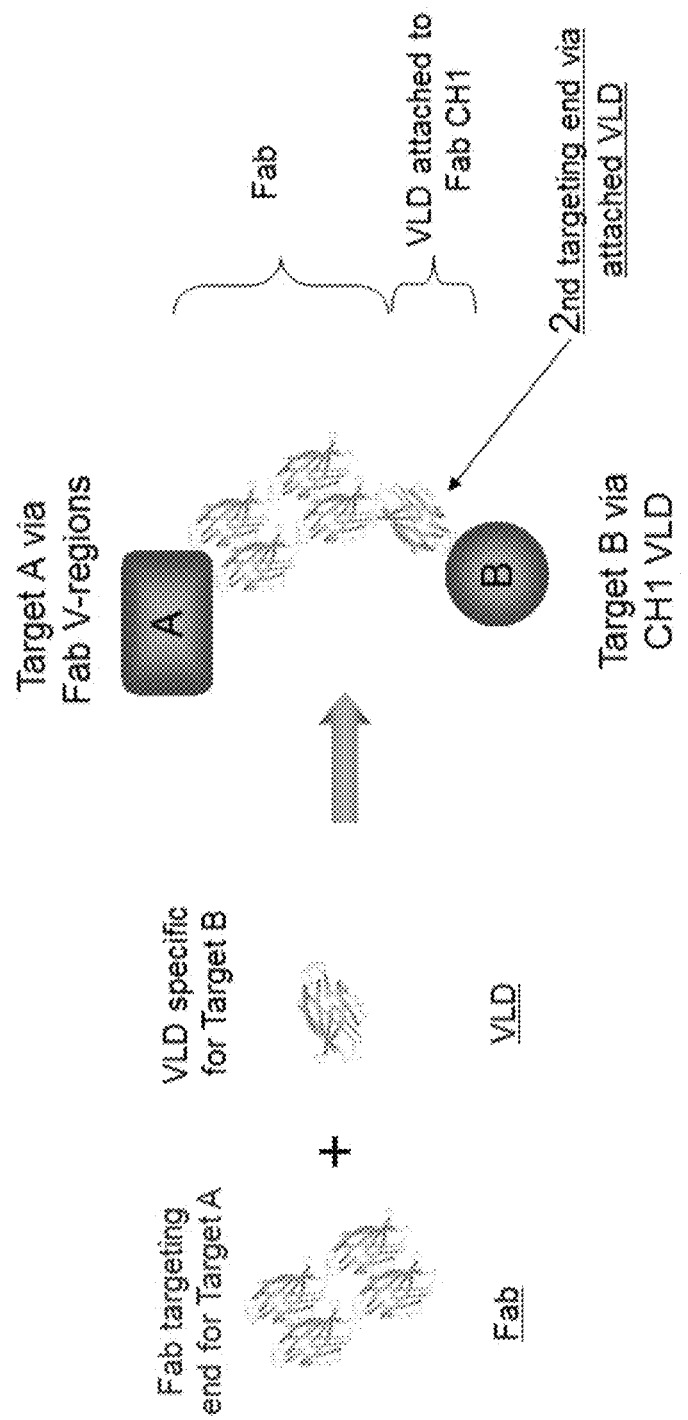
FIG. 5 shows a schematic of an Fab-VLD bi-specific molecule according to one example of the disclosure. The Fab binds to Target A via its heavy and light chain V domains. A VLD is attached to the C-terminus of the heavy chain constant domain (CH1) and binds to Target B. The bi-specific can bind to both Target A and B either individually or at the same time.
Figure 6:
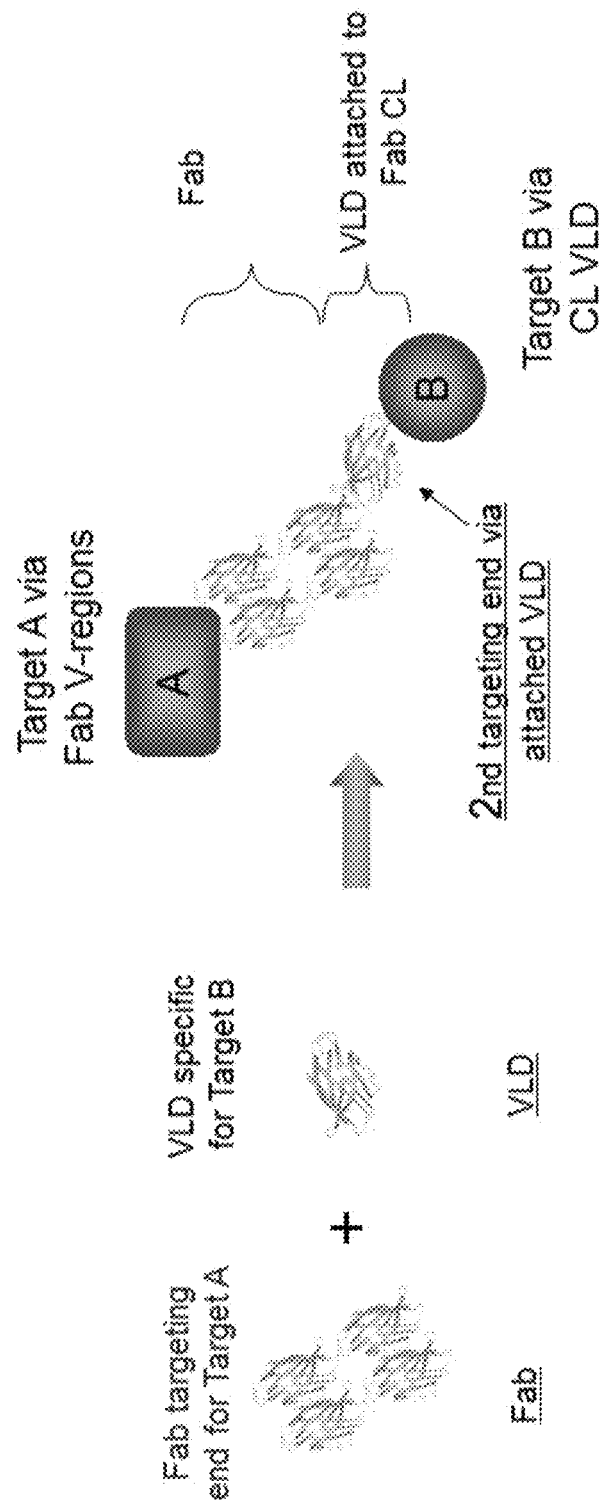
FIG. 6 shows a schematic of the Fab-VLD bi-specific molecule according to one example of the disclosure. The Fab binds to Target A via its heavy and light chain V domains. A VLD is attached to the C-terminus of the light chain constant domain (CL) and binds to Target B. The bi-specific can bind to both Target A and B either individually or at the same time.
Figure 7:
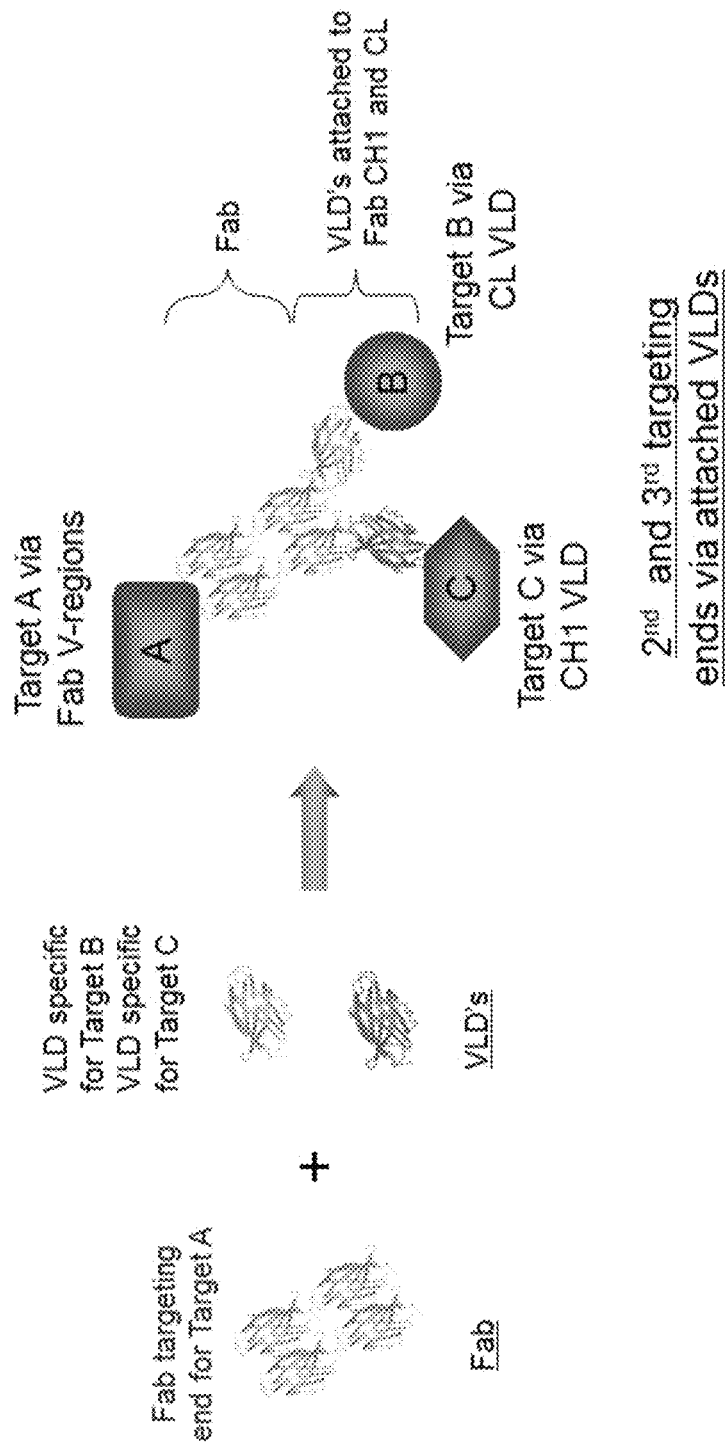
FIG. 7 shows a schematic of the Fab-VLD tri-specific molecule according to one example of the disclosure. The Fab binds to Target A via its heavy and light chain V domains. A VLD is attached to the C-terminus of the light chain constant domain (CL) and binds to Target B and a VLD is attached to the C-terminus of the heavy chain constant domain (CH1) and binds to Target C. The tri-specific can bind to Target A and B and C either individually or at the same time or in a combination of the three targets (e.g. Target A and B or Target A and C or Target B and C).

Schematics of the bi-specific and tri-specific molecules according to the present disclosure is shown by way of illustration in FIGS. 2-4 for antibody-VLD molecules and in FIGS. 5-7 for Fab-VLD molecules.

FIG. 2 shows a schematic of the antibody-VLD bi-specific molecule according to one example created by coupling of a target specific VLD (e.g. that bind to Target B) to the terminal end of each constant heavy (CH3) chain sequence of the anti-Lysozyme IgG1 antibody heavy chain [D1.3 IgG-VLDx2 (HC)]. The antibody molecule binds to target A via the antibody heavy and light chain variable regions and to target B via the VLD on the heavy chain.

FIG. 3 shows a schematic of the antibody-VLD bi-specific molecule according to one example created by coupling a target specific VLD (e.g. that bind to Target B) to the terminal end of each constant light (CL) chain sequence of the anti-Lysozyme IgG1 antibody light chain [D1.3 IgG-VLDx2 (LC)]. The molecule binds to target A via the antibody heavy and light chain variable regions and to target B via the VLD on the light chain.

FIG. 4 shows a schematic of the antibody-VLD tri-specific molecule according to one example created by coupling of a target specific VLD (e.g. that bind to Target B) to both the heavy and light chains D1.3 IgG-VLDx4 (LC+HC) where a VLD is coupled to the terminal CL sequence and also to the terminal end of the heavy CH3 sequence. The molecule binds to target A via the antibody heavy and light chain variable regions, to target B via the VLD on the light chain and to target C via the same VLD or a different VLD to that which binds target B. The tri-specific can bind to Target A, B and C either individually or at the same time or in a combination of the three targets (e.g. Target and B or Target A and C or Target B and C).

FIG. 5 shows a schematic of the bi-specific Fab-VLD molecule (D1.3 Fab-VLDx1 (HC)) according to one example the disclosure. In this schematic, the bi-specific is created by a fusion of a target specific VLD (e.g. in this example the VLD is specific for Target B) to the terminal end of the constant region (CH1) sequence of a Fab that binds to Target A (e.g. in this example the Fab is specific for Target A). The bi-specific can bind to both Target A and B either individually or at the same time.

FIG. 6 shows a schematic of the bi-specific Fab-VLD molecule (D1.3 Fab-VLDx1 (LC)) according to one example of the disclosure. In this schematic, the bi-specific is created by a fusion of a target specific VLD (e.g. in this example the VLD is specific for Target B) to the terminal end of the CL sequence of a Fab that binds to Target A (e.g. in this example the Fab is specific for Target A). The bi-specific can bind to both Target A and B either individually or at the same time.

FIG. 7 shows a schematic of the tri-specific Fab-VLD molecule (D1.3 Fab-VLDx2 (LC+HC)) according to the disclosure. In this schematic, the tri-specific is created by a fusion of a target specific VLD (e.g. in this example the VLD is specific for Target B) to the terminal end of the Fab CL sequence and a fusion of a second target specific VLD (e.g. in this example the VLD is specific for Target C) to the terminal end of the Fab CH3 sequence that binds to Target A (e.g. in this example the Fab is specific for Target A). The tri-specific can bind to Target A and B and C either individually or at the same time or in a combination of the three targets (e.g. Target A and B or Target A and C or Target B and C).

Vector transformation of bacteria was performed according to standard techniques using 2 ng of DNA using the electroporation competent cell line (e.g. ElectroTen-Blue cells, Stratagene Cat #200159).

Following vector amplification, DNA was extracted and prepared using Qiagen HiSpeed Plasmid Maxi Kit (Cat #12663) or Qiafilter Plasmid Mega Kit (Cat #12281). DNA was eluted in nuclease free purified water.

iii) Transfection of DNA into Mammalian Cells for Protein Expression

Transfection of ~2×10⁶ Expi293 cells/mL mammalian cells at >95% viability was performed using the Expi293 Expression System (ThermoFisher Scientific). The bi-specific or tri-specific DNA vectors were prepared at a 1:3 ratio of HC:LC DNA. DNA was heated to 65° C. for 5 min and allowed to come down to room temperature before adding Opti-MEM I (Life Technologies Cat #31985070) and Expi-Fectamine 293 reagent (ThermoFisher Cat #A14525) and incubated at room temperature for 30 mins. The transfection complex was added to cells and incubated at 37° C., 5% $CO_2$ at 120 rpm. Protein containing supernatant was harvested after approximately 4-5 days.

The protein expression levels of the antibody-VLD and Fab-VLD parent anti-lysozyme D1.3 antibody, the bi-specific and tri-specific variants obtained from transfection using the Expi293 expression system were determined are shown in Tables 1 and 2 respectively. The antibody or Fab binds to lysozyme and the VLD binds to B7.1.

TABLE 1

Protein expression levels in the bi-specific and tri-specific antibody-VLD variants

| Sample | Ab-VLD Fusion | Total purified Yield (mg) |
| --- | --- | --- |
| D1.3 IgG alone (full length) | None | 0.45 |
| D1.3 IgG-VLDx2 (HC) | Heavy chain | 0.36 |
| D1.3 IgG-VDLx2 (LC) | Light chain | 0.71 |
| D1.3 IgG-VLDx4 (HC + LC) | Heavy and light chains | 0.29 |

TABLE 2

Protein expression levels in the bi-specific and tri-specific Fab-VLD variants

| Sample | Fab-VLD Fusion | Total purified Yield (mg) |
| --- | --- | --- |
| D1.3 Fab alone | None | 0.41 |
| D1.3 Fab-VLDx1 (HC) | CH1 | 0.31 |
| D1.3 Fab-VLDx1 (LC) | Light chain | 0.40 |
| D1.3 Fab-VLDx2 (HC + LC) | Heavy and light chains | 0.14 | iv) Purification

ProsepA purification was used for purification of the bi-specific and tri-specific molecules. The ProsepA column was equilibrated with 5 column volumes of PBS/Tris (2 mM Tris, pH 8). Transfected cell supernatant containing the bi-specific molecule at pH 8 was loaded onto the column and the column washed with 10 column volumes of PBS, 2 mM Tris, pH 8. The protein was eluted with 0.1 M Glycine pH 3. The eluted protein fraction was neutralized to ~pH 7 with 1 M Tris, pH 8. and dialysed according to standard methods.

Protein expression levels of the variants were determined by SDS PAGE. Values were obtained from 30 ml expression cultures which were purified via affinity chromatography (not shown).

Example 2 Expression of Fab Molecules

Figure 8:
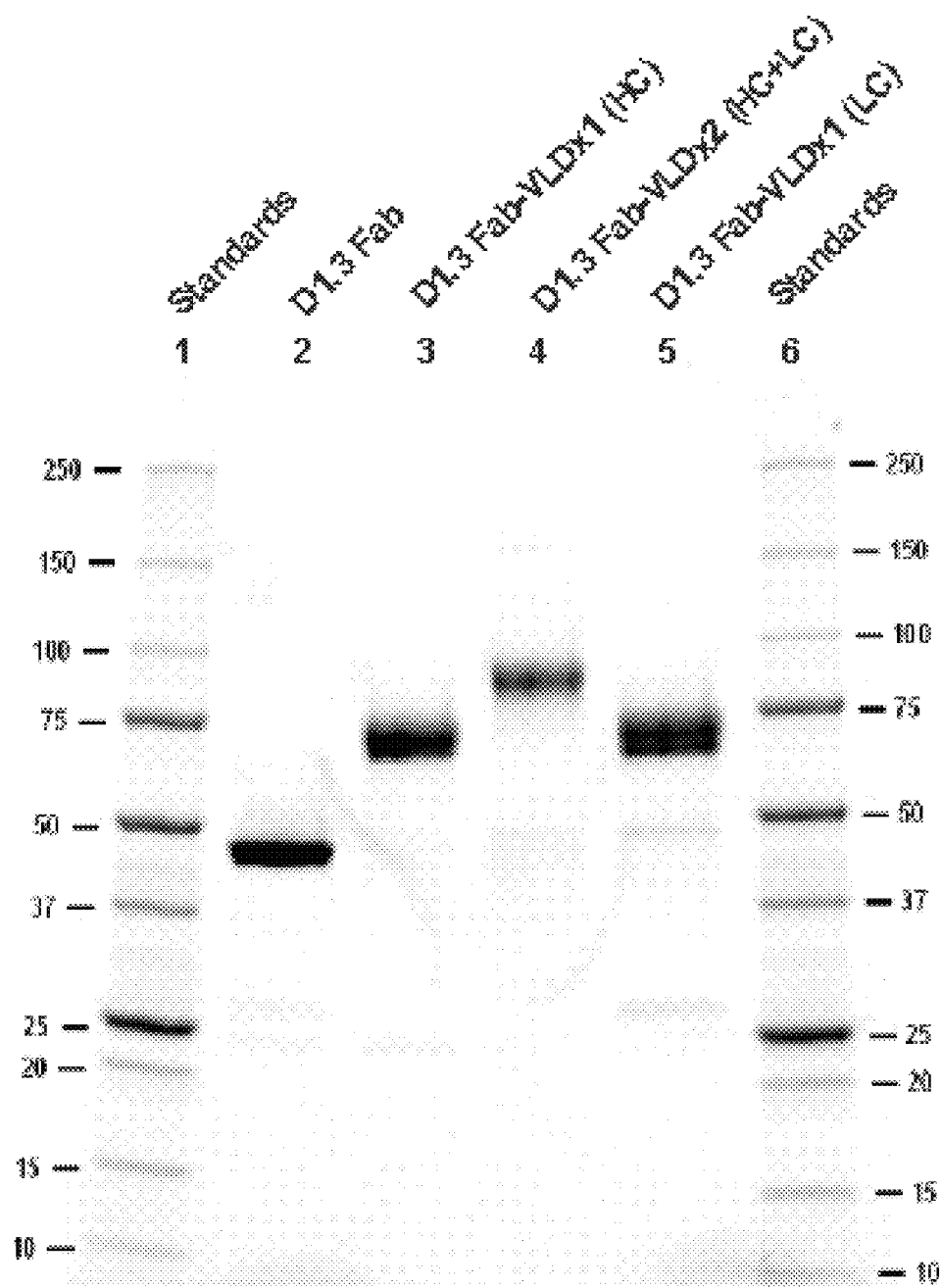
FIG. 8 shows the expression (SDS PAGE) under non-reducing conditions of the parent D1.3 Fab, and the bi-specific and tri-specific variants. D1.3 Fab is the anti-lysozyme Fab; D1.3 Fab-VLDx1 (HC) is the anti-lysozyme Fab with a VLD fused to the CH1 domain of the heavy chain; D1.3 Fab-VLDx1 (LC) is the anti-lysozyme Fab with a VLD fused to the CL domain of the light chain; D1.3 Fab-VLDx2 (HC+LC) is the anti-lysozyme Fab with VLDs fused to the CH1 domain of the heavy chain and to the CL domain of the light chain.
Figure 9:
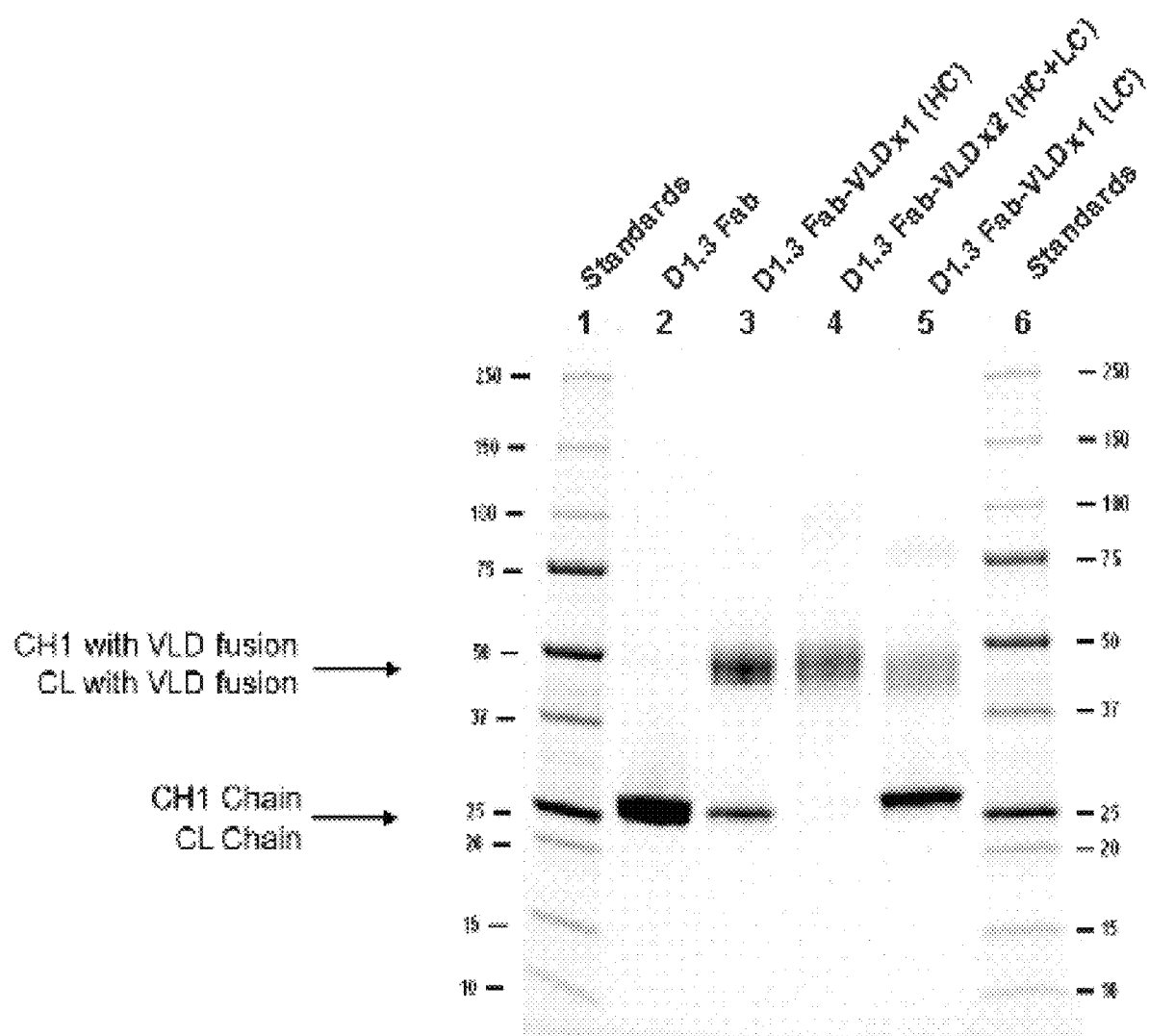
FIG. 9 shows SDS PAGE expression analysis under reducing conditions of the parent D1.3 Fab, the bi-specific and tri-specific variants. D1.3 Fab is the anti-lysozyme Fab; D1.3 Fab-VLDx1 (HC) is the anti-lysozyme Fab with a VLD fused to the CH1 domain of the heavy chain; D1.3 VLDx1 (LC) is the anti-lysozyme Fab with a VLD fused to the CL domain of the light chain; D1.3 VLDx2 (HC+LC) is the anti-lysozyme Fab with VLDs fused to the CH1 domain of the heavy chain and to the CL domain of the light chain.

Expression of parent D1.3 Fab, and its bi-specifics and tri-specific variants which were expressed in a non-optimised standard Expi293 expression system were analysed by SDS PAGE under non-reducing and reducing conditions. Values were obtained from 30 ml expression cultures which were purified via affinity chromatography. The parent Fab is D1.3 Fab, the bi-specific are D1.3 Fab-VLDx1 (HC) which is the D1.3 Fab plus a VLD fused to the terminal end of the CH sequence of the D1.3 Fab, and D1.3 Fab-VLDx1 (CL) which is the D1.3 Fab plus a VLD fused to the terminal end of the CL sequence of the D1.3 Fab. The tri-specific is D1.3 Fab-VLDx2 (HC+LC) which is the D1.3 Fab plus VLDs fused to both the terminal end of the CH sequence and CL sequence of the D1.3 Fab. Results are shown in FIG. 8 under non-reducing conditions. Results are known in FIG. 9 under reducing conditions. Analysis indicated that appropriate heavy and light chain fusions were at the size ranges expected.

Example 3 Assessment of Binding of Bi-Specific and Tri-Specific Molecules

The binding properties of the purified bi-specific and tri-specific molecules were characterised using the ForteBio Blitz biosensor using standard chemistry and reagents.

Affinity chromatography purified antibodies, antibody-VLD bi-specific and antibody-VLD tri-specific molecules were used with commercially available Lysozyme (Sigma Aldrich cat #L4919) and B7-1-Fc (R&D Systems Cat #140-B1). A streptavidin capturing surface (SA Sensor ForteBio cat #18-5019, or Sensor Chip SA, GE Cat #BR-1000-32) was used to capture biotin labelled lysozyme. The antibody, antibody-VLD bi-specific and antibody-VLD tri-specific molecules were passed over the target captured on the biosensor surface to generate a binding sensorgram (i.e. first specificity). Over the same target, during the dissociation phase, B7-1-Fc was passed over the already bound antibody, antibody-VLD bi-specific and antibody-VLD tri-specific molecules (i.e. the second specificity) to demonstrate the second binding interaction.

Figure 10:
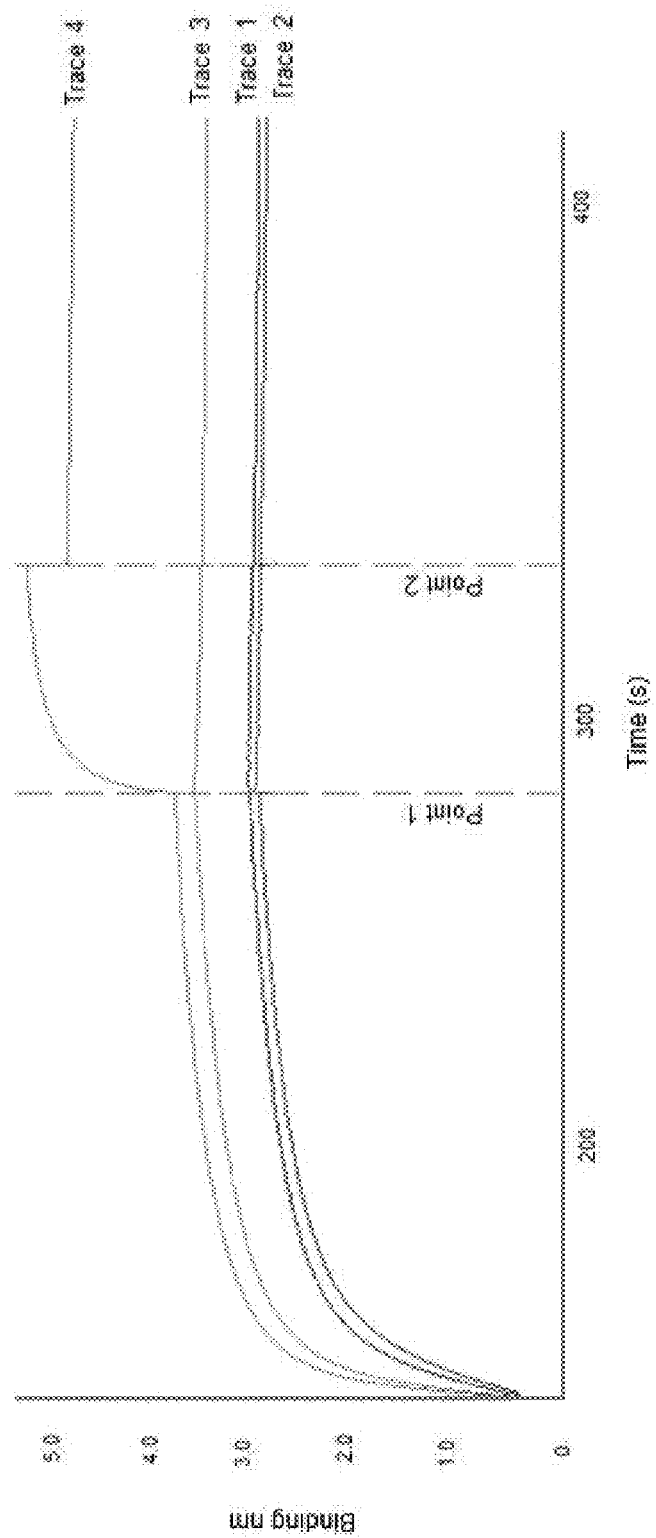
FIG. 10 shows BLitz® analysis of initial binding of the bi-specific [IgG VLDx2 (HC)] to streptavidin captured biotin labelled lysozyme followed by secondary binding to B7.1-Fc. The bi-specific has B7-1 binding VLDs fused to the D1.3 antibody [D1.3 IgG] heavy chains. Trace 1 is the D1.3 anti-lysozyme antibody binding to lysozyme immobilised on the biosensor surface followed by an addition of Buffer at Point 1. Trace 2 is the D1.3 anti-lysozyme antibody binding to lysozyme followed by an addition of B7-1-Fc at Point 1. B7-1-Fc was replaced with Buffer at Point 2. Trace 3 is the bi-specific—D1.3 IgG-VLDx2 (HC) binding to lysozyme immobilised on the biosensor surface followed with an addition of buffer at Point 1. Trace 4 is the bi-specific—D1.3 IgG-VLDx2 (HC) binding to lysozyme immobilised on the biosensor surface followed by an addition of B7-1-Fc at Point 1. B7-1-Fc was replaced with Buffer at Point 2. The sensorgram demonstrates simultaneous, dual target binding to lysozyme and B7-1-Fc.

FIG. 10 shows preliminary analysis using the ForteBio Blitz biosensor to demonstrate binding of the bi-specific [IgG VLDx2 (HC)] to streptavidin captured biotin labelled lysozyme followed by secondary binding to B7.1-Fc. The bi-specific has B7-1 binding VLDs coupled to the D1.3 antibody [D1.3 IgG] heavy chains. Trace 1 is a sensorgram of the D1.3 anti-lysozyme antibody [D1.3 IgG] used to construct the bi-specific. The antibody is shown binding to lysozyme immobilised on the biosensor surface followed by an addition of Buffer at Point 1. Trace 2 is a sensorgram of the D1.3 anti-lysozyme antibody [D1.3 IgG] used to construct the bi-specific. The antibody is shown binding to lysozyme immobilised on the biosensor surface followed by an addition of B7-1-Fc at Point 1. B7-1-Fc was replaced with Buffer at Point 2. Trace 3 is a sensorgram of the bi-specific D1.3 anti-lysozyme antibody with VLDs coupled to the antibody constant heavy (CH) chains [the bi-specific—D1.3 IgG-VLDx2 (HC)]. The bi-specific is shown binding to lysozyme immobilised on the biosensor surface followed with an addition of buffer at Point 1. Trace 4 is a sensorgram of the bi-specific D1.3 anti-lysozyme antibody with VLDs coupled to the antibody CH chains [the bi-specific—D1.3 IgG-VLDx2 (HC)]. The bi-specific is shown binding to lysozyme immobilised on the biosensor surface followed by an addition of B7-1-Fc at Point 1. B7-1-Fc was replaced with Buffer at Point 2.

Figure 11:
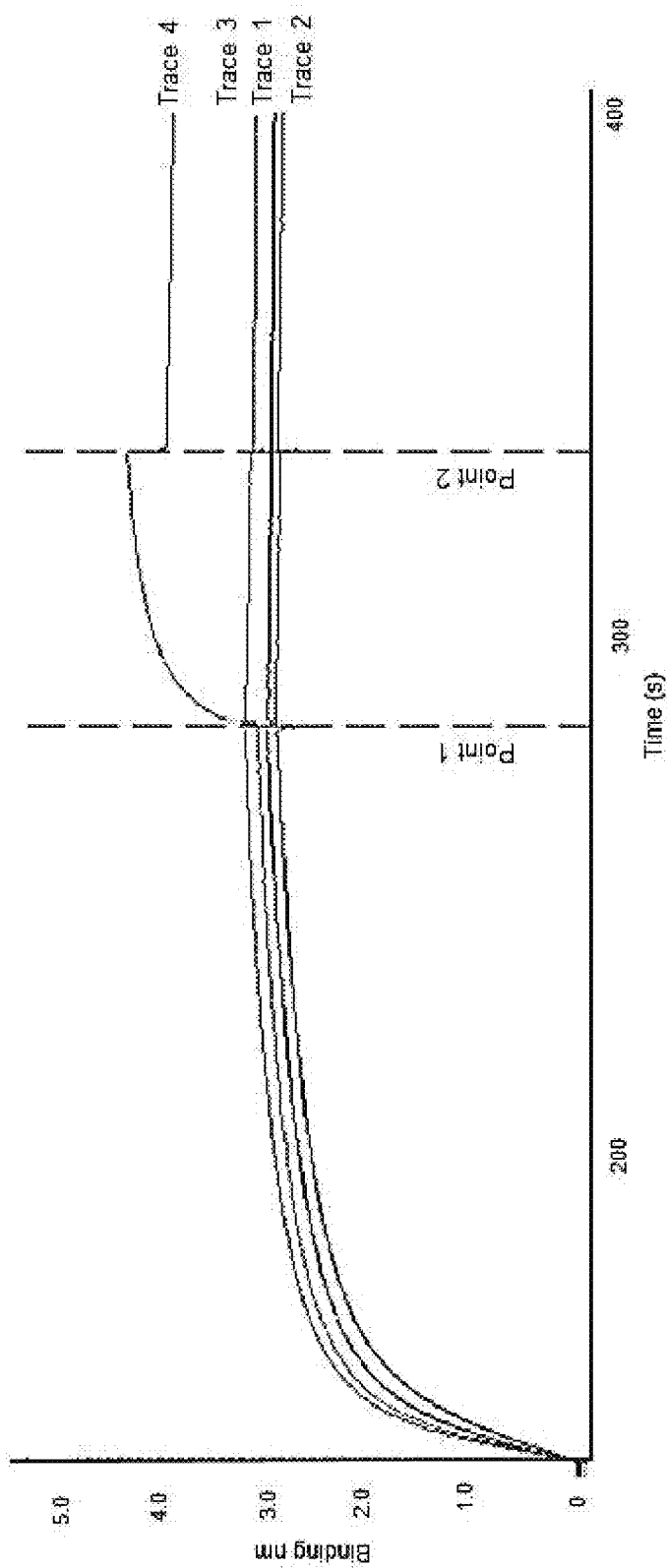
FIG. 11 shows BLitz® analysis of initial binding of the bi-specific [IgG VLDx2 (LC)] to streptavidin captured biotin labelled lysozyme followed by secondary binding to B7-1-Fc. The bi-specific has B7-1 binding VLDs fused to the D1.3 antibody [D1.3 IgG] light chains. Trace 1 is the D1.3 anti-lysozyme antibody binding to lysozyme immobilised on the biosensor surface followed by an addition of Buffer at Point 1. Trace 2 is the D1.3 anti-lysozyme antibody binding to lysozyme immobilised on the biosensor surface followed by an addition of B7-1-Fc at Point 1. B7-1-Fc was replaced with Buffer at Point 2. Trace 3 is the bi-specific—D1.3 IgG-VLDx2 (LC) binding to lysozyme immobilised on the biosensor surface followed with an addition of buffer at Point 1. Trace 4 is the bi-specific—D1.3 IgG-VLDx2 (LC) binding to lysozyme immobilised on the biosensor surface followed by an addition of B7-1-Fc at Point 1. B7-1-Fc was replaced with Buffer at Point 2. The sensorgram demonstrates simultaneous, dual target binding to lysozyme and B7-1-Fc.

FIG. 11 shows preliminary analysis using the ForteBio Blitz biosensor to demonstrate binding of the bi-specific [IgG VLDx2 (LC)] to streptavidin captured biotin labelled lysozyme followed by secondary binding to B7-1-Fc. The bi-specific has B7-1 binding VLDs coupled to the D1.3 antibody [D1.3 IgG] light chains. Trace 1 is a sensorgram of the D1.3 anti-lysozyme antibody [D1.3 IgG] used to construct the bi-specific. The antibody is shown binding to lysozyme immobilised on the biosensor surface followed by an addition of Buffer at Point 1. Trace 2 is a sensorgram of the D1.3 anti-lysozyme antibody [D1.3 IgG] used to construct the bi-specific. The antibody is shown binding to lysozyme immobilised on the biosensor surface followed by an addition of B7-1-Fc at Point 1. B7-1-Fc was replaced with Buffer at Point 2. Trace 3 is a sensorgram of the bi-specific D1.3 anti-lysozyme antibody with VLDs coupled to the antibody constant light (CL) chains [the bi-specific—D1.3 IgG-VLDx2 (LC)]. The bi-specific is shown binding to lysozyme immobilised on the biosensor surface followed with an addition of buffer at Point 1. Trace 4 is a sensorgram of the bi-specific D1.3 anti-lysozyme antibody with VLDs coupled to the antibody CL chains [the bi-specific—D1.3 IgG-VLDx2 (LC)]. The bi-specific is shown binding to lysozyme immobilised on the biosensor surface followed by an addition of B7-1-Fc at Point 1. B7-1-Fc was replaced with Buffer at Point 2.

Figure 12:
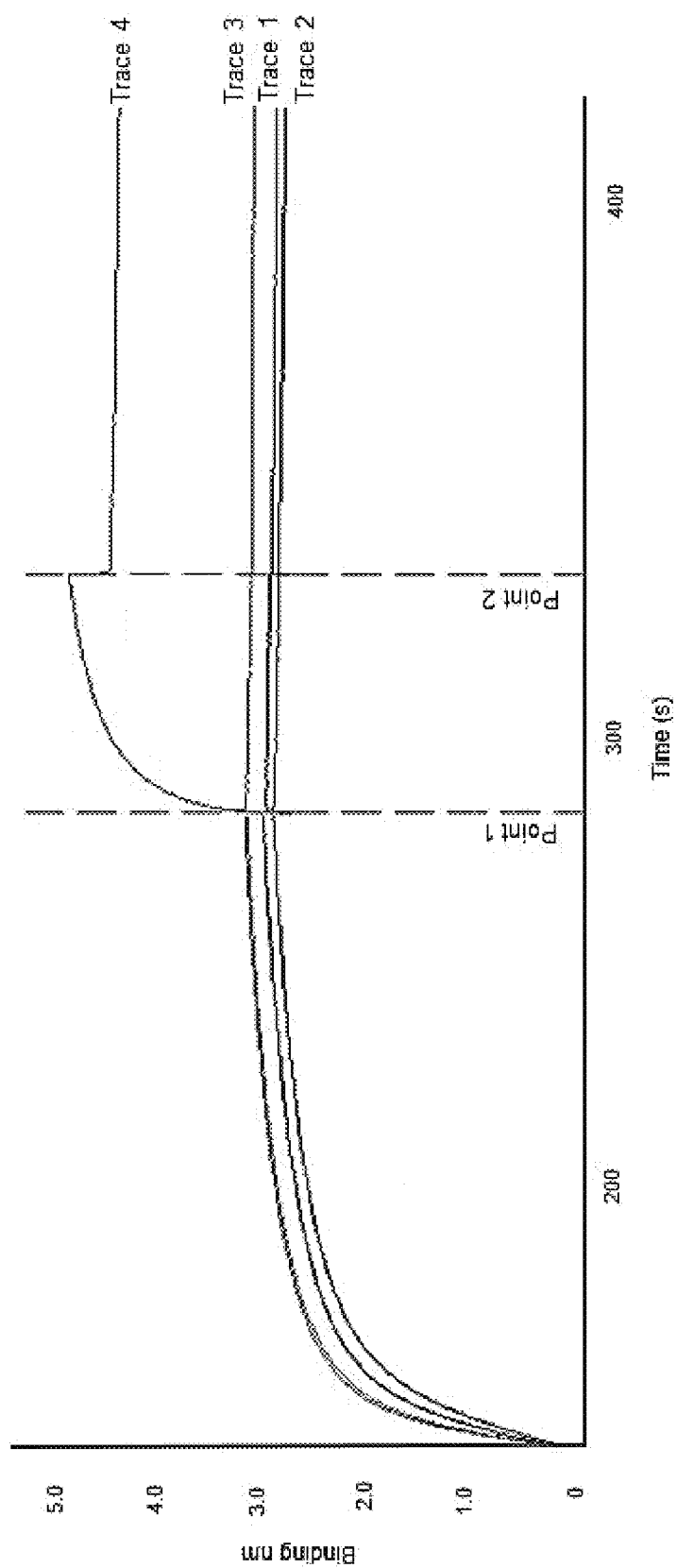
FIG. 12 shows BLitz® analysis of initial binding of the tri-specific [IgG VLDx4 (HCLC)] to streptavidin captured biotin labelled lysozyme followed by secondary binding to B7-1-Fc. The tri-specific has B7-1 binding VLDs fused to both the D1.3 antibody [D1.3 IgG] heavy chains and light chains. Trace 1 is the D1.3 anti-lysozyme antibody binding to lysozyme immobilised on the biosensor surface followed by an addition of Buffer at Point 1. Trace 2 is the D1.3 anti-lysozyme antibody binding to lysozyme immobilised on the biosensor surface followed by an addition of B7-1-Fc at Point 1. B7-1-Fc was replaced with Buffer at Point 2. Trace 3 is the tri-specific D1.3 IgG-VLDx4 (HCLC) binding to lysozyme immobilised on the biosensor surface followed with an addition of buffer at Point 1. Trace 4 is the tri-specific—D1.3 IgG-VLDx4 (HCLC) binding to lysozyme immobilised on the biosensor surface followed by an addition of B7-1-Fc at Point 1. B7-1-Fc was replaced with Buffer at Point 2. The sensorgram demonstrates simultaneous, dual target binding to lysozyme and B7-1-Fc.

FIG. 12 shows preliminary analysis using the ForteBio Blitz biosensor to demonstrate binding of the tri-specific [IgG VLDx4 (HC+LC)] to streptavidin captured biotin labelled lysozyme followed by secondary binding to B7-1-Fc. The tri-specific has B7-1 binding VLDs coupled to both the D1.3 antibody [D1.3 IgG] heavy chains and light chains. Trace 1 is a sensorgram of the D1.3 anti-lysozyme antibody [D1.3 IgG] used to construct the bi-specific. The antibody is shown binding to lysozyme immobilised on the biosensor surface followed by an addition of Buffer at Point 1. Trace 2 is a sensorgram of the D1.3 anti-lysozyme antibody [D1.3 IgG] used to construct the bi-specific. The antibody is shown binding to lysozyme immobilised on the biosensor surface followed by an addition of B7-1-Fc at Point 1. B7-1-Fc was replaced with Buffer at Point 2. Trace 3 is a sensorgram of the tri-specific D1.3 anti-lysozyme antibody with VLDs coupled to the antibody CH and CL chains [the tri-specific—D1.3 IgG-VLDx4 (HCLC)]. The tri-specific is shown binding to lysozyme immobilised on the biosensor surface followed with an addition of buffer at Point 1. Trace 4 is a sensorgram of the tri-specific D1.3 anti-lysozyme antibody with VLDs coupled to the antibody CH and CL chains [the tri-specific—D1.3 IgG-Imx4 (HC+LC)]. The tri-specific is shown binding to lysozyme immobilised on the biosensor surface followed by an addition of B7-1-Fc at Point 1. B7-1-Fc was replaced with Buffer at Point 2.

Figure 13:
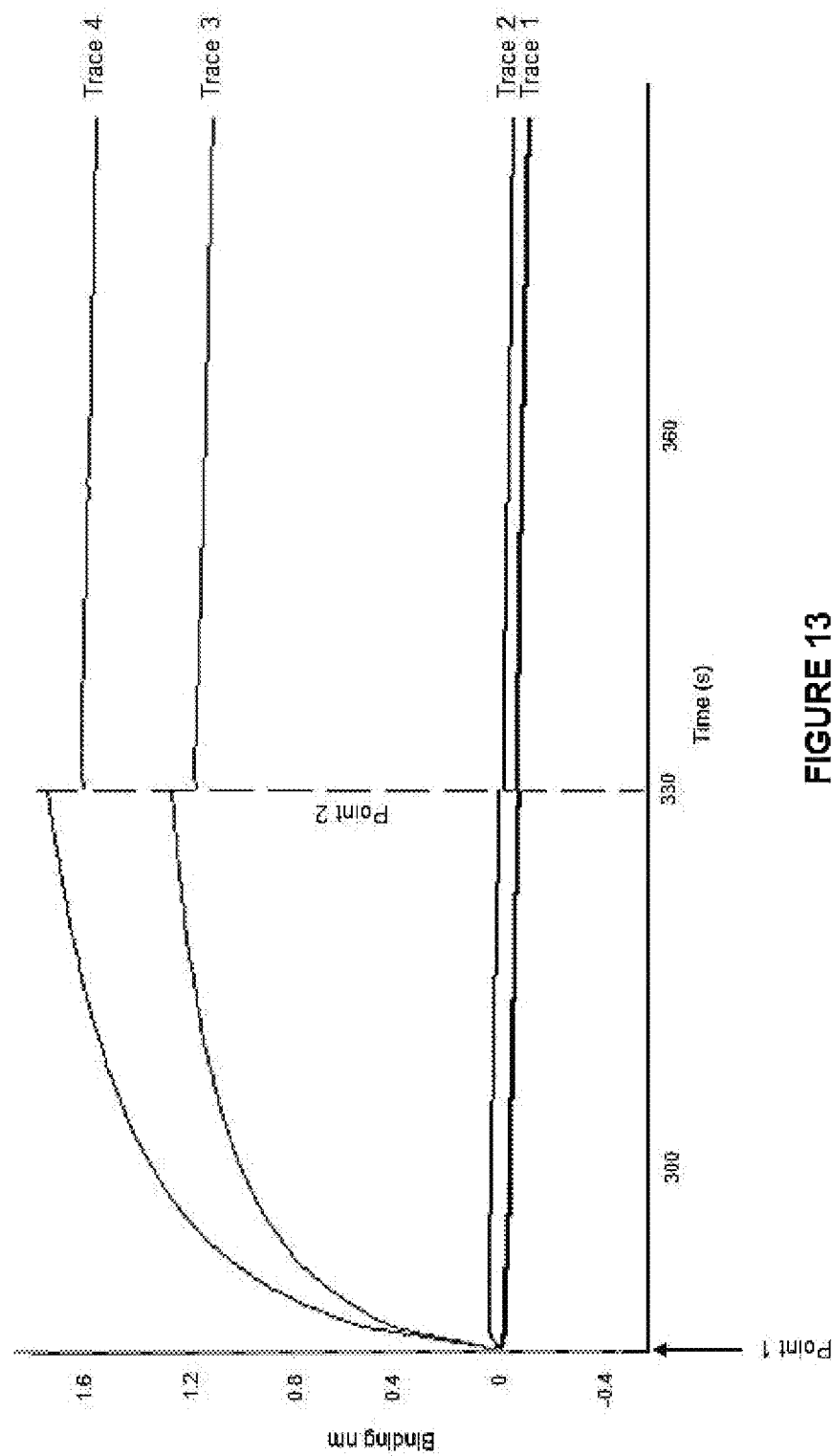
FIG. 13 shows Blitz® analysis demonstrating increased binding by the tri-specific relative to the bi-specific for B7-1-Fc. An equivalent number of antibody, bi-specific and tri-specific molecules were captured on biotin labelled lysozyme attached to a biosensor surface followed by the addition of buffer or B7-1-Fc (at Point 1) to demonstrate increased binding capacity of the tri-specific relative to the bi-specific. Trace 1 is the D1.3 anti-lysozyme antibody [D1.3 IgG] used to construct the bi-specific and tri-specific. The bound antibody is shown with Buffer only injected at Point 1. Trace 2 is the D1.3 anti-lysozyme antibody [D1.3 IgG] shown with B7-1-Fc injected at Point 1 At Point 2, B7-1-Fc was replaced with Buffer. Trace 3 is the bi-specific D1.3 anti-lysozyme antibody with VLDs fused to the antibody CL chains [the bi-specific—D1.3 IgG-VLDx2 (LC)]. The captured bi-specific is shown binding to B7-1-Fc which was injected at Point 1. At Point 2, B7-1-Fc was replaced with Buffer. Trace 4 is the tri-specific D1.3 anti-lysozyme antibody with VLDs fused to the antibody CH and CL chains [the tri-specific—D1.3 IgG-VLDx4 (HC+LC)]. The captured bi-specific is shown binding to B7-1-Fc which was injected at Point 1. At Point 2, B7-1-Fc was replaced with Buffer.
Figure 14:
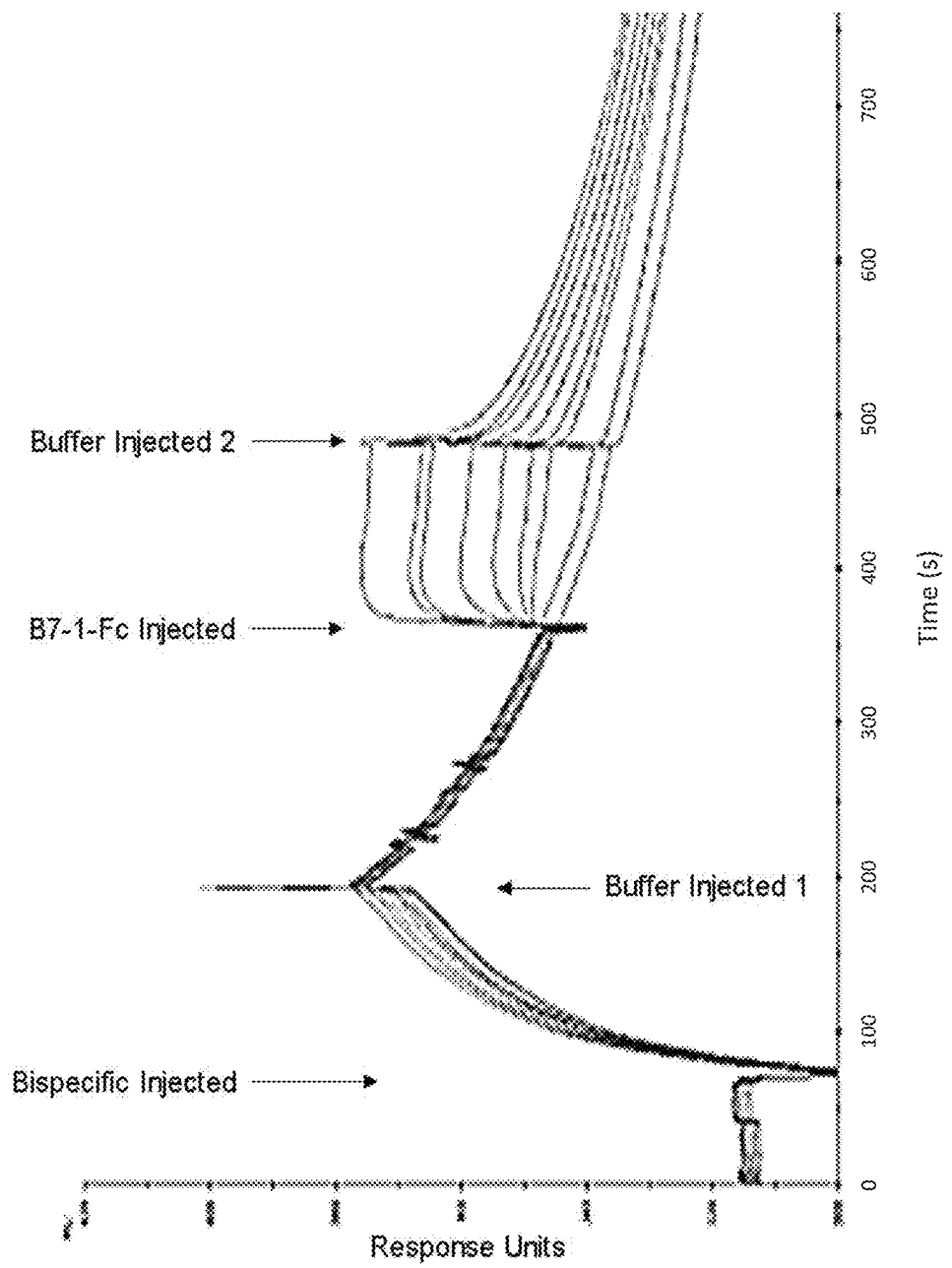
FIG. 14 shows a series of SPR binding sensorgrams that have been overlaid showing initial binding of the bi-specific [IgG VLDx2 (HC)] to streptavidin captured biotin labelled lysozyme followed by secondary binding to a concentration series of B7-1-Fc (50, 25, 12.5, 6.25, 3.125, 1.56 and 0 µg/ml). The bi-specific has B7-1 binding VLDs fused to the D1.3 antibody [D1.3 IgG] heavy chains.

FIG. 13 shows preliminary analysis using the ForteBio Blitz biosensor to demonstrate increased binding of the tri-specific molecule relative to the bi-specific molecule. The figure demonstrates increased binding levels to B7-1-Fc of the tri-specific relative to the bi-specific. An equivalent number of antibody, bi-specific and tri-specific molecules were captured on biotin labelled lysozyme attached to a biosensor surface followed by the addition of buffer or B7-1-Fc (at Point 1) to demonstrate increased binding capacity of the tri-specific relative to the bi-specific. Trace 1 is the D1.3 anti-lysozyme antibody [D1.3 IgG] used to construct the bi-specific and tri-specific. The bound antibody is shown with Buffer only injected at Point 1. Trace 2 is the D1.3 anti-lysozyme antibody [D1.3 IgG] shown with B7-1-Fc injected at Point 1 At Point 2, B7-1-Fc was replaced with Buffer. Trace 3 is the bi-specific D1.3 anti-lysozyme antibody with VLDs fused to the antibody CL chains [the bi-specific—D1.3 IgG-VLDx2 (LC)]. The captured bi-specific is shown binding to B7-1-Fc which was injected at Point 1. At Point 2, B7-1-Fc was replaced with Buffer. Trace 4 is the tri-specific D1.3 anti-lysozyme antibody with VLDs fused to the antibody CH and CL chains [the tri-specific—D1.3 IgG-VLDx4 (HCLC)]. The captured bi-specific is shown binding to B7-1-Fc which was injected at Point 1. At Point 2, B7-1-Fc was replaced with Buffer.

Example 4 Binding Affinities of the Molecules to B7.1-Fc Determined with Surface Plasmon Resonance (SPR)

The binding analysis in this section was performed on an Biacore X100 SPR instrument (GE) using standard chemistry and reagents. Concentration series traces have been overlain and all data are presented as response units (RU) after subtracting the response from a reference surface which did not contain lysozyme.

FIG. 14 shows binding of bi-specific [IgG VLDx2 (HC))] to streptavidin captured biotin labelled lysozyme followed by secondary binding to a concentration series of B7-1-Fc (50, 25, 12.5, 6.25, 3.125, 1.56 and 0 pg/ml) was determined by SPR analysis with the concentration series of SPR binding sensorgrams overlaid. The bi-specific has B7-1 binding VLDs fused to the D1.3 antibody [D1.3 IgG] heavy chains as illustrated in FIG. 2.

Bi-specific injected: is the point at which the IgG VLDx2 (HC) is added to the sensor surface. The trace shows the IgG VLDx2 (HC) binding to lysozyme immobilised on the biosensor surface.

Buffer injected 1: Point at which the injection of IgG VLDx2 (HC) is stopped and replaced with buffer. The trace shows the dissociation of the IgG VLDx2 (HC) from the lysozyme immobilised on the biosensor surface.

B7-1-Fc injected: Point at which the second analyte B7-1-Fc is added at specified concentrations (at 50, 25, 12.5, 6.25, 3.125, 1.56 and 0 uμg/ml). The trace shows B7-1-Fc binding to the IgG VLDx2 (HC) that is still bound to the lysozyme immobilised on the biosensor surface.

Buffer injected 2: Point at which the injection of B7-1-Fc is stopped and replaced with buffer. The trace shows the dissociation of B7-1-Fc from IgG VLDx2 (HC) still attached to the lysozyme immobilised on the biosensor surface.

Figure 15:
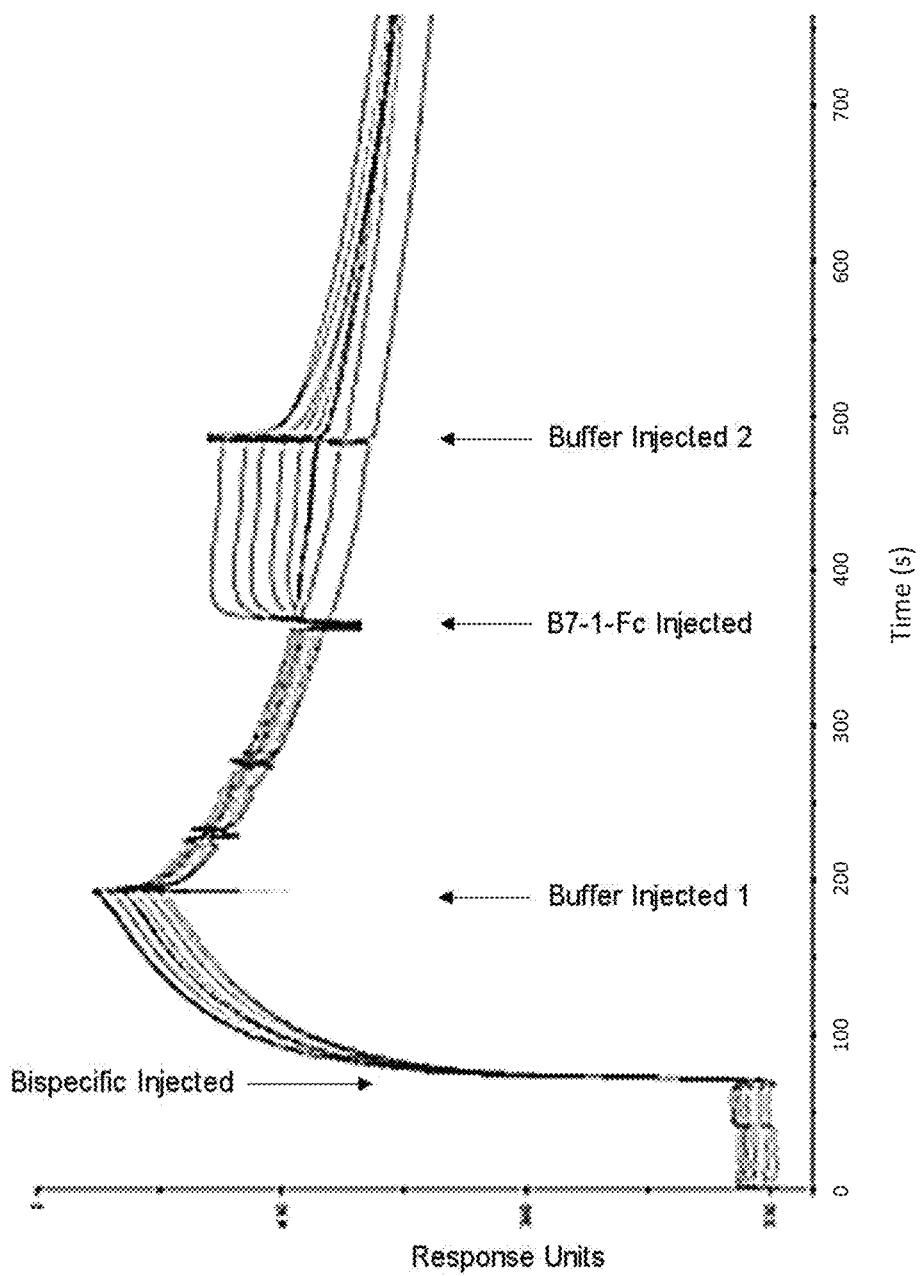
FIG. 15 shows a series of SPR binding sensorgrams that have been overlaid showing initial binding of the bi-specific [IgG VLDx2 (LC)] to streptavidin captured biotin labelled lysozyme followed by secondary binding to a concentration series of B7-1-Fc (50, 25, 12.5, 6.25, 3.125, 1.56 and 0 µg/ml). The bi-specific has B7-1 binding VLDs fused to the D1.3 antibody [D1.3 IgG] light chains.

FIG. 15 shows binding of the bi-specific [IgG VLDx2 (LC)] to streptavidin captured biotin labelled lysozyme followed by secondary binding to a concentration series of B7-1-Fc (at 50, 25, 12.5, 6.25, 3.125, 1.56 and 0 pug/ml) was determined by SPR analysis with the concentration series of SPR binding sensorgrams overlaid. The bi-specific has B7-1 binding VLDs fused to the D1.3 antibody [D1.3 IgG] light chains as illustrated in FIG. 3.

Bi-specific injected: Point at which the IgG VLDx2 (LC) is added to the sensor surface. The trace shows the IgG VLDx2 (LC) binding to lysozyme immobilised on the biosensor surface. Buffer injected 1: Point at which the injection of IgG VLDx2 (LC) is stopped and replaced with buffer. The trace shows the dissociation of the IgG VLDx2 (LC) from the lysozyme immobilised on the biosensor surface.

B7-1-Fc injected: Point at which the second analyte B7-1-Fc is added at specified concentrations (at 50, 25, 12.5, 6.25, 3.125, 1.56 and 0 pg/ml). The trace shows B7-1-Fc binding to the IgG VLDx2 (LC) that is still bound to the lysozyme immobilised on the biosensor surface.

Buffer injected 2: Point at which the injection of B7-1-Fc is stopped and replaced with buffer.

The trace shows the dissociation of B7-1-Fc from IgG VLDx2 (LC) still attached to the lysozyme immobilised on the biosensor surface.

Figure 16:
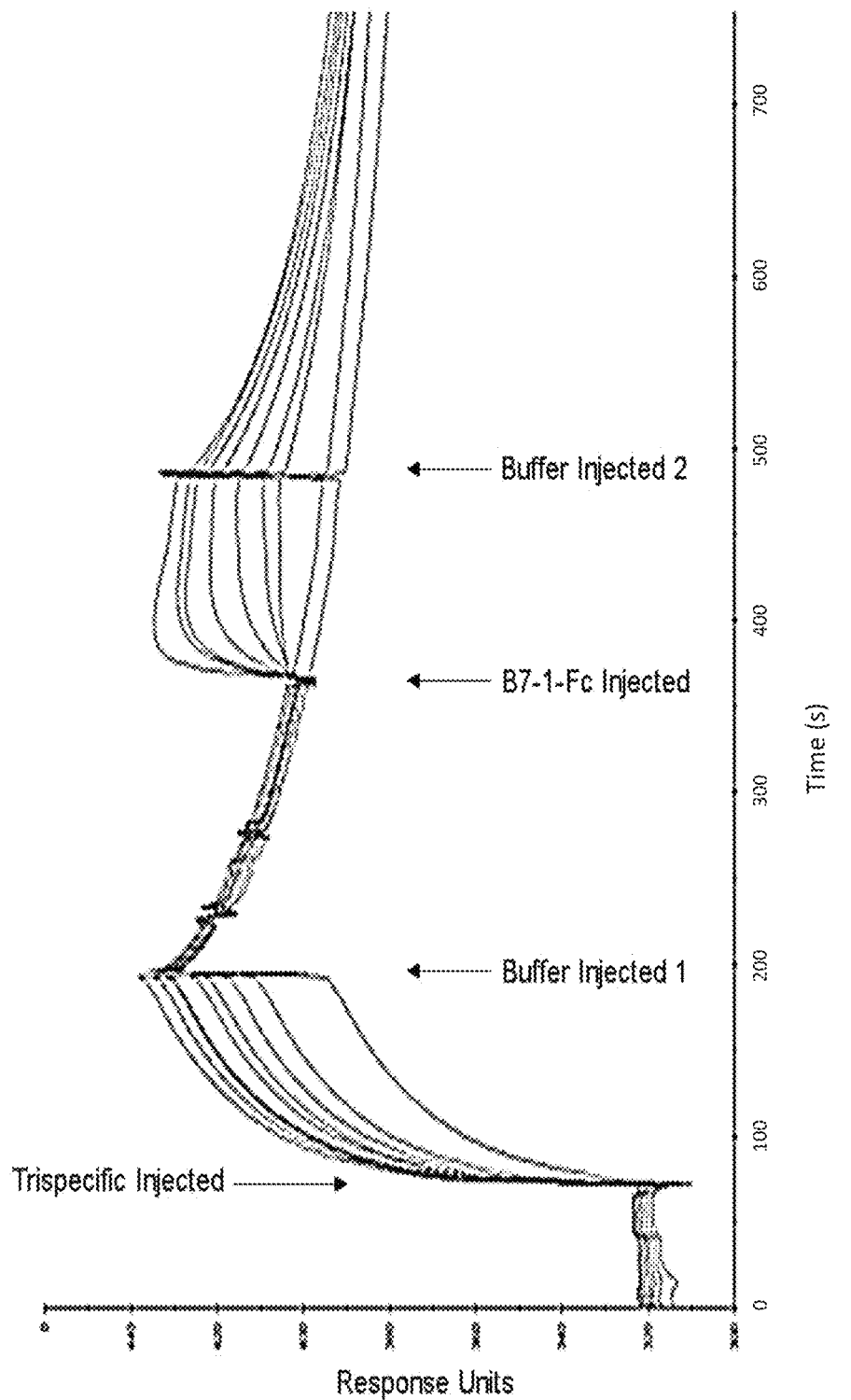
FIG. 16 shows a series of SPR binding sensorgrams that have been overlaid showing initial binding of the tri-specific [IgG VLDx4 (HC+LC)] to streptavidin captured biotin labelled lysozyme followed by secondary binding to a concentration series of B7-1-Fc (50, 25, 12.5, 6.25, 3.125, 1.56 and 0 µg/ml). The tri-specific has B7-1 binding VLDs fused to both the D1.3 antibody [D1.3 IgG] heavy and light chains.

FIG. 16 shows binding of the tri-specific [IgG VLDx4 (HC+LC)] to streptavidin captured biotin labelled lysozyme followed by secondary binding to a concentration series of B7-1-Fc (at 25, 12.5, 6.25, 3.125, 1.56 and 0 pg/ml) was determined by SPR analysis with the concentration series of SPR binding sensorgrams overlaid. The tri-specific has B7-1 binding VLDs fused to both the D1.3 antibody [D1.3 IgG] heavy and light chains as illustrated in FIG. 4.

Tri-specific injected: Point at which the IgG VLDx4 (HC+LC) is added to the sensor surface. The trace shows the IgG Imx4 (HCLC) binding to lysozyme immobilised on the biosensor surface.

Buffer injected 1: Point at which the injection of IgG VLDx4 (HC+LC) is stopped and replaced with buffer. The trace shows the dissociation of the IgG VLDx4 (HC+LC) from the lysozyme immobilised on the biosensor surface B7-1-Fc injected: Point at which the second analyte B7-1-Fc is added at specified concentrations (at 25, 12.5, 6.25, 3.125, 1.56 and 0 pg/ml). The trace shows B7-1-Fc binding to the IgG VLDx4 (HC+LC) that is still bound to the lysozyme immobilised on the biosensor surface. Buffer injected 2: Point at which the injection of B7-1-Fc is stopped and replaced with buffer. The trace shows the dissociation of B7-1-Fc from IgG VLDx4 (HC+LC) still attached to the lysozyme immobilised on the biosensor surface The binding properties of the purified Fab, Fab-VLD bi-specific and tri-specific molecules were also characterised using surface plasmon resonance (SPR).

Figure 17:
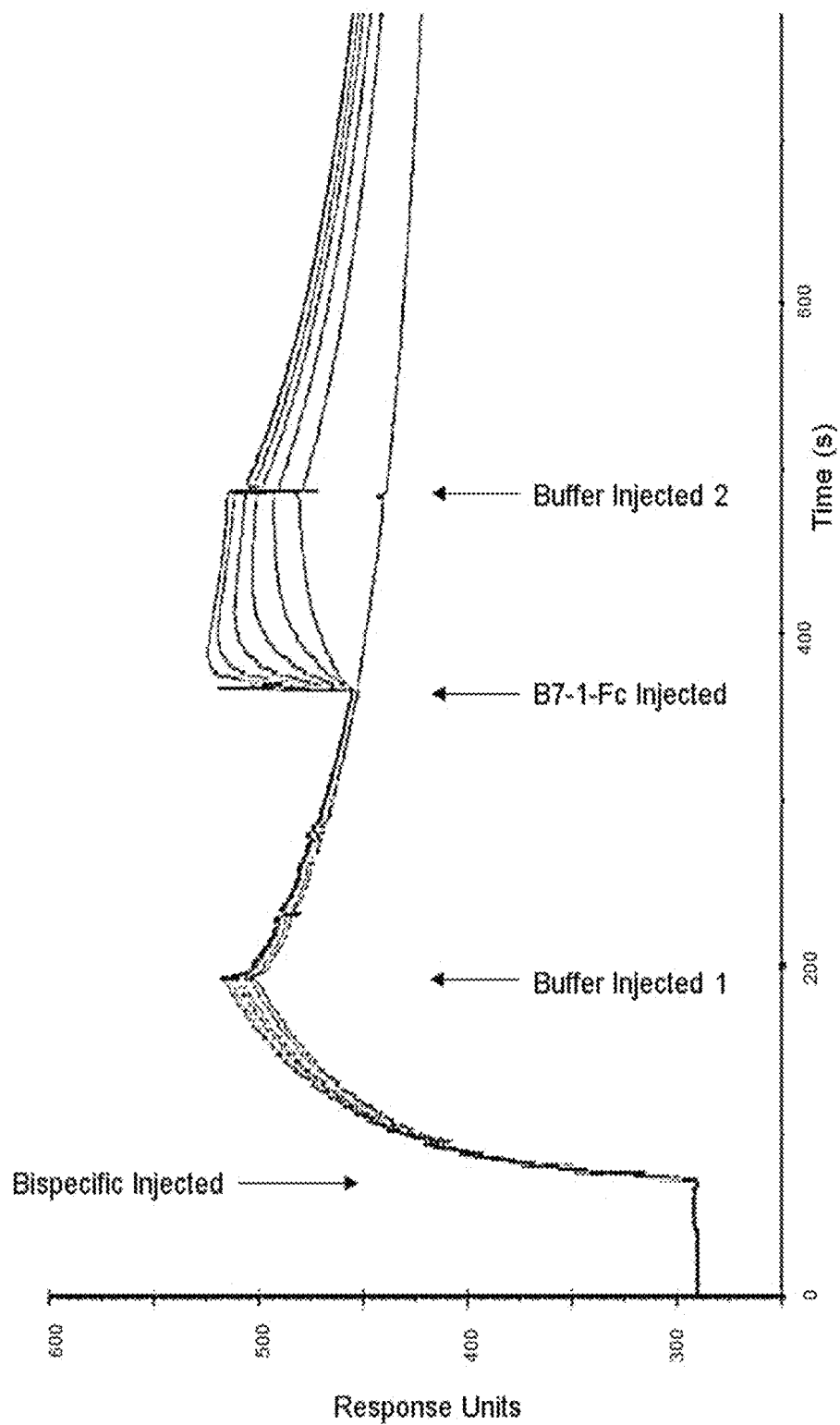
FIG. 17 shows overlapped SPR binding sensorgrams showing the bi-specific [Fab-VLDx1 (HC)] binding to lysozyme followed by simultaneous binding of a concentration series of B7-1-Fc (at 25, 12.5, 6.25, 3.125, 1.56 µg/ml). The bi-specific has a B7-1 binding VLD fused to the D1.3 Fab [D1.3 Fab] heavy chain.

FIG. 17 shows a series of SPR binding sensorgrams that have been overlaid demonstrating initial binding of the bi-specific [Fab-VLDx1 (HC)] to streptavidin captured biotin labelled lysozyme followed by secondary binding to a concentration series of B7-1-Fc (at 25, 12.5, 6.25, 3.125, 1.56 and 0 ug/ml). The bi-specific has a B7-1 binding VLD fused to the D1.3 Fab [D1.3 Fab] heavy chain as illustrated in FIG. 5.

Bi-specific Injected: Point at which the Fab-VLDx1 (HC) is added to the sensor surface. The trace shows the Fab-VLDx1(HC) binding to lysozyme immobilised on the biosensor surface. Buffer Injected 1: Point at which the injection of Fab-VLDx1(HC) is stopped and replaced with buffer. The trace shows the dissociation of the Fab-VLDx1(HC) from the lysozyme immobilised on the biosensor surface B7-1-Fc Injected: Point at which the second analyte B7-1-Fc is added at specified concentrations (at 25, 12.5, 6.25, 3.125, 1.56 and 0 ug/ml). The trace shows B7-1-Fc binding to the Fab-VLDx1 (HC) that is still bound to the lysozyme immobilised on the biosensor surface. Buffer Injected 2: Point at which the injection of B7-1-Fc is stopped and replaced with buffer. The trace shows the dissociation of B7-1-Fc from Fab-VLDx1(HC) still attached to the lysozyme immobilised on the biosensor surface.

Figure 18:
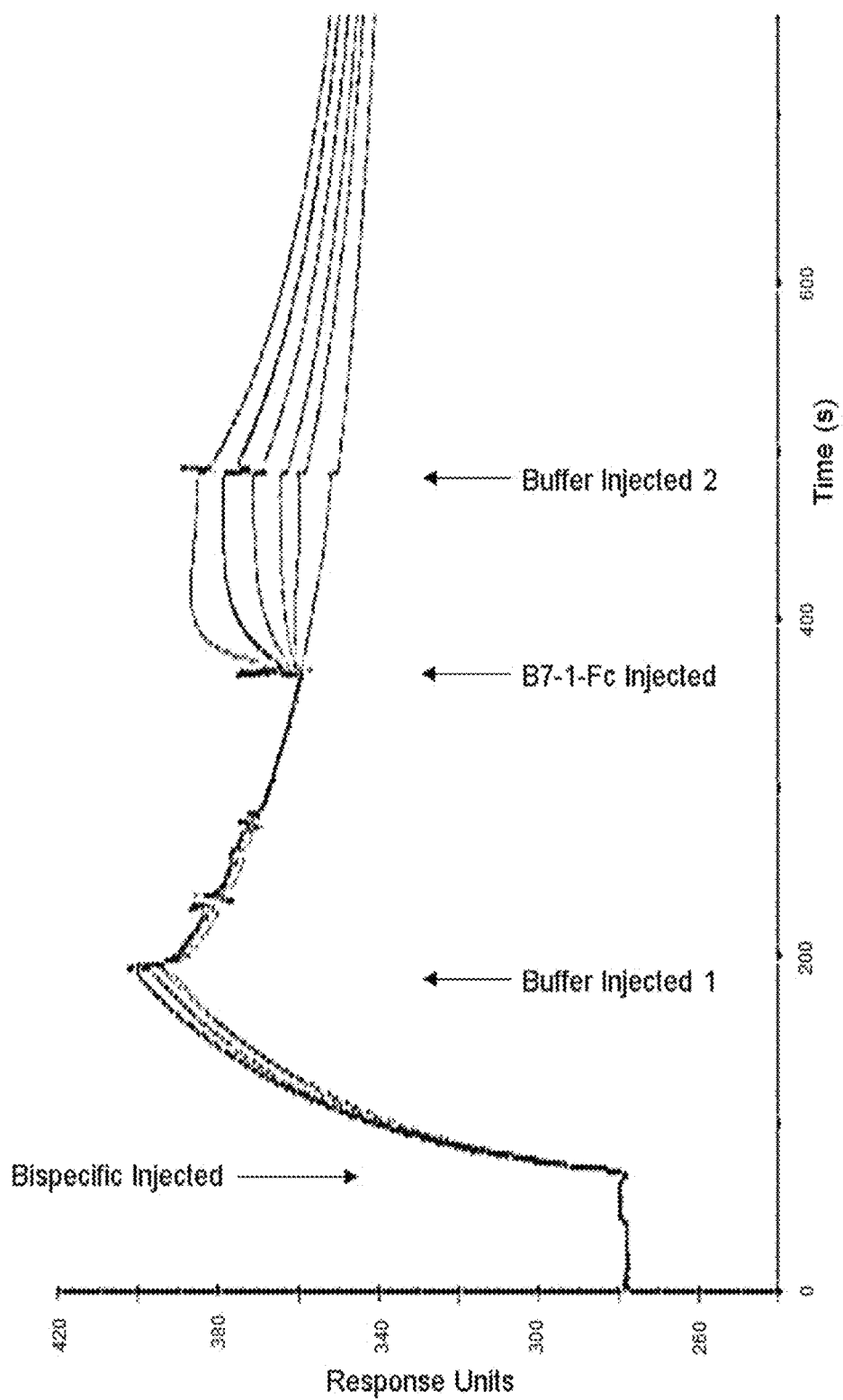
FIG. 18 shows overlapped SPR binding sensorgrams showing the bi-specific [Fab-VLDx1 (LC)] binding to lysozyme followed by simultaneous binding of a concentration series of B7-1-Fc (at 25, 12.5, 6.25, 3.125, 1.56 µg/ml). The bi-specific has a B7-1 binding VLD fused to the D1.3 Fab [D1.3 Fab] light chain.

FIG. 18 shows a series of SPR binding sensorgrams that have been overlaid demonstrating initial binding of the bi-specific [Fab-VLDx1 (LC)] to streptavidin captured biotin labelled lysozyme followed by secondary binding to a concentration series of B7-1-Fc (at 25, 12.5, 6.25, 3.125, 1.56 and 0 ug/ml). The bi-specific has a B7-1 binding VLD fused to the D1.3 Fab [D1.3 Fab] light chain as illustrated in FIG. 6.

Bi-specific Injected: Point at which the Fab-VLDx1 (LC) is added to the sensor surface. The trace shows the Fab-VLDx1 (LC) binding to lysozyme immobilised on the biosensor surface. Buffer Injected 1: Point at which the injection of Fab-VLDx1 (LC) is stopped and replaced with buffer. The trace shows the dissociation of the Fab-VLDx1 (LC) from the lysozyme immobilised on the biosensor surface.

B7-1-Fc Injected: Point at which the second analyte B7-1-Fc is added at specified concentrations (at 25, 12.5, 6.25, 3.125, 1.56 and 0 ug/ml). The trace shows B7-1-Fc binding to the Fab-VLDx1 (LC) that is still bound to the lysozyme immobilised on the biosensor surface. Buffer Injected 2: Point at which the injection of B7-1-Fc is stopped and replaced with buffer. The trace shows the dissociation of B7-1-Fc from Fab-VLDx1 (LC) still attached to the lysozyme immobilised on the biosensor surface.

Figure 19:
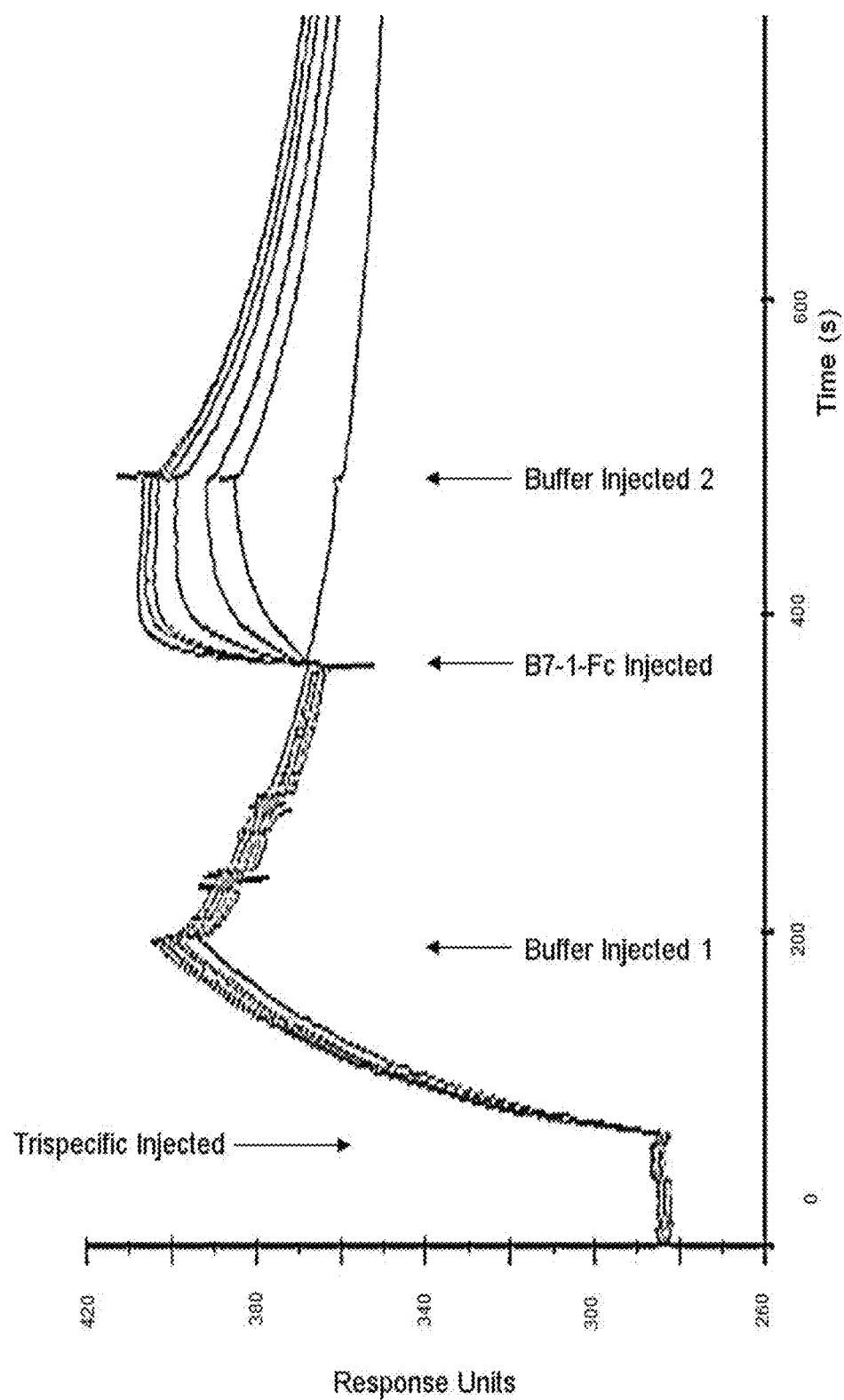
FIG. 19 shows overlapped SPR binding sensorgrams showing the tri-specific [Fab-VLDx2(HC+LC)] binding to lysozyme followed by simultaneous binding of a concentration series of B7-1-Fc (at 25, 12.5, 6.25, 3.125, 1.56 µg/ml). The tri-specific has B7-1 binding VLDs fused to both the D1.3 Fab [D1.3 Fab] heavy and light chains.

FIG. 19 shows a series of SPR binding sensorgrams that have been overlaid demonstrating initial binding of the tri-specific [Fab-VLDx2(HC+LC)] to streptavidin captured biotin labelled lysozyme followed by secondary binding to a concentration series of B7-1-Fc (at 25, 12.5, 6.25, 3.125, 1.56 and 0 µg/ml). The tri-specific has B7-1 binding VLDs fused to both the D1.3 Fab [D1.3 Fab] heavy and light chains as illustrated in FIG. 7.

Tri-specific Injected: Point at which the Fab-VLDx2(HC+LC) is added to the sensor surface. The trace shows the Fab-VLDx2(HC+LC) binding to lysozyme immobilised on the biosensor surface.

Buffer Injected 1: Point at which the injection of Fab-VLDx2(HC+LC) is stopped and replaced with buffer. The trace shows the dissociation of the Fab-VLDx2(HC+LC) from the lysozyme immobilised on the biosensor surface B7-1-Fc Injected: Point at which the second analyte B7-1-Fc is added at specified concentrations (at 25, 12.5, 6.25, 3.125, 1.56 and 0 µg/ml). The trace shows B7-1-Fc binding to the Fab-VLDx2(HC+LC) that is still bound to the lysozyme immobilised on the biosensor surface.

Buffer injected 2: Point at which the injection of B7-1-Fc is stopped and replaced with buffer. The trace shows the dissociation of B7-1-Fc from Fab-VLDx2(HC+LC) still attached to the lysozyme immobilised on the biosensor surface.

Example 5 Binding Stoichiometry of the Molecules

Figure 20:
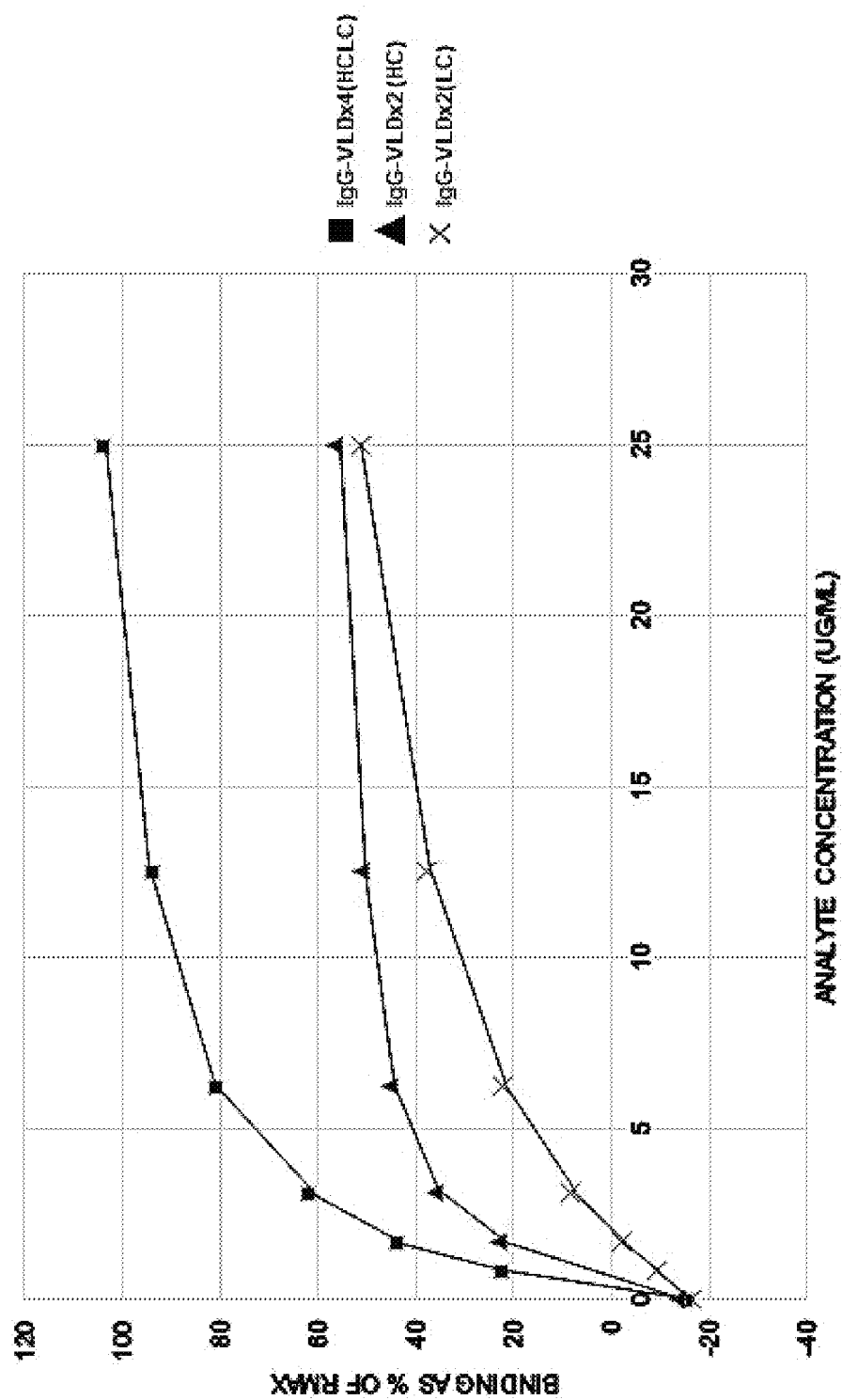
FIG. 20 shows the binding stoichiometry determined as a percentage of $R_{MAX}$ (maximal capacity) determined by SPR analysis for the bi-specific and tri-specific antibody-VLD molecules binding to B7-1-Fc.

Binding stoichiometry of the bi-specific [IgG VLDx2 (HC)] and tri-specific [IgG Imx4 (HC+LC)] for B7-1-Fc were also determined by SPR (FIG. 20). The kinetic assays were performed for IgG-VLDx2 (HC), IgG-VLDx2 (LC) and IgG-VLDx4 (HCLC) by capturing on a biotin-lysozyme surface, and running a series of concentrations of B7-1-Fc (50, 25, 12.5, 6.25, 3.125, 1.56 and 0 pg/ml) as the analyte. The theoretical maximum binding signal for the analyte (Rmax) was calculated based on the amount of captured IgG-VLD protein, accounting for the molecular weight of the analyte and ligand.

Assuming a 1:1 stoichiometry for all samples, the binding level of analyte to ligand was plotted as a percentage of the Rmax value, for each concentration. As the analyte concentration increased to 25 µg/ml, the binding levels neared saturation or equilibrium levels. The equilibrium binding level for the tetravalent protein, IgG-VLDx4(HC+LC) (103.9% of Rmax) was around double that of the bivalent proteins IgG-VLDx2(HC) (56.7%) and IgG-VLDx2(LC) (51.4%). This suggests that IgG-VLDx4(HC+LC) is able to bind B7.1-Fc through the heavy and light chain-fused VLD domains simultaneously.

Figure 21:
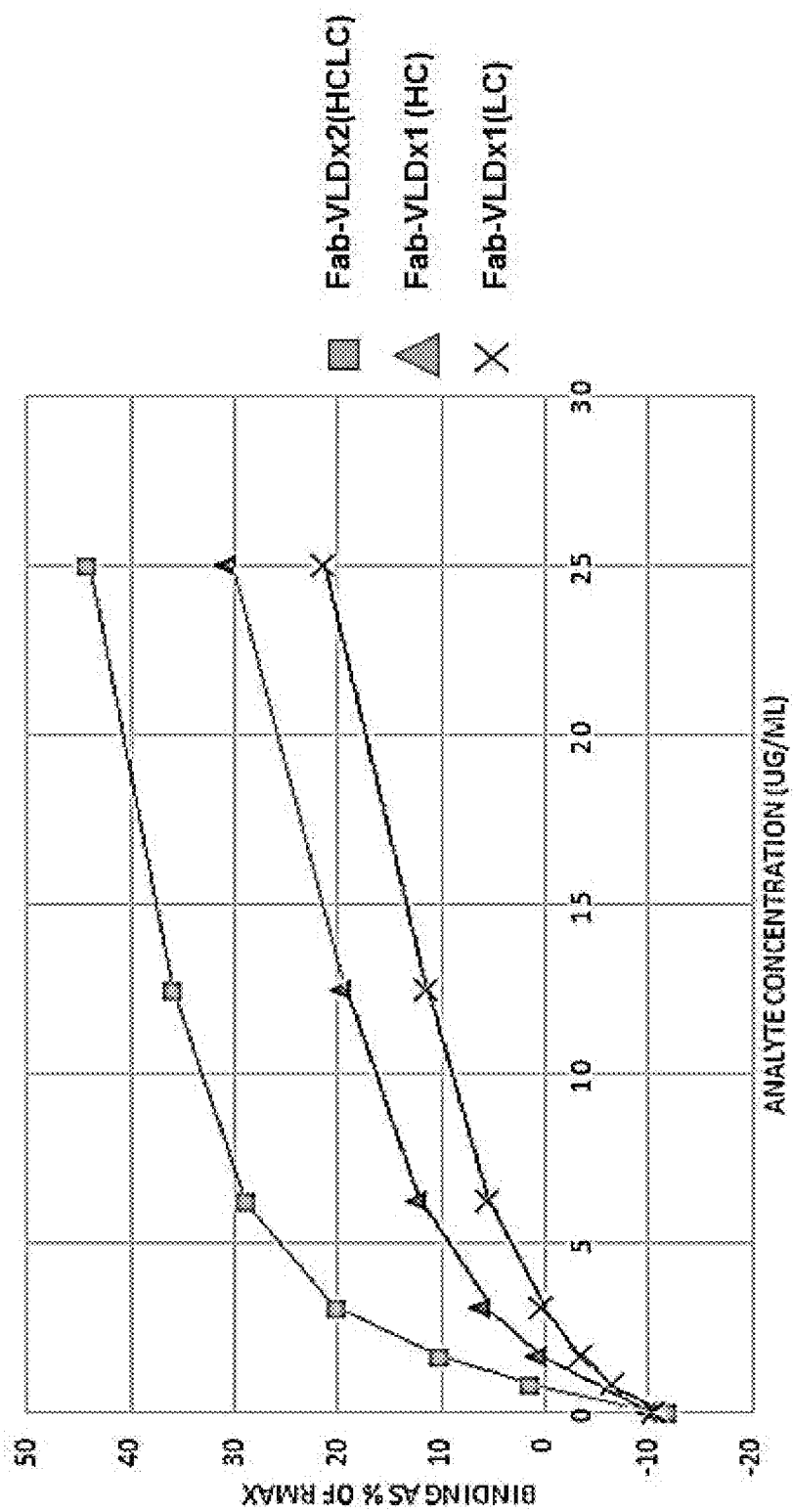
FIG. 21 shows the binding stoichiometry determined as a percentage of $R_{MAX}$ determined by SPR analysis for the bi-specific and tri-specific Fab-VLD molecules binding to B7-1-Fc.

Binding stoichiometry of the bi-specific [Fab-VLDx1 (HC)], [Fab-VLDx1 (LC)] and [Fab-VLDx2 (HC+LC)] to B7-1-Fc is shown in FIG. 21. The results suggest that Fab-VLDx2 (HC+LC) was able to bind B7.1 through the heavy and light chain-fused VLD domains simultaneously.

Example 6 Binding Affinities of the Molecules to B7.1-Fc

The binding kinetics of the antibody-VLD bi-specific and tri-specific molecules and the Fab-VLD bi-specific and tri-specific molecules was determined by surface plasmon resonance. The association constant (Ka), dissociation constant (Kd) and equilibrium dissociation constant/binding constant $K_D$ are shown in Tables 3 and 4 respectively.

TABLE 3

Affinity of the antibody-VLD molecules for B7.1-Fc

| Ligand | Ka (1/Ms) | Kd (1/s) | $K_D$ (nM) |
| --- | --- | --- | --- |
| IgG VLDx2 (HC) | $5.16 \times 10^5$ | $2.80 \times 10^{-3}$ | 5.44 |
| IgG VLDx2 (LC) | $1.63 \times 10^5$ | $4.00 \times 10^{-3}$ | 24.5 |
| IgG VLDx4 (HC + LC) | $5.30 \times 10^5$ | $2.90 \times 10^{-3}$ | 5.47 |

The results demonstrate that the binding affinity of the tri-specific molecule IgG VLDx4 (HC+LC) and bi-specific molecule IgG VLDx2 (HC) for B7-1-Fc was comparable.

TABLE 4

Affinity of the Fab-VLD molecules for B7.1-Fc

| Ligand | Ka (1/Ms) | Kd (1/s) | $K_D$ (nM) |
| --- | --- | --- | --- |
| Fab VLDx1 (HC) | $5.26 \times 10^5$ | $2.85 \times 10^{-3}$ | 5.41 |
| Fab VLDx1 (LC) | $2.18 \times 10^5$ | $2.96 \times 10^{-3}$ | 13.6 |
| Fab VLDx2 (HC + LC) | $4.45 \times 10^5$ | $4.33 \times 10^{-3}$ | 9.73 |

The results demonstrate that the binding affinity of the tri-specific molecule Fab VLDx4 (HC+LC) and bi-specific molecule Fab VLDx1 (HC) for B7-1-Fc was comparable.

Example 7 Analysis of Tri-Specific Binding

The IgG VLDx4 (HCLC) construct was modified whereby sclerostin (Scl) binding VLDs were coupled to the C terminus of the heavy chains of the anti-lysozyme antibody D1.3 and B7-1 binding VLDs were coupled to the antibody constant light (CL) chains of an anti-lysozyme antibody. This tri-specific molecule was designated [IgG VLDx4 (Scl-HC)(B7-LC)].

The sequence of the anti-Lysozyme IgG1 heavy chain fused to anti-Sclerostin VLD '1E1' is shown below (SEQ ID NO:25):

```
EVKLQESGPGLVAPSQSLSITCTVSGFSLTGYGVNWVRQPPGKGLEWLG
MIWGDGNTDYNSALKSRLSISKDNSKSQVFLKMNSLHTDDTARYYCARE
RDYRLDYWGQGTTVTVSSASTKGPSVFPLAPSSKSTSGGTAALGCLVKD
YFPEPVTVSWNSGALTSGVHTFPAVLQSSGLYSLSSVVTVPSSSLGTQT
YICNVNHKPSNTKVDKKVEPPKSCDKTHTCPPCPAPELLGGPSVFLFPP
KPKDTLMISRTPEVTCVVVDVSHEDPEVKFNWYVDGVEVHNAKTKPREE
QYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSL
SLSPGKSGGGGSGGGGSGGGGSKAMHVAQPAVVLASSRGIASFVCEYTV
SWVDMEVRVTVLRQADSQVIEVCAATYWNGRWLTFLDDSICTGTSSGNQ
VNLTIQGLRAMDTGLYICKVQLDPSWGYYWQGYEGIGNGTQIYVIDPEP
SPDSN
```

The sequence of the anti-sclerostin VLD is shown below:
(SEQ ID NO: 14)
```
KAMHVAQPAVVLASSRGIASFVCEYTVSWVDMEVRVTVLRQADSQVTEV
CAATYWNGRWLTFLDDSICTGTSSGNQVNLTIQGLRAMDTGLYICKVQL
DPSWGYYWQGYEGIGNGTQIYVIDPEPSPDSN
```
The VLD binding loops of SEQ ID NO: 25 and SEQ ID NO: 14 are underlined.

For analysis of simultaneous trio binding of lysozyme, B7-1 and sclerostin, analysis was performed on an Biacore X100 SPR instrument (GE). The antibody-Imunexin protein was injected at 35 pg/ml over a streptavidin sensor chip surface, onto which biotinylated lysozyme had been captured on flow cell 2 (approximately 200 RU). The antibody-Imunexin protein was injected, followed by a stabilisation period. The first analyte, B7.1-Fc was injected at a concentration of 25 pg/ml. A control cycle was performed in which buffer alone was injected instead of B7.1-Fc. The second analyte, sclerostin (R&D Systems catalogue number 1406-ST/CF), was then injected at 15 pg/ml immediately for 60s with 120s dissociation time. A control cycle was performed in which buffer alone was injected instead of sclerostin.

The surface was regenerated by injecting 10 mM Glycine buffer at pH 2.1 for 30 seconds.

All data are presented as response units (RU) after subtracting the response from a reference surface (flow cell 1) which did not contain lysozyme.

(a) Analysis of Tri-Specific Binding of Full Length Antibody Constructs

Figure 22:
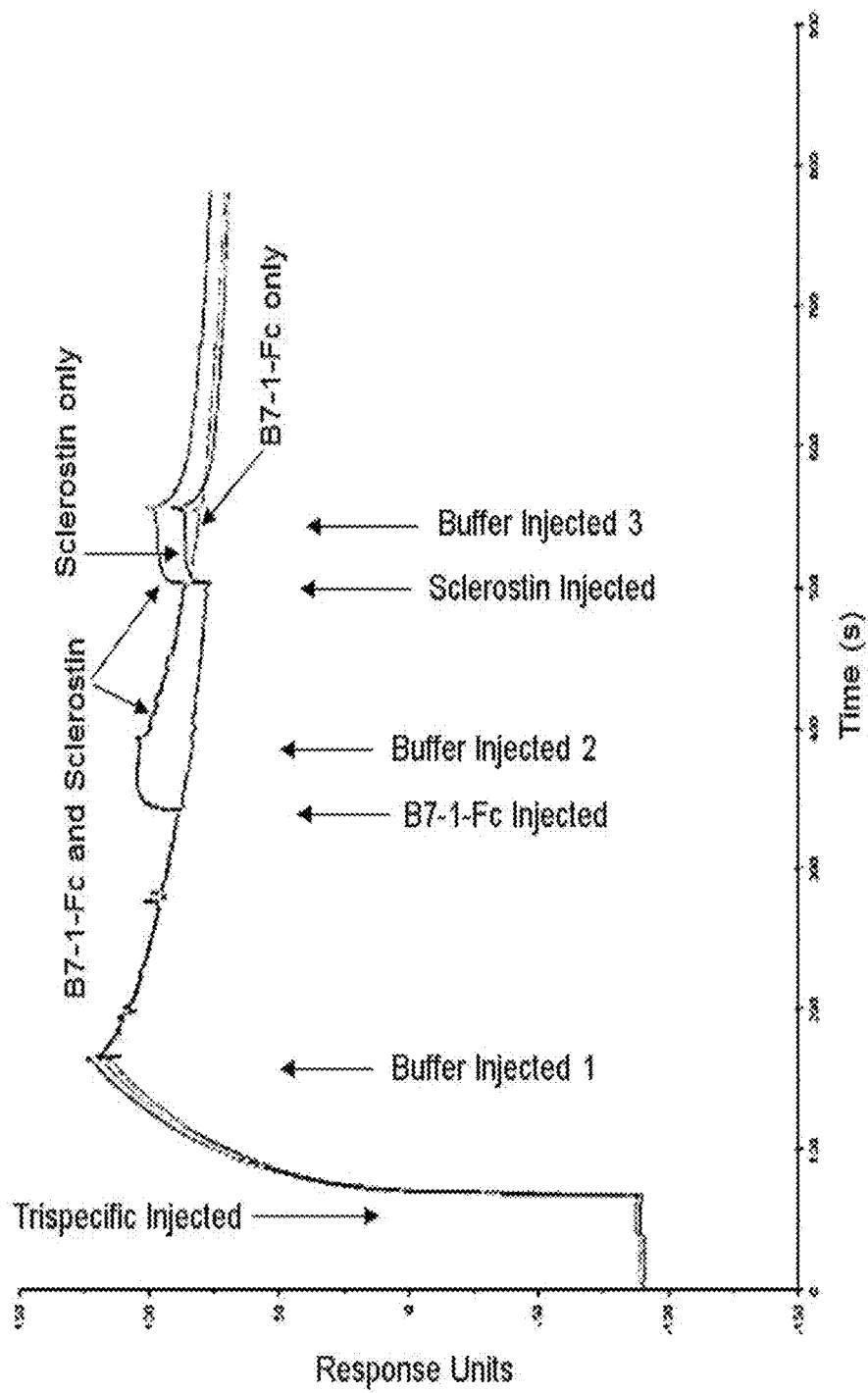
FIG. 22 shows a series of SPR binding sensorgrams that have been overlaid demonstrating initial binding of the tri-specific [IgG VLDx4 (Scl-HC)(B7-LC)] to streptavidin captured biotin labelled lysozyme followed by sequential and simultaneous binding to B7-1-Fc and sclerostin. The tri-specific has sclerostin (Scl) binding VLDs fused to the D1.3 antibody [D1.3 IgG] heavy chains and B7-1 binding VLD's fused to the light chains. The B7-1-Fc only trace is a sensorgram of the tri-specific showing binding to lysozyme immobilised on the biosensor surface followed by the addition of B7-1-Fc. The sensorgram demonstrates simultaneous, dual target binding to lysozyme and B7-1-Fc. The Sclerostin only trace is a sensorgram of the tri-specific showing binding to lysozyme immobilised on the biosensor surface followed by the addition of sclerostin. The sensorgram demonstrates simultaneous, dual target binding to lysozyme and sclerostin. The B7-1-Fc and Sclerostin trace is a sensorgram of the tri-specific showing binding to lysozyme immobilised on the biosensor surface followed by the addition of B7-1-Fc, and then followed by the addition of sclerostin. The sensorgram demonstrates simultaneous, trio target binding to lysozyme and B7-1-Fc and sclerostin.

FIG. 22 shows a series of SPR binding sensorgrams that have been overlaid demonstrating initial binding of the tri-specific [IgG VLDx4 (Scl-HC)(B7-LC)] to streptavidin captured biotin labelled lysozyme followed by simultaneous binding to B7-1-Fc and sclerostin. The tri-specific has sclerostin binding VLDs fused to the D1.3 antibody [D1.3 IgG] heavy chains and B7-1 binding VLD's fused to the light chains.

The B7-1-Fc only trace is a sensorgram of the tri-specific showing binding to lysozyme immobilised on the biosensor surface followed by the addition of B7-1-Fc. The sensorgram demonstrates simultaneous, dual target binding to lysozyme and B7-1-Fc.

The Sclerostin only trace is a sensorgram of the tri-specific showing binding to lysozyme immobilised on the biosensor surface followed by the addition of sclerostin. The sensorgram demonstrates simultaneous, dual target binding to lysozyme and sclerostin.

The B7-1-Fc and Sclerostin trace is a sensorgram of the tri-specific showing binding to lysozyme immobilised on the biosensor surface followed by the addition of B7-1-Fc, and then followed by the addition of sclerostin. The sensorgram demonstrates simultaneous, trio target binding to lysozyme and B7-1-Fc and sclerostin.

Binding of the molecule to B7-1 and sclerostin was examined by SPR as shown in FIG. 22. The results show that the tri-specific was capable of simultaneous binding to both B7-1 and sclerostin.

(b) Analysis of Tri-Specific Binding of Fab Construct

The Fab VLDx2 (HC+LC) construct was modified whereby a B7-1 binding VLD was coupled to the C terminus of the heavy chain of the anti-lysozyme Fab D3.1 and a sclerostin (Scl) binding VLD was coupled to the Fab constant light (CL) chain of an anti-lysozyme Fab. This tri-specific molecule was designated [Fab VLDx2 (B7-1-HC) (Scl-LC)]. A second construct was made whereby a sclerostin binding VLD was coupled to the C terminus of the heavy chain of the anti-lysozyme Fab D3.1 and a B7-1 binding VLD was coupled to the Fab constant light (CL) chain of an anti-lysozyme Fab. This tri-specific molecule was designated [Fab VLDx2 (Scl-HC)(B7-1-LC)]

FIG. 23 shows binding analysis for the tri-specific Fab VLDx2 (B7-1-HC)(Scl-LC) and FIG. 24 shows the binding analysis for the tri-specific Fab VLDx2 (Scl-HC)(B7-1-LC). Binding analysis was performed using the ForteBio Blitz. The binding traces demonstrate initial binding of the tri-specifics (Fab VLDx2 (B7-HC)(Scl-LC) in FIG. 23 and Fab VLDx2 (Scl-HC)(B7-1-LC) in FIG. 24) to streptavidin captured biotin labelled lysozyme followed by sequential and simultaneous binding to B7-1-Fc and sclerostin. The biosensor traces show the tri-specifics initially binding to lysozyme immobilised on the biosensor surface followed by binding to B7-1-Fc (B7-1-Fc was added at the point indicated). The binding traces demonstrate simultaneous, dual target binding to lysozyme and B7-1-Fc. Sclerostin is subsequently added at the point indicated and the biosensor trace shows simultaneous, tri-target binding to lysozyme and B7-1-Fc and sclerostin for both the Fab VLDx2 (B7-1-HC) (Scl-LC) and Fab VLDx2 (Scl-HC)(B7-1-LC) molecules. Finally, sclerostin is replaced with buffer to show the dissociation rate.

Example 8 Generation of Human Serum Albumin-VLD Fusion Proteins Methods

FIG. 25 shows a schematic of a protein coupled to a VLD according to one example of the disclosure. The bi-specific can bind to both Target A and B either individually or at the same time.

Vector Generation

Sequences encoding human serum albumin (HSA) fused to one or two VLDs were produced, including a 16 amino acid linker sequence (SGGGGSGGGGSGGGGS SEQ ID NO: j) highlighted and a C-terminal histidine tag. The sequences were cloned into a mammalian expression vector. The vector used was the pcDNA3.4 vector (Thermo Fisher). The sequences were cloned with a signal peptide to allow the protein to be secreted. The sequence of the peptide was as follows MAWMMLLLGLLAYGSG (SEQ ID NO:8).

Vector transformation of bacteria was performed according to standard techniques using electroporation competent cells (e.g. ElectroTen-Blue cells, Stratagene Cat #200159).

Following vector amplification, plasmid DNA was extracted and prepared using Qiagen HiSpeed Plasmid Maxi Kit (Cat #12663) or Promega PureYield™ Plasmid Midiprep System (Cat #A2492). DNA was eluted in nuclease free purified water.

Transfection

Transfection of Expi293 mammalian cells at a density of $3-5 \times 10^6$ cells/mL and viability of >95% was performed using the Expi293 Expression System (Thermo Fisher Scientific Cat #A14635). The DNA vectors were added to Opti-MEM I Reduced Serum Medium (Life Technologies Cat #31985070) and ExpiFectamine 293 reagent (ThermoFisher Cat #A14525) and incubated at room temperature for 20 mins. The transfection complex was added to cells and incubated at 37° C., 5% $CO_2$ at 120 rpm. After 20 hours, Expifectamine 293 Transfection Enhancers 1 and 2 (ThermoFisher Cat #A14525) were added to the cells. Protein containing supernatant was harvested after approximately 4-5 days.

Purification

The proteins were purified by affinity chromatography using Nickel Sepharose Excel (GE, Cat #17-3712-01). A Nickel Sepharose column was equilibrated with 5 column volumes of 20 mM sodium phosphate, 0.5 M NaCl, ph7.4. The transfected cell culture supernatant containing the His-tagged HSA-VLD protein was loaded onto the column, and the column was washed with 10 column volumes of 20 mM sodium phosphate, 0.5 M NaCl, 5 mM imidazole, ph7.4. The protein was eluted with 20 mM sodium phosphate, 0.5 M NaCl, 500 mM imidazole ph7.4. The eluted fractions were pooled and dialysed with PBS according to standard methods.

FIG. 26 shows western blot analysis and detection with anti-His HRP (Sigma Aldrich, Cat #11965085001) of the purified HSA fusion proteins, which comprise of VLDs fused to the C-terminus, the N-terminus, or both the C-terminus and N-terminus of HSA. The estimated sizes of the proteins, respectively, are: 67 kDa (predicted size: 81.9 kDa); 69.3 kDa (predicted size: 81.8 kDa); and 94.4 kDa (predicted size: 96.2 kDa).

Assessment of Binding

The binding properties of the purified molecules were characterised using the ForteBio Blitz biosensor using standard chemistry and reagents.

The affinity purified molecules were tested with commercially available B7.2-Fc protein (R&D Systems, Cat #141-B2), CD3 (Acrobiosystems, Cat #CDD-H52W3), and biotinylated anti-HSA affibody (Abcam, Cat #31898).

CD3 and B7.2Fc proteins were biotinylated at 1:1 molar ratio using EZ-Link Sulfo-NHS-LC-Biotin (ThermoFisher, Cat #21327) according to standard methods.

A streptavidin capturing surface (SA Sensor, ForteBio cat #18-5019) was used to capture biotin labelled protein. The HSA-VLD molecule was passed over the target captured on the biosensor surface to generate a binding sensorgram.

FIG. 27 shows analysis using the ForteBio Blitz biosensor to demonstrate binding of the HSA-VLD molecules to streptavidin captured biotin labelled B7.2-Fc. Trace 1 is a sensorgram of the HSA-VLD fusion protein, which has a B7-binding VLD attached to the C-terminus. Trace 2 is a sensorgram of the VLD-HSA-VLD fusion protein, which has a B7-binding VLD attached to both the N-terminus and the C-terminus. The molecules are shown binding to B7.2-Fc immobilised on the biosensor surface followed by an addition of Buffer at Point 1.

FIG. 28 shows analysis using the ForteBio Blitz biosensor to demonstrate binding of the HSA-VLD molecule to streptavidin captured biotin labelled CD3 delta/epsilon (de) heterodimer. The trace shown is a sensorgram of the HSA-VLD fusion protein, which has a CD3-binding VLD attached to the C-terminus. The molecule is shown binding to CD3de immobilised on the biosensor surface followed by an addition of Buffer at Point 1.

FIG. 29 shows analysis using the ForteBio Blitz biosensor to demonstrate binding of the HSA-VLD molecule to streptavidin captured biotin labelled anti-HSA affibody. The trace shown is a sensorgram of the HSA-VLD fusion protein, which has a B7-binding VLD attached to the C-terminus. The molecule is shown binding to anti-HSA affibody immobilised on the biosensor surface followed by an addition of Buffer at Point 1. At Point 2, B7.2Fc protein was allowed to bind to the captured molecules on the sensor surface. B7.2Fc was then replaced with buffer at Point 3.

Results (i) CTLA4 VLD fused to Human Serum albumin at either the C-terminus, N-terminus or both the C and N terminus of HSA.

The sequences are shown below:

```
The B7-2 binding VLD fused to the C-terminus of HSA
(SEQ ID NO: 26):
DAHKSEVAHRFKDLGEENFKALVLIAFAQYLQQCPFEDHVKLVNEVTEFAKTCVADESAENCD

KSLHTLFGDKLCTVATLRETYGEMADCCAKQEPERNECFLQHKDDNPNLPRLVRPEVDVMCT

AFHDNEETFLKKYLYEIARRHPYFYAPELLFFAKRYKAAFTECCQAADKAACLLPKLDELRDEG

KASSAKQRLKCASLQKFGERAFKAWAVARLSQRFPKAEFAEVSKLVTDLTKVHTECCHGDLL

ECADDRADLAKYICENQDSISSKLKECCEKPLLEKSHCIAEVENDEMPADLPSLAADFVESKDV

CKNYAEAKDVFLGMFLYEYARRHPDYSVVLLLRLAKTYETTLEKCCAAADPHECYAKVFDEFK

PLVEEPQNLIKQNCELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSALEVDETYVPKEFNA

ETFTFHADICTLSEKERQIKKQTALVELVKHKPKATKEQLKAVMDDFAAFVEKCCKADDKETCF

AEEGKKLVAASQAALGLSGGGGSGGGGSGGGGSKAMHVAQPAVVLASSRGIASFVCEYASP

GKATEVRVTVLRQADSQVTEVCAATYMMGNELTFLDDSICTGTSSGNQVNLTIQGLRAMDTG

LYICKVELMYPPPYYLGIGNGTQIYVIDPEPSPDSAAAHHHHHH

The B7-1 binding VLD fused to the N-terminus of HSA
(SEQ ID NO: 27):
KAMHVAQPAVVLASSRGIASFVCEYASPGKATEVRVTVLRQADSQVTEVCAATYMMGNELTF

LDDSICTGTSSGNQVNLTIQGLRAMDTGLYICKVELMYPPPYYLGIGNGTQIYVIDPEPSPDSG

GGGSGGGGSGGGGSDAHKSEVAHRFKDLGEENFKALVLIAFAQYLQQCPFEDHVKLVNEVT

EFAKTCVADESAENCDKSLHTLFGDKLCTVATLRETYGEMADCCAKQEPERNECFLQHKDDN

PNLPRLVRPEVDVMCTAFHDNEETFLKKYLYEIARRHPYFYAPELLFFAKRYKAAFTECCQAAD

KAACLLPKLDELRDEGKASSAKQRLKCASLQKFGERAFKAWAVARLSQRFPKAEFAEVSKLVT

DLTKVHTECCHGDLLECADDRADLAKYICENQDSISSKLKECCEKPLLEKSHCIAEVENDEMPA

DLPSLAADFVESKDVCKNYAEAKDVFLGMFLYEYARRHPDYSVVLLLRLAKTYETTLEKCCAA

ADPHECYAKVFDEFKPLVEEPQNLIKQNCELFEQLGEYKFQNALLVRYTKKVPQVSTPTLVEV

SRNLGKVGSKCCKHPEAKRMPCAEDYLSVVLNQLCVLHEKTPVSDRVTKCCTESLVNRRPCF

SALEVDETYVPKEFNAETFTFHADICTLSEKERQIKKQTALVELVKHKPKATKEQLKAVMDDFA

AFVEKCCKADDKETCFAEEGKKLVAASQAALGLAAAHHHHHH

The B7-2 binding VLD fused to both the N-terminus and the C-terminus of HSA
(SEQ ID NO: 28):
KAMHVAQPAVVLASSRGIASFVCEYASPGKATEVRVTVLRQADSQVTEVCAATYMMGNELTF
```

-continued

LDDSICTGTSSGNQVNLTIQGLRAMDTGLYICKVELMYPPPYYLGIGNGTQIYVIDPEPSPDSG

GGGSGGGSGGGSDAHKSEVAHRFKDLGEENFKALVLIAFAQYLQQCPFEDHVKLVNEVT

EFAKTCVADESAENCDKSLHTLFGDKLCTVATLRETYGEMADCCAKQEPERNECFLQHKDDN

PNLPRLVRPEVDVMCTAFHDNEETFLKKYLYEIARRHPYFYAPELLFFAKRYKAAFTECCQAAD

KAACLLPKLDELRDEGKASSAKQRLKCASLQKFGERAFKAWAVARLSQRFPKAEFAEVSKLVT

DLTKVHTECCHGDLLECADDRADLAKYICENQDSISSKLKECCEKPLLEKSHCIAEVENDEMPA

DLPSLAADFVESKDVCKNYAEAKDVFLGMFLYEYARRHPDYSVVLLLRLAKTYETTLEKCCAA

ADPHECYAKVFDEFKPLVEEPQNLIKQNCELFEQLGEYKFQNALLVRYTKKVPQVSTPTLVEV

SRNLGKVGSKCCKHPEAKRMPCAEDYLSVVLNQLCVLHEKTPVSDRVTKCCTESLVNRRPCF

SALEVDETYVPKEFNAETFTFHADICTLSEKERQIKKQTALVELVKHKPKATKEQLKAVMDDFA

AFVEKCCKADDKETCFAEEGKKLVAASQAALGLSGGGGSGGGGSGGGGSKAMHVAQPAVV

LASSRGIASFVCEYASPGKATEVRVTVLRQADSQVTEVCAATYMMGNELTFLDDSICTGTSSG

NQVNLTIQGLRAMDTGLYICKVELMYPPPYYLGIGNGTQIYVIDPEPSPDSAAAHHHHHH (ii) CD3 binding VLD (referred to as AF3) fused to the C-terminus of human serum albumin
The sequence is shown below:
The CD3-binding VLD "AF3" fused to the C-terminus of HSA
(SEQ ID NO: 29):
DAHKSEVAHRFKDLGEENFKALVLIAFAQYLQQCPFEDHVKLVNEVTEFAKTCVADESAENCD

KSLHTLFGDKLCTVATLRETYGEMADCCAKQEPERNECFLQHKDDNPNLPRLVRPEVDVMCT

AFHDNEETFLKKYLYEIARRHPYFYAPELLFFAKRYKAAFTECCQAADKAACLLPKLDELRDEG

KASSAKQRLKCASLQKFGERAFKAWAVARLSQRFPKAEFAEVSKLVTDLTKVHTECCHGDLL

ECADDRADLAKYICENQDSISSKLKECCEKPLLEKSHCIAEVENDEMPADLPSLAADFVESKDV

CKNYAEAKDVFLGMFLYEYARRHPDYSVVLLLRLAKTYETTLEKCCAAADPHECYAKVFDEFK

PLVEEPQNLIKQNCELFEQLGEYKFQNALLVRYTKKVPQVSTPTLVEVSRNLGKVGSKCCKHP

EAKRMPCAEDYLSVVLNQLCVLHEKTPVSDRVTKCCTESLVNRRPCFSALEVDETYVPKEFNA

ETFTFHADICTLSEKERQIKKQTALVELVKHKPKATKEQLKAVMDDFAAFVEKCCKADDKETCF

AEEGKKLVAASQAALGLSGGGGSGGGGSGGGGSKAMHVAQPAVVLASSRGIASFVCEYLLDI

EPEFVRVTVLRQADSQVTEVCAATYQLQWMLTFLDDSICTGTSSGNQVNLTIQGLRAMDTGLY

ICKVEWSREWGRQGLGIGNGTQIYVIDPEPSPDSAAAHHHHHH

---

The invention claimed is:

1. A multi-specific molecule which binds to two or more different target antigens or epitopes, the molecule comprising:
   (i) at least one binding domain molecule (BDM) which binds to a first target antigen or epitope, the BDM has first, second, and third binding loops and has the amino acid sequence set forth in SEQ ID NO:5; and
   (ii) a full length antibody or an antigen-binding fragment thereof which binds to a second target antigen or epitope; wherein the at least one BDM is coupled via its N-terminus to a C-terminus of a heavy and/or light chain of the antibody or antigen binding fragment thereof by a peptide linker as set forth in SEQ ID NO: 16 or SEQ ID NO: 17.

2. The molecule according to claim 1, wherein at least one BDM is coupled to a C-terminus of all antibody heavy and light chains.

3. The molecule according to claim 1, wherein the antibody is a full length antibody.

4. The molecule according to claim 3, wherein the ratio of antibody chains to BDMs is 4:(2″) where n is a number between 1 and 5.

5. The molecule according to claim 1, wherein the antigen-binding fragment is selected from the group consisting of a Fab, Fab', F(ab')2 and chemically linked F(ab')$_2$.

6. The molecule according to claim 5, wherein the ratio of antigen-binding fragment chains to BDMs is 2:(2″) wherein n is a number between 0 and 5.

7. The molecule according to claim 1, wherein at least one BDM is coupled to a C-terminus of the CH1, CH2 or CH3 domain of the heavy chain.

8. The molecule according to claim 1, wherein the first target antigen and the second target antigen are different.

9. The molecule according to claim 1, wherein the first target epitope and the second target epitope are on different antigens.

10. The molecule according to claim 1, wherein the molecule is bi-specific or tri-specific.

11. The molecule according to claim 1, wherein the molecule comprises one, two, three, four, five or six BDMs.

12. The molecule according to claim 1, wherein the molecule comprises one pair or two pairs of BDMs wherein the BDMs in the pair are identical.

13. The molecule according to claim 1, wherein the at least one BDM is linked to one or more further BDMs.

14. The molecule according to claim 1, wherein the molecule comprises at least two BDMs, or at least one pair of BDMs, wherein each BDM or BDM pair binds to a different target antigen or epitope.

15. The molecule according to claim 1, wherein each BDM binds to a target antigen or epitope that is different from the target antigen epitope to which the antibody or antigen binding fragment thereof binds.

16. The molecule according to claim 1, wherein the first binding loop is between 5 and 8 amino acids, the second binding loop is between 5 and 8 amino acids, and the third binding loop is between 10 and 15 amino acids.

17. The molecule according to claim 16, wherein:
   (a) the first binding loop is 8 amino acids;
   (b) the second binding loop is 5 amino acids; and
   (c) the third binding loop is between 10 and 15 amino acids.

18. The molecule according to claim 1, wherein the at least one BDM is present as a monomer or a series of BDM monomers linked together.

19. The molecule according to claim 1 comprising the BDM of SEQ ID NO: 13 or SEQ ID NO:14.

20. The molecule according to claim 1, wherein the molecule is labelled with an agent to facilitate detection.

21. A pharmaceutical composition comprising the molecule according to claim 1, together with a pharmaceutically acceptable carrier and/or excipient.

* * * * *